United States Patent [19]
Srivastava et al.

[11] Patent Number: 5,877,157
[45] Date of Patent: *Mar. 2, 1999

[54] MODIFIED KOJIBIOSIDE ANALOGUES

[75] Inventors: Om Srivastava; Roman Szweda, both of Edmonton, Canada; Ulrike Spohr, Boulder, Colo.

[73] Assignee: Alberta Research Council, Edmonton, Canada

[ * ] Notice: The term of this patent shall not extend beyond the expiration date of Pat. No. 5,633,233.

[21] Appl. No.: 813,493

[22] Filed: Mar. 7, 1997

Related U.S. Application Data

[63] Continuation of Ser. No. 481,645, Jun. 7, 1995, Pat. No. 5,633,233.
[51] Int. Cl.⁶ .......................... A61K 31/20; C07H 15/00
[52] U.S. Cl. ........................ 514/25; 514/53; 536/16.8; 536/17.2; 536/17.6; 536/18.1
[58] Field of Search ...................... 514/25, 53; 536/16.3, 536/17.2, 17.6, 18.1

[56] References Cited

U.S. PATENT DOCUMENTS 4,335,101  6/1982  Stoudt et al. .
5,079,353  1/1992  Ratcliffe et al. .

OTHER PUBLICATIONS

Gallo et al., *Science*, 220:865 (1983).
Barre–Sinoussi et al., *Science*, 220:868 (1983).
Montagnier et al., *Virology*, 144:283 (1985).
McDougal et al., *Science*, 231: 382 (1986).
Allan et al., *Science*, 228:1091 (1985).
Ratner et al., *Nature*, 313:277 (1985).
Fellows et al., *Pure Appl. Chem.*, 59:1457 (1987).
Frommer et al., *Planta Med.*, 35:195 (1979).
Romero et al., *Biochem J.*, 226:733 (1985).
Schweden et al., *Biochem Biophys.*, 248:335 (1986).
Hayashida et al., *Carbohydr. Res.*, 158:c5 (1986).
Schmidt et al., *Naturwissenschaften* 64:535 (1977).
Junge et al., *Chem Abst.*, 8:198,655g (1983).
Aso et al., *Tohoku J. Agric. Res.*, 3:337 (1953).
Shibasaki et al., *Tohoku J. Agric. Res.*, 6:171 (1955).
Matsuda et al., *Chem. Abst.*, 49:2670 (1955).
Watanabe et al., *Nature*, 183:1740 (1959).
Sato et al., *Nature*, 180:984 (1957).
Matsuda et al., *Nature*, 191:278 (1961).
Bailey et al., *J. Chem. Soc.*, 1895 (1958).
Aso et al., *Nature*, 182:1303 (1958).
Aspinall et al., *Carbohydr. Res.*, 143:266 (1985).
Abbas, et al., *Proc. Japanese–German Symp. Berlin*, pp. 20–21 (1988).
Paulsen, *Agnew. Chem. Int. Ed. Eng.*, 21:155–173 (1982).
Schmidt, *Agnew. Chem. Int. Ed. Eng.*, 25:212–235 (1986).
Fügedi, et al., *Glycoconj. J.*, 4:97–108 (1987).
Kameyama, et al., *Carbohydr. Res.*, 209:$C_1$–$C_4$ (1991).
Hercouvics et al., *J. Biol. Chem.*, 252:2271 (1987).
Saunier et al., *J. Biol. Chem.*, 257: 14155 (1982).

Bause, et al., *FEBS Letters*, 278(2):167–170 (1991).
Kornfeld, et al., *J. Biol. Chem.*, 253:7771 (1978).
Shailubhai et al., *Biochem. J.*, 247:555 (1987).
Brady et al., *J. Immunol.*, 149:2437–2444 (1992).
Neverova et al., *Anal. Biochem.*, 222: 190–195 (1994).
Schaubach et al., *Liebigs. Ann. Chem.*, 607–614 (1991).
David et al., Tetrahedron Report No. 180, *Tetrahedron*, vol. 41, No. 4: 643–663(Ref. 3).
Aspinall, G., et al., "8–Methoxycarbonyloctyl 2–O–α–D–glucopyranosyl–α–D–glucopyranoside", *Carbohydrate Research*, 143:266–270 (1985).
Chemical Abstracts, vol. 100, No. 21, p. 359, abstract No. 171583e, I. Varshney, "Saponins from *Trigonella foenum–graecum* leaves".
Glaudemans, C., et al., "The Subsites of Monoclonal Anti–Dextran IgA W3129", *Carbohydrate Research*, 190:267–277 (1989).
Koto, S., et al., "Synthesis of Branched–Chain Oligosaccharides in Sarsasaponins by Dehydrative Glycosylation", *Bull. Chem. Soc. Jpn.*, 61:3943–3950 (1988).
Takeo, K., et al., "Selective α–D–glucosylation of methyl 4,6–O–benzylidene–α– and β–D–gluco–pyranosides with 2,3,4,6–tetra–O–benzyl–α–D–glucopyranosyl bromide under catalysis by halide ion", *Carbohydrate Research*, 145:307–311 (1986).
Takeuchi, M., et al., "Inhibitory Effect of Pseudo–Aminosugars on Oligosaccharide Glucosidases I and II and on Lysosomal α–Glucosidase from Rat Liver", *J. Biochem.* 108:42–46 (1990).
International Publication No. WO 91/18915, publication date 12 Dec. 1991, Ducep, J., et al., "Novel α–Glucosidase Inhibitors".
European Publication No. 0 173 948 A2, dated of publication 12 Mar. 1986.
European Publication No. 0 557 887, date of publication 01 Sep. 1993, L. Liverani, "Polysaccharide derivatives of heparin, heparan sulphate, fraction and fragments thereof, process for their preparation and pharmaceutical compositions containing them".
Takeuchi et al., *J. Biol. Chem.*, 108:42 (1990).
Shailubhai et al., *Biochem. J.*, 247:555 (1987).
Bause et al., *FEBS Lett.*, 206(2) (1986).
Szumilo et al., *Arch. Biochem. Biophys.*, 247:261 (1986).
Hindsgaul et al., *Can. J. Chem.*, 63:2653 (1985).
Spohr et al., *Can. J. Chem.*, 63:2659 (1985).
Lemieux et al., *Can. J. Chem.*, 63:2664 (1985).
Lemieux, R.U., *Proceedings for the International Symposium on Medicinal Chemistry*, Uppsala, Sweden: 329 (1984).
Kelly et al., *Biochem. J.*, 245:843 (1982).
Legler, G., *Pure Appl. Chem.*, 59(11):1457 (1987).
Kite et al., *Tetrahedr. Lett.*, 29(49):6483 (1988).

(List continued on next page.)

*Primary Examiner*—Elli Peselev
*Attorney, Agent, or Firm*—Burns, Doane, Swecker & Mathis, L.L.P.

[57] ABSTRACT

Disclosed are novel analogues of kojibiose and pharmaceutical compositions comprising such analogues.

26 Claims, 7 Drawing Sheets

OTHER PUBLICATIONS

Srivastava et al., *XVth International Carbohydrate Symposium* (1990).
Feizi et al., *Glycobiology*, 1(1):17–23 (1990).
Takeo et al., *Carbohydrate Research*, 162:95–109 (1987).
Tan, et al., *J. Biol. Chem.*, 266(22):14504–14510 (1991).
Takeuchi, et al., *Chem. Pharm. Bull.*, 38(7):1970–1972 (1990).
Ishida, et al., *Carb. Research*, 208:267–272 (1990).
Okamoto, et al., *Tetrahedron*, 46(17):5835–5837 (1990).

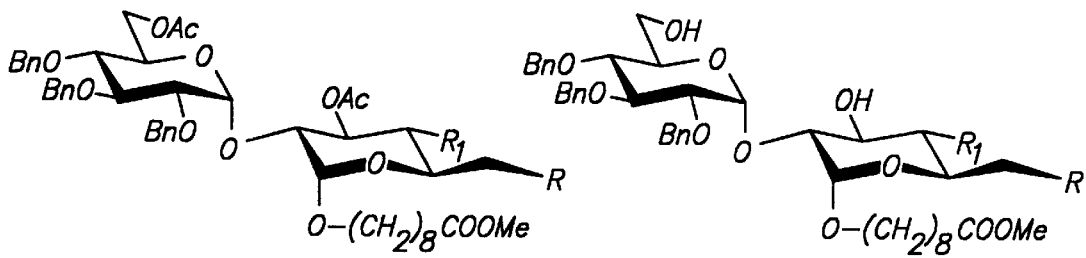

24 R=OH, $R_1$=OH
25 R=OMs, $R_1$=OH
26 R=$N_3$, $R_1$=OH
27 R=Cl, $R_1$=OH
28 R=I, $R_1$=OH
29 R=H, $R_1$=OH
30 R=OSi(Me)$_2$tert-Bu, $R_1$=OH
31 R=OSi(Me)$_2$tert-Bu, $R_1$=OCSOPh
32 R=OSi(Me)$_2$tert-Bu, $R_1$=H 33 R=OSi(Me)$_2$tert-Bu, $R_1$=H
34 R=$N_3$, $R_1$=OH
35 R=Cl, $R_1$=OH
36 R=H, $R_1$=OH
37 R=OH, $R_1$=H

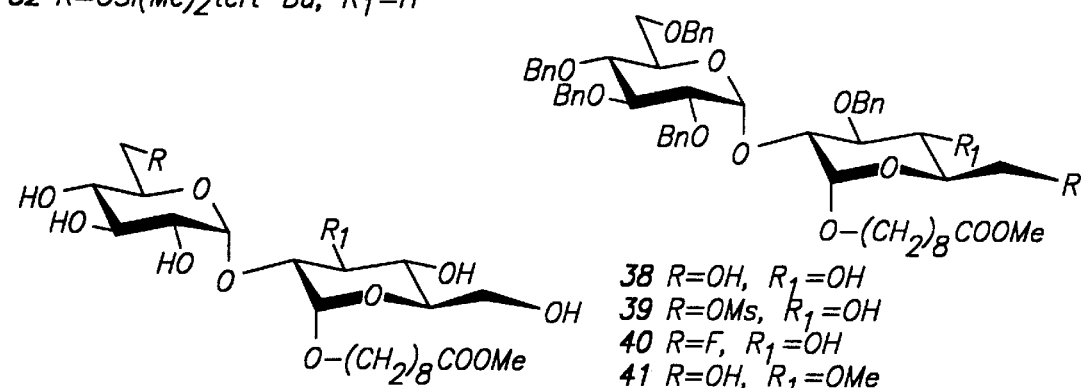

44 R=OH, $R_1$=OH
45 R=OMs, $R_1$=OH
46 R=$N_3$, $R_1$=OH
47 R=$NH_2$, $R_1$=OH
48 R=Cl, $R_1$=OH
49 R=F, $R_1$=OH
50 R=H, $R_1$=OH
51 R=OH, $R_1$=OMe
52 R=OMe, $R_1$=OH
53 R=OMe, $R_1$=OMe
54 R=OH, $R_1$=H

38 R=OH, $R_1$=OH
39 R=OMs, $R_1$=OH
40 R=F, $R_1$=OH
41 R=OH, $R_1$=OMe
42 R=OMe, $R_1$=OH
43 R=OMe, $R_1$=OMe

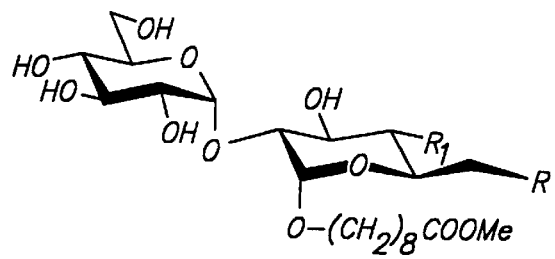

55 R=OMs, $R_1$=OH
56 R=$N_3$, $R_1$=OH
57 R=$NH_2$, $R_1$=OH
58 R=Cl, $R_1$=OH
59 R=F, $R_1$=OH
60 R=H, $R_1$=OH
61 R=OH, $R_1$=OMe
62 R=OMe, $R_1$=OH
63 R=OMe, $R_1$=OMe
64 R=OH, $R_1$=H

*FIG. 3*

MODIFIED KOJIBIOSIDE ANALOGUES

This application is a divisional of application Ser. No. 08/481,645, filed Jun. 7, 1995, now U.S. Pat. No. 5,633,233.

BACKGROUND OF THE INVENTION

Field of the Invention

The invention relates to the field of oligosaccharide glycosides. In particular, the invention is directed to modified analogues of kojibioside and pharmaceutical compositions comprising such analogues.

REFERENCE

The following references are cited as superscript numbers at the relevant point of reference in the text.

1 Gallo et al., *Science*, 220:865 (1983)
2 Barre-Sinoussi et al., *Science*, 220:868 (1983)
3 Montagnier et al., *Science*, 144:283 (1985)
4 McDougal et al., *Science*, 231:382 (1986)
5 Allan et al., *Science*, 228:1091 (1985).
6 Ratner et al., *Nature*, 313:277 (1985).
7 Fellows et al., *Pure Appl. Chem.*, 59:1457 (1987)
8 Frommer et al., *Planta Med.*, 35:195 (1979).
9 Romero et al., *Biochem. J.*, 226:733 (1985).
10 Schweden et al., *Biochem. Biophys.*, 248:335 (1986).
11 Hayashida et al., *Carbohydr. Res.*, 158:c5 (1986).
12 Schmidt et al., *Naturwissenschaften* 64:535 (1977).
13 Junge et al., *Chem. Abst.*, 8:198,655g (1983).
14 Aso et al., *Tokoku J. Agric. Res.*, 3:337 (1953).
15 Shibasaki et al., *Tokoku J. Agric. Res.*, 6:171 (1955).
16 Matsuda et al., *Chem. Abst.*, 49:2670 (1955).
17 Watanabe et al., *Nature*, 183:1740 (1959).
18 Sato et al., *Nature*, 180:984 (1957).
19 Matsuda et al., *Nature*, 191:278 (1961).
20 Bailey et al., *J. Chem. Soc.*, 1895 (1958).
21 Aso et al., *Nature*, 182:1303 (1958).
22 Aspinall et al., *Carbohydr. Res.*, 143:266 (1985).
23 Takeuchi et al., *J. Biol. Chem.*, 108:42 (1990).
24 Shailubhai et al., *Biochem. J.*, 247:555 (1987).
25 Bause et al., *FEBS Lett.*, 206(2) (1986).
26 Szumilo et al., *Arch. Biochem. Biophys.*, 247:261 (1986).
27 Hindsgaul et al., *Can. J. Chem.*, 63:2653 (1985).
28 Spohr et al., *Can. J. Chem.*, 63:2659 (1985).
29 Lemieux et al., *Can. J. Chem.*, 63:2664 (1985).
30 Lemieux, R. U., *Proceedings for the International Symposium on Medicinal Chemistry*, Uppsala, Sweden: 329 (1984).
31 Kelly et al., *Biochem. J.*, 245:843 (1982).
32 Legler, G., *Pure Appl. Chem.*, 59(11):1457 (1987).
33 Geoffrey et al., *Tetrahedr. Lett.*, 29(49):6483 (1988).
34 Srivastava et al., *XVth International Carbohydrate Symposium* (1990).
35 Feizi et al., *Glycobiology*, 1(1):17–23 (1990).
36 Takeo et al., *Carbohydrate Research*, 162:95–109 (1987).
37 Tan, et al., *J. Biol. Chem.*, 266(22):14504–14510 (1991)
38 Takeuchi, et al., *Chem. Pharm. Bull.*, 38(7):1970–1972 (1990)
39 Ishida, et al., *Carb. Research*, 208:267–272 (1990)
40 Okamoto, et al., *Tetrahedron*, 46(17):5835–5837 (1990).
41 Abbas, et al., *Proc. Japanese-German Symp. Berlin*, pp. 20–21 (1988).
42 Paulsen, *Agnew. Chem. Int. Ed. Eng.*, 21:155–173 (1982).
43 Schmidt, *Agnew. Chem. Int. Ed. Eng.*, 25:212–235 (1986).
44 Fufgedi, et al., *Glycoconj. J.*, 4:97–108 (1987).
45 Kameyama, et al., *Carbohydr. Res.*, 209:$C_1$–$C_4$ (1991).
46 Ratcliffe, et al., U.S. Pat. No. 5,079,353.
47 Hercouvics et al., *J. Biol. Chem.*, 252:2271 (1987).
48 Saunier et al., *J. Biol. Chem.*, 257:14155 (1982).
49 Bause, et al., *FEBS Letters*, 278(2):167–170 (1991)
50 Komfeld, et al., *J. Biol. Chem.*, 253:7771 (1978)
51 Shailubhai et al., *Biochem. J.*, 247:555 (1987).
52 Hercouvics et al., *J. Biol. Chem.*, 252:2271 (1987).
53 Saunier et al., *J. Biol. Chem.*, 257:14155 (1982).

The above references are incorporated herein by reference in their entirety to the same extent and in the same manner as if each individual reference was specifically and individually incorporated by reference in its entirety.

State of the Art

Glucosidase inhibitors have been shown to display antiviral activities.[37] For example, human immunodeficiency virus type 1 (HIV-1), the causative agent of acquired immune deficiency syndrome (AIDS), is an enveloped retrovirus, cytopathic for $T_4^+$ ($CD_4^+$) lymphocytes[1,2]. HIV-1 possesses two glycosylated enveloped proteins: gp120 which binds to $CD_4$ antigen of $T_4^+$ T lymphocytes; and a transmembrane protein, glycoprotein gp41, which anchors the envelope in the viral membrane. The viral glycoproteins and host $CD_4$ surface receptor play an important role in virus adsorption, penetration, syncytium formation and spread of virus to adjacent cells[3,4].

Carbohydrates comprise approximately 50% of the total mass[5,6] of gp 120 with all 24 sites that contain the consensus N-glycosylation being glycosylated[35]. Carbohydrates are known to be involved in the binding/recognition of $CD_4$ antigens by gp120 and it appears that the processing of oligosaccharides on gp120 via the so-called "trimming" pathway is important for viral infectivity. Inhibition of α-glucosidase I prevents the removal of glucose residues during the normal processing of the HIV gp120 membrane protein, and results in altered glycoproteins that have been implicated in breaking the virus replication cycle. The inhibitors are, therefore, therapeutic agents. It would be pharmacologically advantageous to replace existing inhibitors of α-glucosidase I by agents of lower toxicity, greater specificity and/or superior binding capability.

The major pathway in the glycosylation of glycoprotein begins with co-translational transfer of the precursor dolichol derivative of oligosaccharide $Glc_3Man_9$ $GlcNAc_2$ to asparagine residues of nascent protein[6]. The subsequent synthesis of complex-N-linked oligosaccharides occurs in the endoplasmic reticulum by processing of oligosaccharides via the trimming pathway. The first step in this process (FIG. 1) is the removal of the distal α-(1–2) linked glucose residue by the action of the glucosidase I enzyme, followed by the removal of the two α-(1–3) linked glucose residues. Subsequent trimming of four mannose residues occurs within the Golgi complex by the action of mannosidase I. Addition of N-acetylglucosamine, removal by mannosidase II of two more mannose residues, and the addition of distal sugars such as galactose, N-acetylglucosamine, fucose and sialic acid residues by the corresponding glycosyltransferases, completes the process[6].

There has been much effort to find inhibitors of glucosidase or mannosidase "trimming enzymes", owing to their potential as therapeutic agents[7]. Nojirimycin, deoxynojirimycin, castanospermine and several other analogues of these compounds have been reported in the literature[8,9,10]. Other examples of glucosidase inhibitors include the naturally occurring pseudotetrasaccharide acarbose and a synthetic analog, dihydroacarbose[11] (both possessing nitrogen in the terminal glycosidic linkage). Both were found to be potent α-glucosidase inhibitors[12,13].

Additionally, due to their glucosidase inhibition, these compounds have been disclosed for limiting digestion of dietary carbohydrates by inhibition of intestinal α-glucosidases thereby providing a regimen for treating diabetes mellitus and obesity[38].

Kojibiose, an α-(1–2) linked glucose disaccharide has been isolated from various ferments,[14,15,16] honey[17], starch hydrol[18] and from partial acetolysates of dextrans[19]. Partial enzymic hydrolysates of the trisaccharides formed by dextransucrose actions also yield kojibiose[20,21]. Aspinall, et al.[22] synthesized kojibiose as its 8-methoxycarbonyloctyl glycoside. Kojibiose inhibited α-glucosidase I from rat liver microsomes[23], bovine mammary gland[24], yeast microsomal preparation[25] and from mung bean seedlings[26]. The main advantage of kojibiose as an inhibitor lies in the fact that it specifically inhibits glycosidase I. Kojibiose was found to inhibit glucosidase action on soluble and protein-bound oligosaccharide.

K. Takeo and Y. Suzuki[36] reported the systematic synthesis of a homologous series of lower koji-oligosaccharides.

It would be desirable to produce oligosaccharide-based inhibitors of so-called "trimming glucosidases" which are essential to the biosynthesis of N-linked glycoproteins in human cells.

SUMMARY OF THE INVENTION

This invention is directed to oligosaccharides which are modified analogues of kojibiose (α-D-Glcp-(1–2)-α-D-Glcp). The oligosaccharides within the scope of the present invention are α-glucosidase I inhibitors or intermediates in the production of α-glucosidase I inhibitors.

Accordingly, the present invention is directed to compounds represented by formulas I, II, III, IV, VII and VIII which are intermediates used in the synthesis of glucosidase I inhibitors as well as to compounds of formula V, VI, IX, X, XI, XII and XIII which are newly discovered glucosidase I inhibitors.

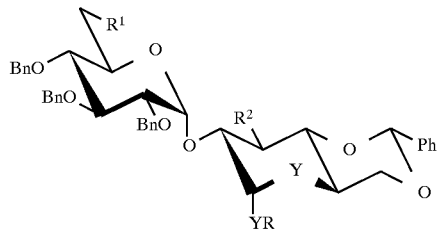

I wherein each Y is independently —O— or —NH—, R is an aglycon of at least one carbon atom, $R^1$ is selected from the group consisting of —O-acetyl, —OH, —O-mesityl, —$N_3$, —Cl, —F, —I, —H, —O-methyl, —OSi($CH_3$)$_2$-tert-butyl and —O-benzyl; and $R^2$ is selected from the group consisting of —O-acetyl, —OH, —O-methyl, —OC(S)O-phenyl, —H and —O-benzyl.

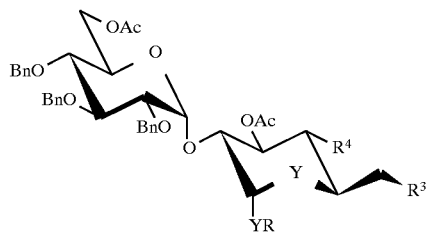

II wherein each Y is independently —O— or —NH—, R is an aglycon of at least one carbon atom, $R^3$ is selected from the group consisting of —OH, —O—-mesityl, —$N_3$, —Cl, —I, —H, —OSi($CH_3$)$_2$-tert-butyl; and $R^4$ is selected from the group consisting of —OH, —H and —OC(S)O-phenyl.

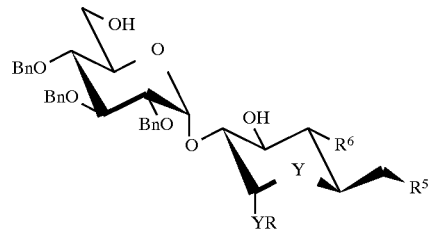

III wherein each Y is independently —O— or —NH—, R is an aglycon of at least 1 carbon atom, $R^5$ is selected from the group consisting of —OSi($CH_3$)$_2$ tert-butyl, —$N_3$, —Cl, —H and —OH and $R^6$ is selected from the group consisting of hydrogen or —OH.

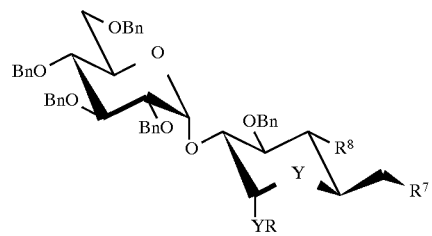

IV wherein each Y is independently —O— or —NH—, R is an aglycon of at least one carbon atom, $R^7$ is selected from the group consisting of —OH, —O-mesityl, —F, —OH and —O-methyl; and $R^8$ is selected from the group consisting of —OH and —O-methyl.

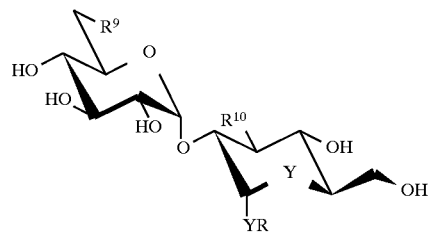

V wherein each Y is independently —O— or —NH—, R is an aglycon of at least 1 carbon atom, $R^9$ is selected from the group consisting of —O-mesityl, —$N_3$, —$NH_2$, —Cl, —F, —H, —OH, and —O-methyl and $R^{10}$ is selected from the group consisting of —OH, —H and —O-methyl, with the proviso that when each Y is —O— and $R^9$ is hydroxyl, then $R^{10}$ is not hydroxyl.

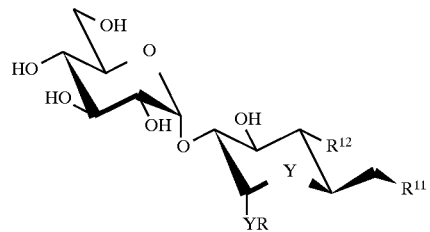

VI wherein each Y is independently —O— or —NH—, R is an aglycon of at least 1 carbon atom, $R^{11}$ is selected from the group consisting of —O-mesityl, —$N_3$, —$NH_2$, —Cl, —F, —H, —OH and —O-methyl and $R^{12}$ is selected from the group consisting of —OH, —H and —O-methyl with the proviso that when each Y is —O— and $R^{11}$ is hydroxyl, then $R^{12}$ is not hydroxyl.

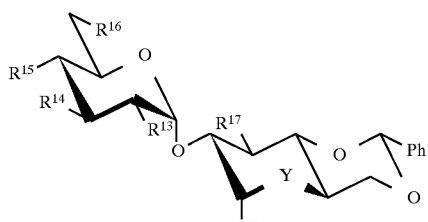

VII wherein each Y is independently —O— or —NH—, R is an aglycon of at least one carbon atom, $R^{13}$ is selected from the group consisting of —F, —$N_3$, —O-methyl, —H, and —O-benzyl; $R^{14}$ is selected from the group consisting —O-acetyl, —OH, —O-benzyl, —H and —O-methyl; $R^{15}$ is selected from the group consisting —O-acetyl, —OH, —O-benzyl, —H and —O-methyl; $R^{16}$ is selected from the group consisting of —OH, O-acetyl and —O-benzyl; and $R^{17}$ is selected from the group consisting of —O-acetyl and —OH.

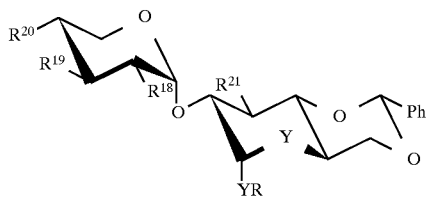

VIII wherein each Y is independently —O— or —NH—, R is an aglycon of at least 1 carbon atom, $R^{18}$, $R^{19}$ and $R^{20}$ are —O-benzyl and $R^{21}$ is —O-acetyl or —OH.

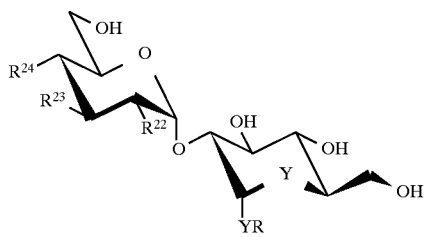

IX wherein each Y is independently selected from —O— or —NH—, R is an aglycon of at least 1 carbon atom, $R^{22}$ is selected from the group consisting of —F, —$N_3$, —$NH_2$, —O-methyl, —H and —OH; and $R^{23}$ and $R^{24}$ are selected from the group consisting of —OH, —H and —O-methyl with the proviso that when each Y is oxygen, $R^{22}$ and $R^{23}$ are hydroxyl then $R^{24}$ is not hydroxyl.

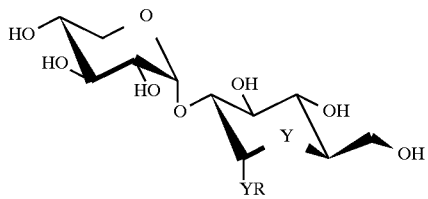

X wherein each Y is independently —O— or —NH— and R is an aglycon of at least 1 carbon atom.

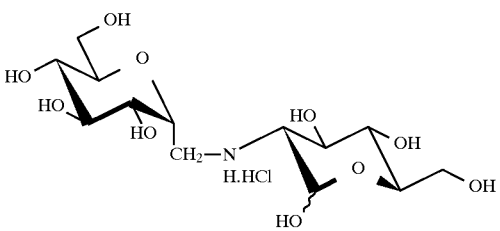

XI

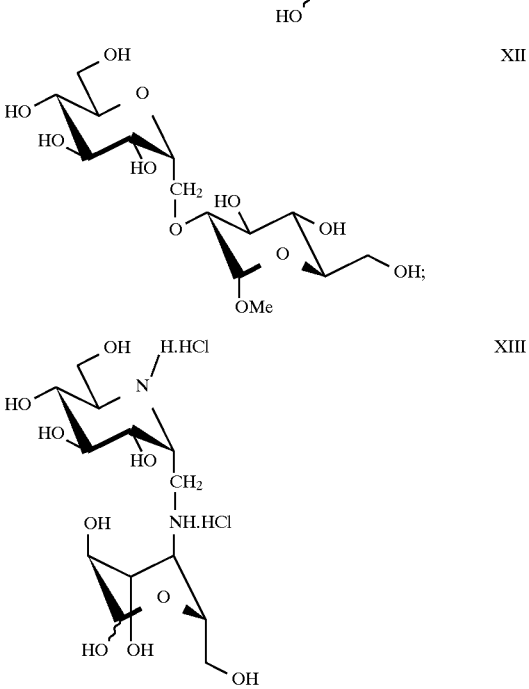

This invention is also directed to pharmaceutical compositions comprising a pharmaceutically inert carrier and from 0.1 to 95 weight percent of a compound of formula V, VI and IX–XIII described above.

BRIEF DESCRIPTION OF THE DRAWINGS

FIGS. 2–4 illustrate blocked monosaccharides and disaccharides used in the synthesis of kojibiose and analogues of kojibiose resulting therefrom.

DESCRIPTION OF PREFERRED EMBODIMENTS

Figure 1:
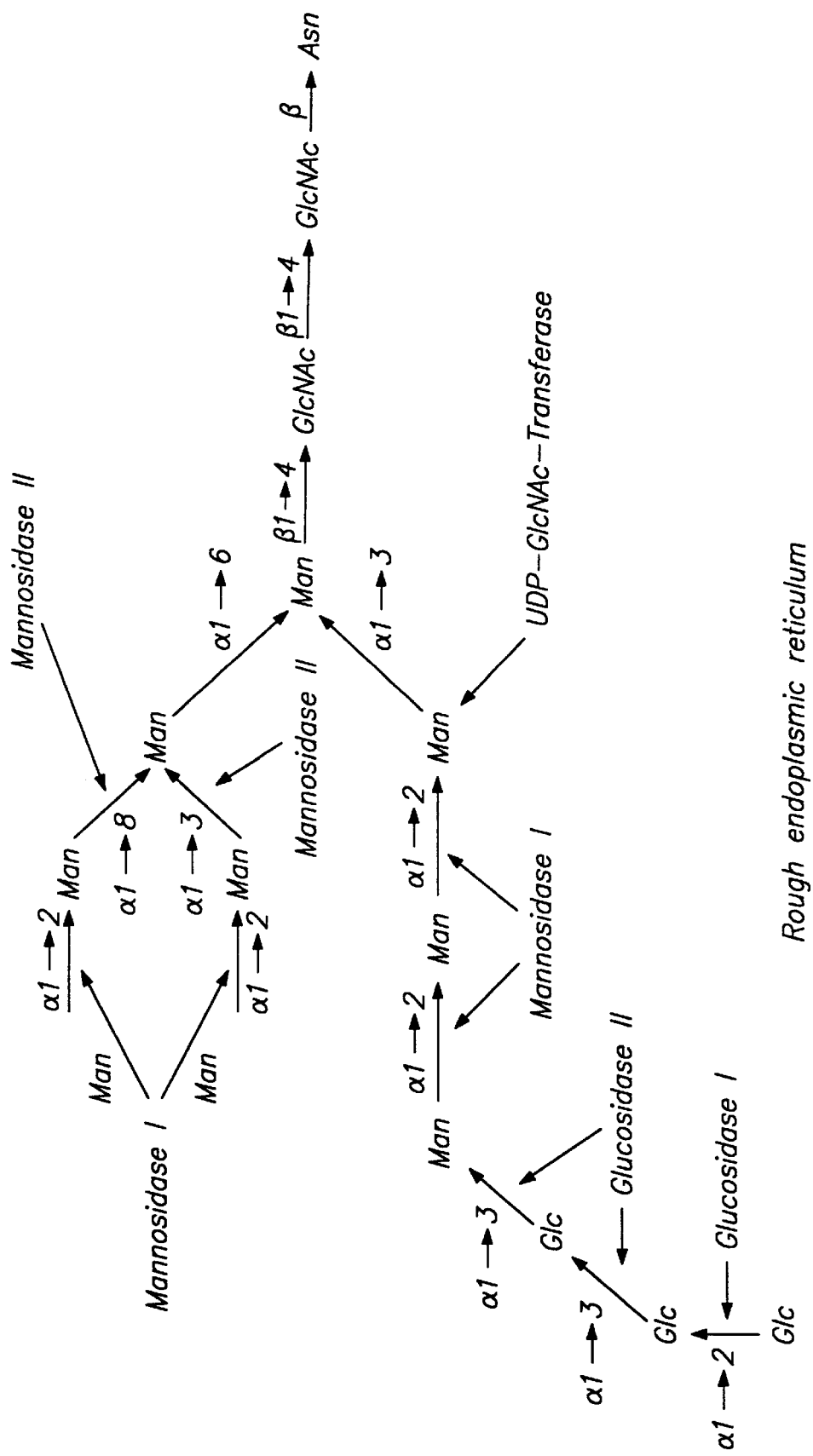
FIG. 1 illustrates the composite structure $Glc_3Man_9GlcNAc_2$, transferred from dolichylpyrophosphate to asparagine residues of the protein with trimming sites.

This invention is directed to the discovery of noval analogues of kojibioside. These compounds have been synthesized as an aglycon (e.g., 8-methoxycarbonyloctyl derivative) and each hydroxyl group in the kojibioside compounds can be modified as shown herein.

However, before discussing this invention in further detail, the following terms will be defined.

Definitions

As used herein, the following terms have the meaning given below:

The term "an enveloped virus" refers to a virus the surface of which is extensively covered by carbohydrate, in particular, glycoprotein. Glycoprotein is carbohydrate in the form of an array of oligosaccharide structures attached to the polypeptide backbone. The acquired immune deficiency syndrome (AIDS) is caused by an enveloped virus (HIV-1).

The term "oligosaccharide" refers to a carbohydrate structure having from 2 to about 7 saccharide units (disaccharides, trisaccharides, etc.). The particular saccharide units employed are not critical, and include by way of example, all natural and synthetic derivatives of glucose. In addition to being in their pyranose form, all saccharide units within the scope of this invention are preferably in their D form except for fucose which is in its L-form. The oligosaccharide chains are added to the glycoprotein and variously processed by enzymes of the host cell.

The term "glycosylation" refers to the enzymatic process in which oligosaccharides are added to glycoproteins.

The term "α-glucosidase I" or "glucosidase I" refers to a specific enzyme which participates in glycosylation of the HIV glycoprotein, gp120.

The term "glucosidase inhibitors" refers to naturally occurring and synthetic compounds of diverse chemical structure which interfere with processing of oligosaccharides by glucosidase enzymes. Likewise, the term "inhibitors of α-glucosidase I" refers to naturally occurring and synthetic compounds of diverse chemical structure which interfere with processing of oligosaccharides by glucosidase I. Certain inhibitors of glucosidase I are oligosaccharides.

The term "modified analogues of kojibioside" or "modified kojibioside", refers to molecules which retain the 2-O-(α-D-glucopyranosyl)-α-D-glucopyranoside structure of kojibioside, but contain at least one substituent which differs from that of kojibioside. That is, the kojibioside had been chemically modified so as to introduce and/or remove one or more functionalities from the kojibioside. For example, such modification can result from the removal of a —OH functionality, the introduction of an amine functionality, the introduction of an azido functionality or halo functionality, and so forth.

In this connection, a modification of particular interest and usefulness is the insertion of an aglycon functionality at the carbon 1 position of the α-D-glucopyranoside ring of kojibioside, or other suitable ring location useful in conjugation of the moieties prepared according to the methods of this invention.

The aglycons are non-saccharide groups containing at least one carbon atom, generally found in the oligosaccharide structures in the 1-position of the reducing sugar, (i.e., —YR). In general, Y is selected from the group consisting of oxygen and —NH—, and R is an aglycon of at least 1 carbon atoms. Preferably, R is selected from the group consisting of —(A)—Z wherein A represents a bond, an alkylene of from 2 to 12 carbon atoms, a moiety of the formula —(CH$_2$—CR'G)$_n$— where n is an integer of from 1 to 5, R' is selected from the group consisting of H, methyl and ethyl, and G is selected from the group consisting of H, halogen, phenyl and substituted phenyl, and a moiety of the formula —(CH$_2$—CR'R'G')$_n$— where R' and n are as defined above and G' is selected from the group consisting of oxygen, sulfur and NR'; Z is selected from the group consisting of H, methyl, phenyl, nitrophenyl, aminophenyl, and when A is an alkylene group or a moiety of the formula —(CH$_2$—CR'G)$_n$—, Z is also selected from the group consisting of —OH, —SH, —NHR", —NR"$_2$, —C(O)OH, —C(O)OR", —C(O)NH$_2$, —C(O)NH—NH$_2$, —C(O)NHR", —C(O)NR"$_2$ and —OR'" where R" is independently alkyl of from 1 to 4 carbon atoms and R'" is an alkenyl of from 3 to 10 carbon atoms.

In one embodiment, the aglycon can be selected to link the oligosaccharides described herein to a solid support and when so selected, the aglycon functions as a chemical linker. Such solid support bound oligosaccharides can be used to isolate glucosidase I. When so employed, the linkers are bifunctional with one functional group (e.g., —OH or —NH$_2$) covalently linking the aglycon to the oligosaccharide and the other functional group covalently linking the aglycon to the solid supports. Examples of such other functional groups on bifunctional linkers are well known in the art. Specific examples of chemical linkers linked to oligosaccharides include —OC$_6$H$_4$pNO$_2$, —OCH$_2$CH$_2$SCH$_2$CO$_2$CH$_3$, —OCH$_2$CH$_2$SC$_6$H$_4$—pNH$_2$, —O(CH$_2$)$_6$NHCOCF$_3$, —CH$_2$CH=CH$_2$, —OCH$_2$CH$_2$NHC(O)(CH$_4$)$_4$CO$_2$CH$_3$, —(CH$_2$)$_8$COOCH$_3$, —(CH$_2$CH$_2$O)$_2$CH$_2$CH=CH$_2$, —O(CH$_2$)$_3$S(CH$_2$)$_2$NH$_2$, —(CH$_2$)$_5$OCH$_2$CH=CH$_2$, and —(CH$_2$)$_8$CH$_2$OH.

Certain of these linkers carry "masked" functional groups which permits demasking at the appropriate point in the synthesis. For example, with —OC$_6$H$_4$pNO$_2$, the nitro group is reduced to a functional amino group by conventional methods thereby demasking this functional group. Likewise, with —O(CH$_2$)$_6$NHCOCF$_3$, the trifluoroacetamido protecting group can be removed unmasking the primary amino group which can then be used for coupling. Allyl aglycons can be derivatized in the presence of 2-aminoethanethiol to provide for an aglycon —OCH$_2$CH$_2$CH$_2$SCH$_2$CH$_2$NH$_2$ which can be coupled to the solid support via the free amino group.

The selection of a particular chemical linker is a matter of convenience rather than of preference.

The chemical linker is sometimes referred to herein as the "aglycon". Consequently, the term "chemical linker" and "aglycon" are often interchanged. However, it is understood that the term "chemical linker" is a subset of aglycons because not all aglycons carry bifunctional groups permitting them to be covalently bound to a solid support. On the other hand, oligosaccharides with aglycons derived from a monofunctional hydrophobic group (e.g., HO(CH$_2$)$_{12}$CH$_3$) can be used to separate glucosidases from a solution containing such glucosidases and the resulting adduct can then be recovered, for example, by incorporation into a lipisome advantageously using this hydrophobic group.

Preferred aglycons have from 1 to 20 carbon atoms and more preferably 1 to 10 carbon atoms. Particularly preferred aglycons include hydrophobic aglycons having 6–20 carbon atoms which can enhance the uptake and release as well as cellular distribution of the oligosaccharides in vivo.[37,39]

The term "protecting group" or "blocking group" refers to any group which when bound to one or more hydroxyl or amino groups of the oligosaccharide prevents reactions from occurring at these hydroxyl or amino groups and which protecting group can be removed by conventional chemical or enzymatic steps to reestablish the hydroxyl group or amino group. The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced either enzymatically or chemically onto a hydroxyl functionality and later selectively removed either by enzymatic or chemical methods in mild conditions compatible with the nature of the product. Preferred removable amino blocking groups include conventional substituents such as t-butoxycarbonyl (t-BOC), benzyloxycarbonyl (CBZ), and the like.

In some embodiments, one blocking group is selected to be differentially removed from another blocking group. Such differential removal refers to the fact that the removal conditions for a first blocking group have little effect on the other blocking group which remains intact after removal of the first blocking group. For example, a hydroxyl group blocked with a benzyl protecting group can be differentially removed from a hydroxyl group blocked with an acetyl blocking group since the hydrogenation conditions used to remove the benzyl protecting will have little effect on the acetyl blocking group.

The term "modified kojibioside α-glucosidase I inhibitors" refers to modified kojibiosides which duplicate the inhibitory action of existing α-glucosidase I inhibitors, preferably with lower toxicity, greater specificity and/or with superior binding capability. In this regard, the work of Lemieux and co-workers[27-30] has demonstrated that specific hydroxy groups are required for the binding of carbohydrates to protein, whereas other hydroxy groups do not play a major role in the recognition process, but merely contribute to the overall strength of binding to the protein.

The term "intermediate useful in the synthesis of modified kojibioside α-glucosidase I inhibitors" refers to those modified kojibiosides which are converted to α-glucosidase I inhibitors by reactions and reaction schemes within the skill of the art.

Methodology

Chemical methods for the synthesis of the oligosaccharides described herein are known in the art. These oligosaccharides are generally assembled using suitably protected individual monosaccharides and suitably protected individual disaccharides intermediates.

The specific methods employed are generally adapted and optimized for each individual structure to be synthesized. In general, the chemical synthesis of all or part of these oligosaccharide first involves formation of a glycosidic linkage on the anomeric carbon atom of the reducing sugar. Specifically, an appropriately protected form of a naturally occurring or of a chemically modified glucose structure (the glycosyl donor) is selectively modified at the anomeric center of the reducing unit so as to introduce a leaving group comprising halides, trichloroacetimidate, acetyl, thioglycoside, etc. The donor is then reacted under catalytic conditions well known in the art with an aglycon or an appropriate form of a carbohydrate acceptor which possess one free hydroxyl or primary/secondary amino group at the position where the glycosidic linkage is to be established. A large variety of aglycon moieties are known in the art and can be attached with the proper configuration to the anomeric center of the reducing unit. Appropriate use of compatible blocking groups, well known in the art of carbohydrate synthesis, will allow selective modification of the synthesized structures or the further attachment of additional sugar units or sugar blocks to the acceptor structures.

After formation of the glycosidic linkage, the saccharide glycoside can be used to effect coupling of additional saccharide unit(s) or chemically modified at selected positions or, after conventional deprotection, used in an enzymatic synthesis. In general, chemical coupling of a naturally occurring or chemically modified saccharide unit to the saccharide glycoside is accomplished by employing established chemistry well documented in the literature. See, for example, Okamoto et al.[40], Abbas et al.[41], Paulsen[42], Schmidt[43], Fugedi et al.[44], Kameyama et al.[45] and Ratcliffe, et al.[46]

In the same manner, an pseudo sugar containing a —NH— in the pyranose sugar structure can be introduced in the reducing sugar end of the oligosaccharide merely by use of suitable blocking groups well known in the art.

In one preferred embodiment for the synthesis of oligosaccharide glycosides, a convenient synthetic blocked disaccharide intermediate, 8-methoxycarbonyloctyl-3-O-acetyl 4,6-O-benzylidene-2-O-(6-O-acetyl-2,3,4-tri-O-benzyl-α-D-glucopyranosyl)-α-D-glucopyranoside 8 which can be used to synthesize modified analogues of kojibiose. Removal of acetyl groups yields modifications at the 3 and 6' positions of kojibioside while removal of the 4,6-O-benzylidene group provides for modification at the 4 and 6 positions. Some of the modifications (which are base sensitive) can also be achieved by blocking the 3, 6' diol disaccharide by a benzyl group followed by removal of 4,6-O-benzylidene to provide modification at the 4 and 6 position of the compound (compounds 38–43 of FIG. 3). Modification at the non-reducing terminal sugar involves separate glycosylations of premodified halides (chlorides or bromides—compounds 65 to 79 of FIG. 4) with suitably protected alcohol under standard glycosylation conditions.

Figure 2:
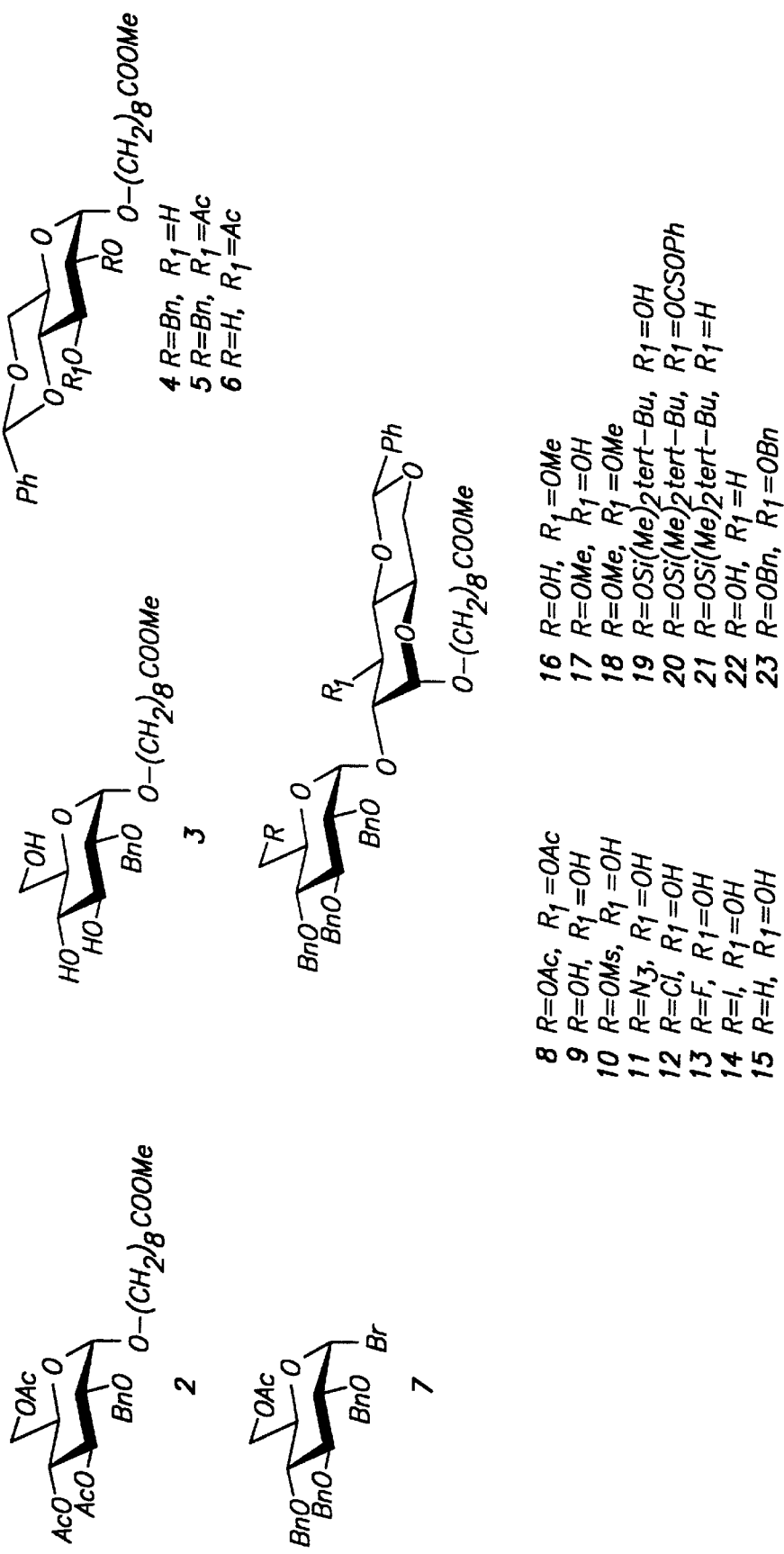

The figures and examples below elaborate chemical synthetic schemes for the preparation of modified kojibiosides of the present invention. Referring to FIG. 2, key disaccharide intermediate 8 is made by a procedure making use of the ready availability of the protected D-glucose derivatives 6 and 7. Deacetylation of known protected monosaccharide 2 with sodium methoxide in methanol provided 3 which was converted into its 4,6-O-benzylidene derivative 4 followed by acetylation to provide 5 and selective hydrogenation provided 6. Coupling of 6 and 7 in the presence of silver trifluoromethanesulfonate, 2,4,6-trimethylpyridine and molecular sieves 4A in dry dichloromethane produced disaccharide 8.

Compounds 44–54 were prepared from a common O-α-D-glucopyranosyl-α-D-glucopyranoside disaccharide precursor 8 which was protected in a manner that allowed the liberation of both acetyl groups to provide diol 9, that was converted selectively into its 6-O-methanesulfonyl derivative 10. Displacement of mesityl group by sodium azide, tetrabutylammonium chloride, tetrabutylammonium iodide provided blocked 6'-azido 11, 6'-chloro 12, 6'-fluoro 13 and 6'-iodo 14 disaccharides. 6'-iodo 14 disaccharide was reduced using tributylstannane and 2,2'-azobis (isobutyronitrile) to give the 6'-deoxy derivative 15.

Diol 9 was also utilized for the synthesis of 3-O-methyl 16, 6'-O-methyl 17 and 3,6'-di-O-methyl 18 disaccharides by methylation at –5° to –10° C. In order to achieve 3-deoxy disaccharide, compound 9 was selectively protected by tert-butyldimethyl silyl group to provide 19, treated with phenyl chlorothiononcarbonate to give 20, which was reduced exactly as described for the preparation of 15 to give 21. Tert butyldimethylsilyl group of 21 was removed by treatment with 80% aqueous $CH_3COOH$ to give compound 22. Hydrogenation of 9, 11, 12, 13, 15, 16, 17, 18 and 22 over 5% palladium-on-carbon followed by chromatography on BioGel P-2 and lyophilization gave the final compounds 44, 47, 48, 49, 50, 51, 52, 53 and 54. Compound 10 was hydrogenated as described above to provide 45. 6'-azido derivative was synthesized by displacing 6'-O-methanesulfonyl compound 45 by sodium azide to provide 46.

Benzylidene group of diacetate precursor 8 was removed by treatment with 80% aqueous $CH_3COOH$ to provide the diol 24, which was converted into its 6-O-methanesulfonyl derivative 25. Displacement of mesityl group by tetrabutylammonium azide, tetrabutylammonium chloride tetrabutylammonium iodide provided compounds 26, 27 and 28. Reduction of 6-iodo derivative as described for the preparation of 15 gave 29. Diol 24 was selectively converted into its 6-O-tert butylmethylsilyl derivative 30, treated with phenylchlorothionocarbonate to give 31, reduction yielded 32 followed by removal of acetyl groups provided 33. Deacetylation of 26, 27 and 29 with sodium methoxide in methanol provided compounds 34, 35 and 36. Removal of tert-butyldimethylsilyl group from 33 gave 37. Diol 9 was benzylated with sodium hydride in dimethylformamide at −5° C. to provide compound 23 which was treated with 80% aqueous $CH_3COOH$ to give diol 38. Selective mesylation of 38 with methanesulfonylchloride in pyridine at −20° C. gave 39 which was displaced by tetrabutylammonium fluoride to give 40 as a 6-fluoro disaccharide. Diol 38 was also treated with methyl iodide in dimethylformamide at −5° to −10° C. to give 4-O-methyl 41, 6-O-methyl 42 and 4,6 di-O-methyl derivative 43. Hydrogenation of 34, 35, 36, 37, 40, 41, 42 and 43 over 5% palladium-on-carbon followed by chromatography on BioGel P-2 and lyophilization gave the final compounds 57, 58, 60, 64, 59, 61, 62 and 63 respectively. 6-azido disaccharide was achieved by hydrogenation of 39 to provide 55 followed by displacement of mesityl group by sodium azide to give 56.

The synthesis of compounds 65 to 79 is described in detail in the examples below. Specifically, 2-deoxy-tetra-O-benzyl-α,β-glucopyranose derivatives 70, 71 were synthesized by treatment of 2-deoxy-tetra-O-acetyl-α,β-glucopyranose derivatives (68, 69) with benzylmercaptan using boron-trifluoroetherate as a catalyst to provided 70, 71 followed by deacetylation to give 72, 73 and benzylation with benzyl bromide and sodium hydride in dimethylformamide to give 74,75.

Coupling of 65, 67, 76, 77, 78, 79 and 96 with 6 in the presence of silver trifluoromethanesulfonate, 2,4,6-trimethylpyridine, and molecular sieves 4A in dry dichloromethane produced disaccharides 80, 84, 88, 90, 92, 94, and 97. Compound 86 was synthesized by reaction of 6 with thioglycoside mixture 74, 75 under copper bromide—DMF catalyzed reaction condition[34]. Coupling of 66 with 6 using mercuric bromide and mercuric cyanide provided disaccharide 82. Deacetylation of 80, 82, 84, 86, 88, 90, 92, 94 and 97 with sodium methoxide in methanol provided compounds 81, 83, 85, 87, 89, 91, 93, 95 and 98 which was hydrogenated with 5% palladium-on-carbon to give compounds 99, 101–108. Compound 83 was treated with 80% aqueous $CH_3COOH$ for 20 hours at room temperature to provide compound 100.

Other analogues of kojibiose included within the scope of this invention include, by way of example, homonojirimycin-amino-glucose, 1,5-trans-(c)-glucopyransoyl-glucose, methyl-2-O-(1,5-trans-(C)-glucopyransoyl)-α-D-glucopyranoside, the synthesis of each of which is illustrated in the examples below.

Utility

The oligosaccharides of formula V, VI and IX–XIII possess glycosidase inhibition and, in particular, glycosidase I inhibition, and therefore are useful as anti-viral agents and in the treatment of diabetes mellitus and obesity. The anti-viral activity of these oligosaccharides are particular suited for the treatment of human immunodeficiency virus type 1, (HIV-1), where administration to a cell infected with this virus results in diminished production of infectious particles and reduces the cytopathic effects caused by this virus.

Such oligosaccharides are effective as anti-viral agents in mammals when administered at a dosage range of from about 0.5 mg to about 50 mg/kg of body weight, and preferably from about 5 to about 20 mg/kg of body weight. The specific dose employed is regulated by the particular virus being treated as well as by the judgment of the attending clinician depending upon factors such as the severity of the viral infection, the age and general condition of the patient, and the like.

The glycosidase inhibition properties of the oligosaccharides of formula V, VI and IX–XIII can also be employed in the dietary management of carbohydrate-dependent metabolic disorders such as diabetes, obesity, hyperglycemia and hyperlipemia by inhibiting in vivo the metabolism of carbohydrates and, when so used, are typically administered to the mammal at a dosage range of from about 0.5 mg to about 50 mg/kg of body weight, and preferably from about 5 to about 20 mg/kg of body weight. The specific dose employed is regulated by the particular condition being treated as well as by the judgment of the attending clinician depending upon factors such as the severity of the condition, the age and general condition of the patient, and the like.

Administration of these oligosaccharides to the mammalian patient is typically achieved by use of a pharmaceutical composition. Such pharmaceutical compositions are formulated for oral, parenteral, intranasal, intrapulmonary, transdermal and intravenous administration and comprise a pharmaceutically acceptable excipient and from about 1 to 95 weight percent of an oligosaccharide of formula V, VI and IX–XIII or a pharmaceutically acceptable salt thereof.

The glycosidase inhibitors of formula V, VI and IX–XIII can also be used for diagnostic/medicinal purposes to evaluate the pathology of viral infections. Specifically, the glycosidase inhibitors can be used to determine the effect of surface glycans on viral particles by interferring with normal glycan biosyntheses thereby presenting a viral particle having a structural defect in the surface glycans. The effect of the structural defect (e.g., on the ability of the viral particle to proliferate and/or to infect a target cell) can be evaluated.

Likewise, the glycosidase inhibitors of formula V, VI and IX–XIII, by virtue of their tight binding to the complementary glycosidases, can be used to recover such complementary glycosidases from a solution containing such glycosidases. For example, in one embodiment, the glycosidase inhibitor is covalently attached to a solid support via an aglycon linking arm (linker) and a solution comprising the complementary glycosidase is passed over the solid support thereby binding this glycosidase to the immobilized glycosidase inhibitor. See, for example, Bause et al.[49]

Oligosaccharides of formulas I–IV, VII and VIII define intermediates useful in the preparation of oligosaccharides of formula V, VI and IX through XIII.

EXAMPLES

The following examples are offered to illustrate this invention and are not to be construed in any way to limit the scope of the invention. Unless otherwise stated, all temperatures are Celsius. In the examples, unless otherwise noted, the abbreviations employed have their generally accepted meaning:

ax=axial
bs=broad singlet
d=doublet
dd=doublet of doublets
ddd=doublet of doublets of doublets
eq=equatorial
gem=indicating attachment to some atom
g=gram h=hour
H-n.m.r.=proton nuclear magnetic resonance
Hz=Hertz
i.r.=infra-red
kg=kilogram
L=liter
mg=milligram
mL=milliliter
mmol=millimole
q=quartet
s=singlet
t=triplet
μL=microliter
μm=micron
Bio-Gel P2 (200–400 mesh)

Anberlite IR-120 (H$^+$ form) cotton exchange reach available from Rohm & Haas, Philadelphia, Penn.

Example 1

Synthesis of 8-methoxycarbonyloctyl 2-O-benzyl-4, 6-O-benzylidene-α-D-glucopyranoside 4

Compound 2 (3 g, 5.30 mmol) was dissolved in dry methanol (10 mL) containing a trace of sodium methoxide (0.01M) and kept for 15 hours at room temperature. Neutralization with Amberlite IR-120 (H$^+$) cation exchange resin, resin removal and solvent evaporation left a white foam 3 (2 g, 85.8%) which was directly dissolved in acetonitrile (10 mL) and benzaldehyde dimethyl acetal (2 mL) and p-toluene sulfonic acid (0.3 g) were added. The reaction mixture was stirred for 1 hour at room temperature and neutralized with triethylamine. Solvent was evaporated and the residue was purified by chromatography on silica gel (hexane:ethyl acetate; 3:1) as eluant to give 4 (2 g, 71.5%) as a solid; $[\alpha]_D$+52° (c 0.88, chloroform). $^1$H-n.m.r. (CDCl$_3$): δ=5.52(s, 1H, C$_6$H$_5$, C$\underline{H}$O$_2$), 4.74(d, 1H, J$_{gem}$ 12.0 Hz, C$_6$H$_5$C$\underline{H}$H), 4.73(d, 1H, J$_{1,2}$ 4.0 Hz, H-1), 4.65(d, 1H, J$_{gem}$ 12.0 Hz, C$_6$H$_5$CH$\underline{H}$), 4.22(dd, 1H, J$_{2,3}$ 10.0 Hz, H-2), 3.65(s, 1H, OCH$_3$), 2.76(d, 1H, OH,D$_2$O exchangeable), 2.28 (t, 2H, J 7.5 Hz, C$\underline{H}_2$COO).

Anal. Calc. for C$_{30}$H$_{40}$O$_8$: C, 68.16; H, 7.63. Found: C, 67.91; H, 7.64.

Example 2

Synthesis of 8-Methoxycarbonyloctyl 3-O-acetyl-2-O-benzyl-4,6-O-benzylidene-α-D-glucopyranoside (5)

Compound 4 (1.5 g, 2.84 mmol) was dissolved in dry pyridine (5 mL) and then added to it was acetic anhydride (5 mL) at room temperature. After stirring for 15 hours, it was evaporated, washed with water (2×50 mL), ice cold 5% HCl (2×50 mL), ice cold saturate sodium hydrogen carbonate (2×50 mL) and with water (2×50 mL) before concentration to a syrup, which was purified by chromatography on silica gel (hexane:ethyl acetate; 3:1) as eluant to give 5 (1.55 g, 95.7%); $[\alpha]_D$+39.8° (c 0.63, chloroform). $^1$H-n.m.r. (CDCl$_3$): δ 5.57(t, 1H, J$_{2,3}$=J$_{3,4}$ 10.0 Hz, H-3), 5.43(s, 1H, C$_6$H$_5$C$\underline{H}$O$_2$), 4.79(d, 1H, J$_{1,2}$ 3.5 Hz, H-1), 4.60(ABq, 2H, J$_{gem}$ 12.5 Hz, C$_6$H$_5$C$\underline{H}_2$), 4.22(d, 1H, H-2), 3.60(s, 3H, OCH$_3$), 2.25(t, 2H, J 7.5 Hz, C$\underline{H}_2$COO), 2.01(s, 3H, Ac).

Anal. Calc. for C$_{32}$H$_{42}$O$_9$: C, 67.35; H, 7.42. Found: C, 67.25; H, 7.42.

Example 3

Synthesis of 8-Methoxycarbonyloctyl 3-O-acetyl-4, 6-O-benzylidene-α-D-glucopyranoside (6)

Compound 5 (1.5 g, 2.63 mmol) was dissolved in 98% ethanol (5 mL) and hydrogenated over 5% palladium on charcoal (500 mg) at atmospheric pressure for 5 hours. The catalyst was removed by filtration and after solvent evaporation, the residue was purified by chromatography on silica gel using (hexane:ethyl acetate; 3:1) as eluant. Pure compound 6 (800 mg, 63.3%) obtained as a white solid; $[\alpha]_D$+52.7° (c 0.15, chloroform). $^1$H-n.m.r. (CDCl$_3$): δ 5.50 (s, 1H, C$_6$H$_5$C$\underline{H}$O$_2$), 5.32(t, J$_{2,3}$=J$_{3,4}$ 10.0 Hz, H-3), 4.87(d, 1H, J$_{1,2}$ 4.0 Hz, H-1), 4.27 (dd, 1H, H-2), 3.62(s, 3H, OCH$_3$), 2.39(d, 1H, J 12.0 Hz, OH, D$_2$O exchangeable), 2.28(t, 2H, J 7.5 Hz, C$\underline{H}_2$COO), 2.10(s, 3H, Ac).

Anal. Calc. for C$_{25}$H$_{36}$O$_9$: C, 62.48; H, 7.55. Found: C, 62.45; H, 7.59.

Example 4

Synthesis of 8-Methoxycarbonyloctyl 3-O-acetyl-4, 6-O-benzylidene-2-O-(6-O-acetyl-2,3,4-tri-O-benzyl-α-D-glucopyranosyl)-α-D-glucopyranoside (8)

A solution of known bromide 7 (6.38 g, 12.5 mmol) was added dropwise over 0.5 hours to a mixture of 6 (3 g, 6.24 mmol), sym-collidine (1.65 mL, 12.5 mmol), silver trifluoromethane sulfonate (3.12 g, 12.5 mmol) and pulverized 4A molecular sieves (6 g) stirring in dichloromethane (25 mL) at 0° C. After 5 hours, dichloromethane (100 mL) was added and the sieves were removed by filtration and washed with more dichloromethane (100 mL). Solvent was evaporated and the residual syrup was purified by chromatography on silica gel (hexane: ethyl acetate; 3:1) as eluant to give compound 8 (4.5 g, 75.5%) as a syrup $[\alpha]_D$+81.5° (c 0.34, chloroform). $^1$H-n.m.r. (CDCl$_3$): δ 5.57(t, 1H, J$_{2,3}$=J$_{3,4}$ 10.0 Hz, H-3), 5.46(s, 1H, C$_6$H$_5$C$\underline{H}$O$_2$), 4.97(d, 1H, J$_{1',2'}$ 3.8 Hz, H-1'), 4.88(d, 1H, J$_{1,2}$ 3.8 Hz, H-1), 3.62(s, 3H, OCH$_3$), 2.25(t, 2H, J 7.5 Hz, C$\underline{H}_2$COO), 2.02, 2.05(s, 3H each, 2×Ac).

Anal. Calc. for C$_{54}$H$_{66}$O$_{15}$: C, 67.91; H, 6.97. Found: C, 67.89; H, 6.90.

Example 5

Synthesis of 8-Methoxycarbonyloctyl 4,6-O-benzylidene-2-O-(2,3,4-tri-O-benzyl-α-D-glucopyranosyl)-α-D-glucopyranoside (9)

Treatment of 8 (4.2 g, 4.40 mmol) with methanolic sodium methoxide as described for the preparation of 3, provided 9 (3.2 g, 83.5%) as a syrup, $[\alpha]_D$+85.4° (c 0.56, chloroform). $^1$H-n.m.r. (CDCl$_3$): δ 5.46(s, 1H, C$_6$H$_5$C$\underline{H}$O$_2$), 4.92(d, 1H, J$_{1',2'}$ 3.8 Hz, H-1'), 4.89(d, 1H, J$_{1,2}$ 3.8 Hz, H-1), 3.63(s, 3H, OCH$_3$), 2.24(t, 2H, J 7.5 Hz, C$\underline{H}_2$COO), 2.12, 2.0(m, 2H, 2×OH, D$_2$O exchangeable).

Anal. Calc. for C$_{50}$H$_{62}$O$_{13}$: C, 68.94; H, 7.18. Found: C, 68.68; H, 7.11.

Example 6

Synthesis of 8-Methoxycarbonyloctyl 4,6-O-benzylidene-2-O-(2,3,4-tri-O-benzyl-6-O-methane sulfonyl-α-D-glucopyranosyl)-α-D-glucopyranoside (10)

Methanesulfonyl chloride (533 μL, 6.89 mmol) was added to a stirred solution of diol 9 (3.0 g, 3.44 mmol) in dry pyridine (25 mL) at −20° C. After 1 hour, the reaction mixture was poured into aqueous sodium hydrogencarbonate and extracted with dichloromethane (100 mL). The organic layer was washed twice with water (2×100 mL), dried with sodium sulfate and evaporated. The crude product was purified by chromatography on silica gel (hexane: ethyl acetate; 3:1) as eluant to give 10 (2.75 g, 80.6%) as a powder; $[\alpha]_D$+89° (c 0.13, chloroform). $^1$H-n.m.r. (CDCl$_3$): δ 5.54(s, 1H, C$_6$H$_5$C$\underline{H}$O$_2$), 4.98(d, 1H, J$_{1',2'}$ 3.8 Hz, H-1'), 4.92(d, 1H, J$_{1,2}$ 3.8 Hz, H-1), 3.64(s, 3H, OCH$_3$), 3.0(s, 3H, CH$_3$SO$_2$), 2.27(t, 2H, J 7.5 Hz, C$\underline{H}_2$COO).

Anal. Calc. for C$_{53}$H$_{66}$O$_{16}$S: C, 64.12; H, 6.71; S, 3.24. Found: C, 63.82; H, 6.82; S, 3.11.

Example 7

Synthesis of 8-Methoxycarbonyloctyl 4,6-O-benzylidene-2-O-(6-azido-2,3,4-tri-O-benzyl-α-D-glucopyranosyl)-α-D-glucopyranoside (11)

A mixture of 10 (150 mg, 0.15 mmol) and sodium azide (49.2 mg, 0.76 mmol) in DMF (2 mL) was heated with stirring for 15 hours at 70° C. It was diluted with dichloromethane (50 mL), washed with water (2×50 mL) followed by drying (Na$_2$SO$_4$) and evaporation. The resulting product was purified on a column of silica gel (hexane:ethyl acetate; 5:1) as eluant to give the title compound 11 (118.5 mg, 87.4%) as a syrup; $[\alpha]_D$+72.9° (c 0.16, chloroform). $^1$H-n.m.r. (CDCl$_3$): δ 5.57(s, 1H, C$_6$H$_5$C$\underline{H}$O$_2$), 5.02(d, 1H, J$_{1',2'}$ 3.8 Hz, H-1'), 4.93(d, 1H, J$_{1,2}$ 3.8 Hz, H-1), 4.15(dt, 1H, J$_{3,OH}$ 2.0 Hz, J$_{2,3}$=J$_{3,4}$ 10.0 Hz, H-3), 4.05(t, 1H, J$_{2',3'}$=J$_{3',4'}$ 10.0 Hz, H-3'), 3.64(s, 3H, OCH$_3$), 3.05(d, 1H, OH, D$_2$O exchangeable), 2.27(t, 2H, J 7.5 Hz, C$\underline{H}_2$COO).

Anal. Calc. for C$_{50}$H$_{61}$O$_{12}$N$_3$: C, 67.02; H, 6.86; N, 4.69. Found: C, 67.22; H, 6.92; N, 4.61.

Example 8

Synthesis of 8-Methoxycarbonyloctyl 4,6-O-benzylidene-2-O-(6chloro-2,3,4-tri-O-benzyl-α-D-glucopyranosyl)-α-D-glucopyranoside (12)

A solution of 10 (150 mg, 0.15 mmol) and tetrabutylammonium chloride (84.1 mg, 0.30 mmol) in dry benzene (5 mL) was heated at 70° C. for 20 hours. After evaporation, the crude product was chromatographed on a column of silica gel (hexane:ethyl acetate; 5:1) to provide compound 12 (120 mg, 89.2%) as a syrup; $[\alpha]_D$+107.1° (c 0.18, chloroform). $^1$H-n.m.r. (CDCl$_3$): δ 5.58 (s, 1H, C$_6$H$_5$C$\underline{H}$O$_2$), 5.22(d, 1H, J$_{1',2'}$ 3.8 Hz, H-1'), 4.92(d, 1H, J$_{1,2}$ 3.8 Hz, H-1), 4.14(dt, 1H, J$_{3,OH}$ 2.0 Hz, J$_{2,3}$=J$_{3,4}$ 10.0 Hz, H-3), 4.07(t, 1H, J$_{2',3'}$=J$_{3',4'}$ 10.0 Hz, H-3'), 3.62(s, 3H, OCH$_3$), 3.50(dd, 1H, H-4), 3.15(d, 1H, OH, D$_2$O exchangeable), 2.25(t, 2H, C$\underline{H}_2$COO).

Anal. Calc. for: C$_{50}$H$_{61}$O$_{12}$Cl: C, 67.51; H, 6.91: Cl, 3.99. Found: C, 67.51; H, 6.91; Cl, 3.99.

Example 9

Synthesis of 8-Methoxycarbonyloctyl 4,6-O-benzylidene-2-O-(6fluoro2,3,4-tri-O-benzyl-α-D-glucopyranosyl)-α-D-glucopyranoside (13)

To a solution of mesylate 10 (180 mg, 0.18 mmol) in acetonitrile (2 mL) was added a solution of tetraethylammonium fluoride hydrate (54.2 mg, 0.36 mmol) in acetonitrile (2 mL) and the mixture was heated under reflux for 3 hours. After evaporation of the solvent, the residue was applied to a column of silica gel (hexane:ethyl acetate; 5:1) to give 13 (102 mg, 64.3%) as a syrup; $[\alpha]_D$+108.6° (c 0.08, chloroform). $^1$H-n.m.r. (CDCl$_3$): δ 5.55(s, 1H, C$_6$H$_5$C$\underline{H}$O$_2$), 4.99(d, 1H, J$_{1',2'}$ 3.8 Hz, H-1'), 4.92(d, 1H, J$_{1,2}$ 3.8 Hz, H-1), 4.47(dt, 1H, J$_{3,OH}$ 2.0 Hz, J$_{2,3}$=J$_{3,4}$ 10.0 Hz, H-3), 3.63(s, 3H, OCH$_3$), 3.10(d, 1H, OH), 2.28(t, 2H, C$\underline{H}_2$COO).

Anal. Calc. for C$_{50}$H$_{61}$O$_{12}$F: C, 68.79; H, 7.04. Found: C, 69.00; H, 7.04.

Example 10

Synthesis of 8-Methoxycarbonyloctyl 4,6-O-benzylidene-2-O-(6-iodo-2,3,4-tri-O-benzyl-α-D-glucopyranosyl)-α-D-glucopyranoside (14)

A solution of 10 (160 mg, 0.16 mmol) and tetrabutylammonium iodide (298 mg, 0.81 mmol) in dry toluene (5 mL) was heated at 70° C. for 20 hours. After evaporation, the crude product was chromatographed on silica gel (hexane:ethyl acetate; 5:1) to provide compound 14 (150 mg, 94.7%) as a syrup; $[\alpha]_D$ 71.4° (c 0.27, chloroform). $^1$H-n.m.r. (CDCl$_3$): δ 5.55(s, 1H, C$_6$H$_5$C$\underline{H}$O$_2$), 5.04(d, 1H, J$_{1',2'}$ 3.8 Hz, H-1'), 4.96(d, 1H, J$_{1,2}$ 3.8 Hz, H-1), 3.65(s, 3H, OCH$_3$), 3.1–2.8 (m, 1H, OH), 2.26(t, 2H, J 7.5 Hz, C$\underline{H}_2$COO).

Anal. Calc. for C$_{50}$H$_{61}$O$_{12}$I: C, 61.22; H, 6.27; I, 12.94. Found: C, 61.04; H, 6.24; I, 12.20.

Example 11

Synthesis of 8-Methoxycarbonyloctyl 4,6-O-benzylidene-2-O-(6-deoxy-2,3,4-tri-O-benzyl-α-D-glucopyranosyl)-α-D-glucopyranoside (15)

A solution of 14 (125 mg, 0.13 mmol) in dry toluene (5 mL) was heated to 80° C. under nitrogen, the 2-2'-azobis (isobutyronitrile) (31.9 mg, 0.19 mmol) was added, followed by tributylstannane (68.8 μL, 0.26 mmol). After 6 hours at 80° C., the mixture was allowed to cool to room temperature and the solvent was evaporated. Column chromatography of the residue on silica gel using (hexane:ethyl acetate; 3:1) as eluant provided 15 (95 mg, 87.2%); $[\alpha]_D$+24° (c 0.23, chloroform). $^1$H-n.m.r. (CDCl$_3$): δ 5.56(s, 1H, C$_6$H$_5$C$\underline{H}$O$_2$), 4.93(d, 1H, J$_{1',2'}$ 3.8 Hz, H-1'), 4.87(d, 1H, J$_{1,2}$ 3.8 Hz, H-1), 3.65(s, 3H, OCH$_3$), 2.25(t, 2H, C$\underline{H}_2$COO), 1.24(d, 3H, J$_{5',6'}$ 7.0 Hz, H-6').

Anal. Calc. for C$_{50}$H$_{62}$O$_{12}$: C, 70.23; H, 7.31. Found: C, 70.18; H, 7.11.

Examples 12

Synthesis of 8-Methoxycarbonyloctyl 4,6-O-benzylidene-3-O-methyl-2-O-(2,3,4-tri-O-benzyl-α-D-glucopyranosyl)-α-D-glucopyranoside (16)

Synthesis of 8-Methoxycarbonyloctyl 4,6-O-benzylidene-2-O-(6-O-methyl-2,3,4-tri-O-benzyl-α-D-glucopyranosyl)-α-D-glucopyranoside (17); and Synthesis of 8-Methoxycarbonyloctyl 4,6-O-benzylidene-3-O-methyl-2-O-(6-O-methyl-2,3,4-tri-O-benzyl-α-D-glucopyranosyl)-α-D-glucopyranoside (18)

A solution of compound 9 (250 mg, 0.29 mmol) in DMF (5 mL) was added dropwise at −10° C., to a solution of sodium hydride (17.2 mg of 50% dispersion in oil) in DMF (5 mL). After 0.5 hours, methyl iodide (35.7 μL, 0.57 mmol) was added dropwise and the reaction mixture was stirred for 5 hours at −5° to −10° C. After dilution with dichloromethane (50 mL), the mixture was poured into ice-water and washed with ice-cold water (3×50 mL) before concentration to a syrup which was purified by chromatography on silica gel using (hexane:ethyl acetate; 3:1) as eluant to provide:

16 (75 mg, 29.5%); $[\alpha]_D$+64.3° (c 0.34, chloroform). $^1$H-n.m.r. (CDCl$_3$): δ 5.57(s, 1H, C$_6$H$_5$C$\underline{H}$O$_2$), 4.93(d, 1H, J$_{1',2'}$ 3.8 Hz, H-1'), 4.91(d, 1H, J$_{1,2}$ 3.8 Hz, H-1), 3.63(s, 3H, OCH$_3$), 3.64(s, 3H, OCH$_3$), 2.27(t, 2H, J 7.5 Hz, C$\underline{H}_2$COO).

Anal. Calc. for C$_{51}$H$_{64}$O$_{13}$: C, 69.21; H, 7.29. Found: C, 69.11; H, 7.25.

17 (85 mg, 33.4%); $[\alpha]_D$+84.8° (c 0.40, chloroform). $^1$H-n.m.r. (CDCl$_3$): δ 5.57(s, 1H, C$_6$H$_5$C$\underline{H}$O$_2$), 4.95(d, 1H, J$_{1',2'}$ 3.8 Hz, H-1'), 4.92(d, 1H, J$_{1,2}$ 3.8 Hz, H-1), 3.62(s, 3H, OCH$_3$), 3.60(s, 3H, OCH$_3$), 2.24(t, 2H, J 7.5 Hz, C$\underline{H}_2$COO).

Anal. Calc. for C$_{51}$H$_{64}$O$_{13}$: C, 69.21; H, 7.29. Found: C, 69.33; H, 7.11.

and 18 (35 mg, 13.8%); $[\alpha]_D$+72° (c 0.26, chloroform). $^1$H-n.m.r. (CDCl$_3$): δ 5.57(s, 1H, C$_6$H$_5$C$\underline{H}$O$_2$), 4.97(d, 1H, J$_{1',2'}$ 3.8 Hz, H-1'), 4.94(d, 1H, J$_{1,2}$ 3.8 Hz, H-1), 3.64(s, 3H, OCH$_3$), 3.63(s, 3H, OCH$_3$), 2.27(t, 2H, J 7.5 Hz, C$\underline{H}_2$COO).

Anal. Calc. for C$_{52}$H$_{66}$O$_{13}$: C, 69.47; H, 7.40. Found: C, 69.27; H, 7.39.

Example 13

Synthesis of 8-Methoxycarbonyloctyl 4,6-O-benzylidene-2-O-(2,3,4-tri-O-benzyl-6-O-tert-butyldimethylsilyl-α-D-glucopyranosyl)-α-D-glucopyranoside (19)

A solution of the diol 9 (220 mg, 0.25 mmol) and tert-butyl-dimethylsilyl chloride (76.1 mg, 0.51 mmol) in dry pyridine (10 mL) was stirred for 15 hours. The solution was extracted with dichloromethane and taken to dryness. Chromatography of the residue using (hexane:ethyl acetate; 5:1) as eluant provided 19 (210 mg, 84.4%) as a syrup; $[\alpha]_D$+76.9° (c 0.45, chloroform). $^1$H-n.m.r. (CDCl$_3$): δ 5.50 (s, 1H, C$_6$H$_5$C$\underline{H}$O$_2$), 4.90(d, 1H, J$_{1',2'}$ 3.8 Hz, H-1'), 4.87(d, 1H, J$_{1,2}$ 3.8 Hz, H-1), 3.61(s, 3H, OCH$_3$), 0.83(s, 9H, (CH$_3$)$_3$).

Anal. Calc. for C$_{56}$H$_{76}$O$_{13}$Si: C, 68.26; H, 7.78. Found: C, 68.06, H, 7.72.

Example 14

Synthesis of 8-Methoxycarbonyloctyl 4,6-O-benzylidene-3-O-phenoxythiocarbonyl-2-O-(2,3,4-tri-O-benzyl-6O-tert-butyldimethylsilyl-α-D-glucopyranosyl)-α-D-glucopyranoside (20)

A mixture of 19 (180 mg, 0.18 mmol), 4-dimethylaminopyridine (44.6 mg, 0.37 mmol) and phenyl chlorothionocarbonate (75.8 μL, 0.55 mmol) in dry acetonitrile (10 mL) was heated under reflux for 5 hours, and then left for 16 hours at room temperature. The mixture was diluted with dichloromethane (50 mL), and washed sequentially with ice cold 0.5M hydrochloric acid (50 mL) and water (50 mL). Evaporation of the solvent and chromatographic purification of the residue using (hexane:ethyl acetate; 9:1) as eluant gave 20 (185 mg, 90.3%) as a syrup; $[\alpha]_D$+76.9° (c 0.45, chloroform). $^1$H-n.m.r. (CDCl$_3$): δ 6.11 (t, 1H, J$_{2,3}$=J$_{3,4}$ 10.5 Hz, H-3), 5.50(s, 1H, C$_6$H$_5$C$\underline{H}$O$_2$), 5.02(d, 1H, J$_{1',2'}$ 3.8 Hz, H-1'), 4.93(d, 1H, J$_{1,2}$ 3.8 Hz, H-1), 3.62(s, 3H, OCH$_3$), 2.22(t, 2H, J 7.5 Hz, C$\underline{H}_2$COO), 0.83(s, 9H, (CH$_3$)$_3$).

Anal. Calc. for C$_{63}$H$_{80}$O$_{14}$SSi: C, 67.47; H, 7.19; S, 2.86. Found: C, 67.33; H, 7.11; S, 2.77.

Example 15

Synthesis of 8-Methoxycarbonyloctyl 4,6-O-benzylidene-3-deoxy-2-O-(2,3,4-tri-O-benzyl-6O-tert-butyldimethylsilyl-α-D-glucopyranosyl)-α-D-ribohexopyranoside (21)

A solution of 20 (160 mg, 0.14 mmol) in dry toluene (5 mL) was heated to 80° C. under nitrogen, and the 2,2'-azobis (isobutyronitrile) (44.8 mg, 0.27 mmol) was added, followed by tributylstannane (72.6 μL, 0.27 mmol). After 3 days at 80° C., the mixture was allowed to cool to room temperature and the solvent was evaporated. Column chromatography of the residue (hexane:ethyl acetate; 9:1) provided 21 (110 mg, 79.6%) as a syrup; $[\alpha]_D$+58° (c 0.56, chloroform). $^1$H-n.m.r. (CDCl$_3$): δ 5.47(s, 1H, C$_6$H$_5$C$\underline{H}$O), 4.92(d, 1H, J$_{1',2'}$ 3.8 Hz, H-1'), 4.83(d, 1H, J$_{1,2}$ 3.8 Hz, H-1), 3.61(s, 3H, OCH$_3$), 2.23(t, 2H, J 7.5 Hz, C$\underline{H}_2$COO).

Anal. Calc. for C$_{56}$H$_{76}$O$_{12}$Si: C, 69.39; H, 7.90. Found: C, 69.59, H, 7.81.

Example 16

Synthesis of 8-Methoxycarbonyloctyl 4,6-O-benzylidene-3-O-benzyl-2-O-(2,3,4,6-tetra-O-benzyl-α-D-glucopyranosyl)-α-D-glucopyranoside (23)

Compound 9 (550 mg, 0.63 mmol) was benzylated with sodium hydride (121.2 mg of a 50% dispersion in oil) and benzyl bromide (300.5 μL, 2.53 mmol) in DMF (10 mL) for 5 hours at −5° C. After solvent evaporation, the residue was purified by chromatography on silica gel using (hexane:ethyl acetate; 3:1) as eluant to provide 23 (560 mg, 84.4%) as a syrup; $[\alpha]_D$+63.1° (c 0.36, chloroform). $^1$H-n.m.r. (CDCl$_3$): δ 5.56(s, 1H, C$_6$H$_5$C$\underline{H}$O$_2$), 5.08(d, 1H, J$_{1',2'}$ 3.8 Hz, H-1'), 5.03(d, 1H, J$_{1,2}$ 3.8 Hz, H-1), 3.62(s, 3H, OCH$_3$), 2.26(t, 2H, J 7.5 Hz, C$\underline{H}_2$COO).

Anal. Calc. for C$_{64}$H$_{74}$O$_{13}$: C, 73.12; H, 7.10. Found: C, 72.99; H, 6.89.

Example 17

Synthesis of 8-Methoxycarbonyloctyl 3-O-acetyl-2-O-(6-O-acetyl-2,3,4-tri-O-benzyl-α-D-glucopyranosyl)-α-D-glucopyranoside (24)

Compound 8 (1 g, 1.05 mmol) was dissolved in dichloromethane (5 mL) and aqueous 80% acetic acid (200 mL) was added. After stirring the reaction mixture for 20 hours at room temperature, the solvent was evaporated and coevaporated with toluene. The residue was purified by chromatography on silica gel using (hexane:ethyl acetate; 1:1) as eluant. Pure 24 (650 mg, 71.6%) was obtained as a syrup; $[\alpha]_D$+80.6° (c 0.16, chloroform). $^1$H-n.m.r. (CDCl$_3$): δ 5.34(t, 1H, J$_{2,3}$=J$_{3,4}$ 10.0 Hz, H-3), 4.99(d, 1H, J$_{1',2'}$ 3.8 Hz, H-1'), 4.93(d, 1H, J$_{1,2}$ 3.8 Hz, H-1), 3.63(s, 3H, OCH$_3$), 2.27(t, 2H, J 7.5 Hz, C$\underline{H}_2$COO), 2.03 and 2.03(s, 3H each, 2×Ac).

Anal. Calc. for C$_{47}$H$_{62}$O$_{15}$: C, 65.11; H, 7.21. Found: C, 65.00; H, 7.03.

Example 18

Synthesis of 8-Methoxycarbonyloctyl 3-O-acetyl-6O-methanesulfonyl-2-O-(6O-acetyl-2,3,4-tri-O-benzyl-α-D-glucopyranosyl)-α-D-glucopyranoside (25)

Compound 24 (570 mg, 0.66 mmol) was converted into its methane sulfonyl derivative exactly as described for the preparation of 10 to give 25 (530 mg, 85.3%) as a syrup after chromatography on silica gel using (hexane:ethyl acetate; 3:2) as eluant; $[\alpha]_D$+76.6° (c 0.57, chloroform). $^1$H-n.m.r. (CDCl$_3$): δ 5.19(t, 1H, J$_{2,3}$=J$_{3,4}$ 10.0 Hz, H-3), 4.90(d, 1H, J$_{1',2'}$ 3.8 Hz, H-1'), 4.82(d, 1H, J$_{1,2}$ 3.8 Hz, H-1), 3.57(s, 3H, OCH$_3$), 3.00(s, 3H, CH$_3$SO$_2$), 2.23 and 2.03(s, 3H each, 2×Ac).

Anal. Calc. for $C_{48}H_{64}O_{17}S$: C, 61.00; H, 6.83; S, 3.39. Found: C, 60.89; H, 6.72; S, 3.31.

Example 19

Synthesis of 8-Methoxycarbonyloctyl 3-O-acetyl-6-azido-2-O-(6O-acetyl-2,3,4-tri-O-benzyl-α-D-glucopyranosyl)-α-D-glucopyranoside (26)

Compound 25 (125 mg, 0.13 mmol) was converted into its 6-azido derivative exactly as described for the preparation of 11 to give 26 (100 mg, 84.8%) as a syrup after chromatography on silica gel using (hexane:ethyl acetate; 3:1) as eluant; $[\alpha]_D$+72.9° (c 0.16, chloroform). $^1$H-n.m.r. (CDCl$_3$): δ 5.22(t, 1H, $J_{2,3}$=$J_{3,4}$ 10.0 Hz, H-3), 5.0(d, 1H, $J_{1',2'}$ 3.8 Hz, H-1'), 4.92(d, 1H, $J_{1,2}$ 3.8 Hz, H-1), 3.65(s, 3H, OCH$_3$), 2.27(t, 2H, J 7.5 Hz, CH$_2$COO), 2.10 and 2.02(s, 3H each, 2×Ac).

Anal. Calc. for $C_{47}H_{61}O_{14}N_3$: C, 63.28; H, 6.89; N, 4.71. Found: C, 63.10; H, 6.77; N, 4.35.

Example 20

Synthesis of 8-Methoxycarbonyloctyl 3-O-acetyl-6-chloro-2-O-(6O-acetyl-2,3,4-tri-O-benzyl-α-D-glucopyranosyl)-α-D-glucopyranoside (27)

Compound 25 (120 mg, 0.13 mmol) was converted into its 6-chloro derivative exactly as described for the preparation of 12 to give 27 (95 mg, 84.5%) as a syrup after chromatography on silica gel using (hexane:ethyl acetate; 3:1) as eluant; $[\alpha]_D$+118.6° (c 0.07, chloroform). $^1$H-n.m.r. (CDCl$_3$): δ 5.25(t, 1H, $J_{2,3}$=$J_{3,4}$ 10.0 Hz, H-3), 5.02(d, 1H, $J_{1',2'}$ 3.8 Hz, H-1'), 4.90(d, 1H, $J_{1,2}$ 3.8 Hz, H-1), 3.65(s, 3H, OCH$_3$), 2.27(t, 2H, J 7.5 Hz, CH$_2$COO), 2.10 and 2.02(s, 3H each, 2×Ac).

Anal. Calc. for $C_{47}H_{61}O_{14}Cl$: C, 63.75; H, 6.95. Found: C, 63.65; H, 6.83.

Example 21

Synthesis of 8-Methoxycarbonyloctyl 3-O-acetyl-6iodo-2-O-(6-O-acetyl-2,3,4-tri-O-benzyl-α-D-glucopyranosyl)-α-D-glucopyranoside (28)

Compound 25 (135 mg, 0.14 mmol) was converted into its 6-iodo derivative exactly as described for the preparation of 14 to give 28 (120 mg, 86%) as a syrup after chromatography on silica gel using (hexane:ethyl acetate; 3:1); as eluant; $[\alpha]_D$+86.4 (c 0.53, chloroform). $^1$H-n.m.r. (CDCl$_3$): δ 5.27(t, 1H, $J_{2,3}$=$J_{3,4}$ 10.0 Hz, H-3), 4.99(d, 1H, $J_{1',2'}$ 3.8 Hz, H-1'), 4.91(d, 1H, $J_{1,2}$ 3.8 Hz, H-1), 3.65(s, 3H, OCH$_3$), 2.27(t, 2H, J 7.5 Hz, CH$_2$COO), 2.10 and 2.02(s, 3H each, 2×Ac).

Anal. Calc. for $C_{47}H_{61}O_{14}I$: C, 57.78; H, 6.30; I, 12.99. Found: C, 57.37; H, 6.21; I, 12.89.

Example 22

Synthesis of 8-Methoxycarbonyloctyl 3-O-acetyl-6-deoxy-2-O-(6-O-acetyl-2,3,4-tri-O-benzyl-α-D-glucopyranosyl)-α-D-glucopyranoside (29)

Compound 28 (80 mg, 0.08 mmol) was deoxygenated exactly as described for the preparation of 15 to give 29 (62 mg, 87.5%) as a syrup after chromatography on silica gel using (hexane:ethyl acetate; 3:1) as eluant; $[\alpha]_D$+96.20° (c 0.44, chloroform). $^1$H-n.m.r. (CDCl$_3$): δ 5.21(t, 1H, $J_{2,3}$=$J_{3,4}$ 10.0 Hz, H-3), 4.93(d, 1H, $J_{1',2'}$ 3.8 Hz, H-1'), 4.92(d, 1H, $J_{1,2}$ 3.8 Hz, H-1), 3.65(s, 3H, OCH$_3$), 2.83(d, 1H, J 5.5 Hz, OH, D$_2$O exchangeable), 2.26(t, 2H, J 7.5 Hz, CH$_2$COO), 2.1, 2.01(s, 3H each, 2Ac), 1.28(d, 1H, $J_{5,6}$ 7.5 Hz, H-6).

Anal. Calc. for $C_{47}H_{62}O_{14}$: C, 66.33; H, 7.35. Found: C, 66.03; H, 7.31.

Example 23

Synthesis of 8-Methoxycarbonyloctyl 3-O-acetyl-6-O-tert-butyl-dimethylsilyl-2-O-(6-O-acetyl-2,3,4-tri-O-benzyl-α-D-glucopyranosyl)-α-D-glucopyranoside (30)

Diol 24 (350 mg, 0.40 mmol) was converted into its 6-O-tert-butyl dimethylsilyl derivative exactly as described for the preparation of 19 to provide 30 (320 mg, 80.8%) as a syrup after chromatography on silica gel using (hexane:ethyl acetate; 3:1) as eluant; $[\alpha]_D$+22.9° (c 0.23, chloroform). $^1$H-n.m.r. (CDCl$_3$): δ 5.22(t, 1H, $J_{2,3}$=$J_{3,4}$ 10.0 Hz, H-3), 4.87(d, 1H, $J_{1',2'}$ 3.8 Hz, H-1'), 4.83(d, 1H, H-1, $J_{1,2}$ 3.8 Hz, H-1), 3.58(s, 3H, OCH$_3$), 2.21(t, 2H, J 7.5 Hz, CH$_2$COO), 2.03, 1.95(s, 3H each, 2Ac), 0.82(s,9H, CH$_3$).

Anal. Calc. for $C_{53}H_{76}O_{15}Si$: C, 64.82; H, 7.81. Found: C, 64.81; H, 7.51.

Example 24

Synthesis of 8-Methoxycarbonyloctyl 3-O-acetyl-6-O-tert-butyl-dimethylsilyl-4O-phenoxythiocarbonyl-2-O-(6O-acetyl-2,3,4-tri-O-benzyl-α-D-glucopyranosyl)-α-D-glucopyranoside (31)

Compound 30 (250 mg, 0.26 mmol) was converted into its phenoxy thiocarbonyl derivative as described for the preparation of 20 to give 31 (230 mg. 80.8%) as a syrup after chromatography on silica gel using (hexane:ethyl acetate; 3:1) as eluant; $[\alpha]_D$+33° (c 0.25, chloroform). $^1$H-n.m.r. (CDCl$_3$): δ 5.58(dd, 1H, $J_{3,4}$=$J_{4,5}$ 10.0 Hz, H-4), 5.50(t, 1H, H-3), 4.93(d, 1H, $J_{1',2'}$ 3.8 Hz, H-1), 4.83(d, 1H, $J_{1,2}$ 3.8 Hz, H-1'), 3.57(s, 3H, OCH$_3$), 2.19(t, 2H, J 7.5 Hz, CH$_2$COO), 1.95, 1.94(s, 3H each, 2Ac).

Anal. Calc. for $C_{60}H_{80}O_{16}SSi$: C, 64.49; H, 7.22; S, 2.87. Found: C, 64.13; H, 7.11; S, 2.50.

Example 25

Synthesis of 8-Methoxycarbonyloctyl 4-deoxy-6-O-tert-butyl-dimethylsilyl-2-O-(2,3,4-tri-O-benzyl-α-D-glucopyranosyl)-α-D-glucopyranoside (33)

Compound 31 (150 mg, 0.13 mmol) was deoxygenated as described for the preparation of 15 to provide 32 which was not characterized at this stage but directly deacetlyated with sodium methoxide (~0.1N) in dry methanol (5 mL) to give 33 (75 mg, 63.4%) as a syrup after chromatography on silica gel using (hexane:ethyl acetate, 1:1) as eluant; $[\alpha]_D$+62.5° (c 0.23, chloroform). $^1$H-n.m.r. (CDCl$_3$): δ 5.23(ddd, $J_{3,4e}$ 5.0, $J_{3,4}$ 12.0, $J_{2,3}$ 10.0 Hz, H-3), 4.94(d, 1H, $J_{1',2'}$ 3.8 Hz, H-1'), 4.90(d, 1H, $J_{1,2}$ 3.8 Hz, H-1), 3.60(s, 3H, OCH$_3$), 2.21(t, 2H, J 7.5 Hz, CH$_2$COO), 2.12(m, 1H, H-4e), 1.35(ddd, 1H, $J_{3,4}$=$J_{4,5}$ 12.0, $J_{4a,4e}$ 12.5 Hz, H-4).

Anal. Calc. for $C_{49}H_{72}O_{12}Si$: C, 66.79; H, 8.24. Found: C, 66.29; H, 8.23.

Example 26

Synthesis of 8-Methoxycarbonyloctyl 3-O-benzyl-2-O-(2,3,4,6-tetra-O-benzyl-α-D-glucopyranosyl)-α-D-glucopyranoside (38)

Compound 23 (520 mg, 0.50 mmol) was dissolved in dichloromethane (5 mL) and 80% aqueous acetic acid (100 mL) was added. After stirring the reaction mixture for 20 hours at room temperature, the solvent was evaporated and coevaporated with toluene. The residue was purified by chromatography on silica gel using (hexane:ethyl acetate; 1:1) as eluant. Pure 38 (375 mg, 78.9%) was obtained as a syrup; $[\alpha]_D$+53.3° (c 0.06, chloroform). $^1$H-n.m.r. (CDCl$_3$): δ 5.08(d, 1H, $J_{1',2'}$ 3.8 Hz, H-1'), 5.03(d, 1H, $J_{1,2}$ 3.8 Hz, H-1), 3.66(s, 3H, OCH$_3$), 2.37– 2.30(m, 1H, D$_2$O exchangeable), 2.28(t, 2H, C$\underline{H}_2$COO), 1.92(m, 1H, OH, D$_2$O, exchangeable).

Anal. Calc. for C$_{57}$H$_{70}$O$_{13}$: C, 71.08; H, 7.33. Found: C, 70.99; H, 7.13.

Example 27

Synthesis of 8-Methoxycarbonyloctyl 3-O-benzyl-6-O-methanesulfonyl-2-O-(2,3,4,6-tetra-O-benzyl-α-D-glucopyranosyl)-α-D-glucopyranoside (39)

Compound 38 (450 mg, 0.47 mmol) was converted into its 6-O-methane sulfonyl derivative exactly as described for the preparation of 10 to provide 39 (385 mg, 79.1%) as a syrup after chromatography on silica gel using (hexane:ethyl acetate; 2:1) as eluant; $[\alpha]_D$+36.1° (c 0.95, chloroform). $^1$H-n.m.r. (CDCl$_3$): δ 4.99(d, 1H, $J_{1',2'}$ 3.8 Hz, H-1'), 4.96(d, 1H, $J_{1,2}$ 3.8 Hz, H-1), 3.58(s, 3H, OCH$_3$), 2.93(s, 3H, CH$_3$SO$_2$), 2.39(d, 1H, J 3.2 Hz, OH, D$_2$O exchangeable), 2.21(t, 2H, J 7.5 Hz, C$\underline{H}_2$COO).

Anal. Calc. for C$_{58}$H$_{72}$O$_{15}$S: C, 66.90; H, 6.97; S, 3.08. Found: C, 66.66; H, 6.78; S, 2.99.

Example 28

Synthesis of 8-Methoxycarbonyloctyl 3-O-benzyl-6-fluoro-2-O-(2,3,4,6-tetra-O-benzyl-α-D-glucopyranosyl)-α-D-glucopyranoside (40)

Compound 38 (250 mg, 0.24 mmol) was converted into 6-fluoro derivative exactly as described for the preparation of 13 to provide 40 (50 mg, 21.6%) as a syrup after chromatography on silica gel using (hexane:ethyl acetate; 3:1) as eluant; $[\alpha]_D$+52° (c 0.45, chloroform). $^1$H-n.m.r. (CDCl$_3$): δ 5.06(d, 1H, $J_{1',2'}$ 3.8 Hz, H-1'), 5.05(d, 1H, $J_{1,2}$ 3.8 Hz, H-1), 3.66(s, 3H, OCH$_3$), 2.26(t, 2H, J 7.5 Hz, C$\underline{H}_2$COO), 2.21(d, 1H, J 3.2 Hz, OH, D$_2$O exchangeable).

Anal. Calc. for C$_{57}$H$_{69}$O$_{12}$F: C, 70.93; H, 7.21; F, 1.97. Found: C, 70.89; H, 6.88, F, 1.99.

Example 29

Synthesis of 8-Methoxycarbonyloctyl 3-O-benzyl4O-methyl-2-O-(2,3,4,6-tetra-O-benzyl-α-D-glucopyranosyl)-α-D-glucopyranoside (41)

8-Methoxycarbonyloctyl 3-O-benzyl-6-O-methyl-2-O-(2,3,4,6-tetra-O-benzyl-α-D-glucopyranosyl)-α-D-glucopyranoside (42) and 8-Methoxycarbonyloctyl 3-O-benzyl-4,6-di-O-methyl-2-O-(2,3,4,6-tetra-O-benzyl-α-D-glucopyranosyl)-α-D-glucopyranoside (43)

A solution of compound 38 (320 mg, 0.33 mmol) in DMF (5 mL) was added dropwise at −10° C. to a solution of sodium hydride (32 mg of 50% dispersion in oil) in DMF (5 mL). After 0.5 hours, methyl iodide (41.4 μL, 0.67 mmol) was added dropwise and stirred into the reaction mixture for 6 hours at −5° C. to 10° C. After dilution with dichloromethane (50 mL), the mixture was poured into ice-water and washed with ice cold water (3×50 mL) before concentration to a syrup which was purified by chromatography on silica gel using (hexane:ethyl acetate; 2:1) as eluant to provide:

41 (80 mg, 24.6%); $[\alpha]_D$+65.1° (c 0.46, chloroform). $^1$H-n.m.r. (CDCl$_3$): δ 5.01 (d, 1H, $J_{1',2'}$3.8 Hz, H-1'), 5.05(d, 1H, $J_{1,2}$ 3.8 Hz, H-1), 3.66(s, 3H, OCH$_3$), 3.40(s, 3H, OCH$_3$), 2.45–2.39(m, 1H, OH, D$_2$O exchangeable), 2.28(t, 2H, J 7.5 Hz, C$\underline{H}_2$COO).

Anal. Calc. for C$_{58}$H$_{72}$O$_{13}$: C, 71.29; H, 7.43. Found: C, 71.13; H, 7.23.

42 (92 mg, 28.3%); $[\alpha]_D$+76.50° (c 0.17, chloroform). $^1$H-n.m.r. (CDCl$_3$): δ 5.06 (d, 1H, $J_{1',2'}$ 3.8 Hz, H-1'), 5.00(d, 1H, $J_{1,2}$ 3.8 Hz, H-1), 3.66, 3.57(s, 3H each, 2×OCH$_3$), 2.28(t, 2H, J 7.5 Hz, C$\underline{H}_2$COO), 1.98–1.90(m, 1H, OH, D$_2$O exchangeable).

Anal. Calc. for C$_{58}$H$_{72}$O$_{13}$: C, 71.29; H, 7.43. Found: C, 71.00; H, 7.18.

43 (104 mg, 31.6%); $[\alpha]_D$+71.4° (c 0.84, chloroform). $^1$H-n.m.r. (CDCl$_3$): δ 5.04 (d, 1H, $J_{1',2'}$ 3.8 Hz, H-1'), 5.02(d, 1H, $J_{1,2}$ 3.8 Hz, H-1), 3.66, 3.57, 3.42(s, 3H each, 3×OCH$_3$), 2.28(t, 2H, J 7.5 Hz, C$\underline{H}_2$COO).

Anal. Calc. for C$_{59}$H$_{74}$O$_{13}$: C, 71.49; H, 7.53. Found: C, 71.19; H, 7.21.

Example 30

Synthesis of 3,4,6-tri-O-acetyl-2-deoxy-2-fluoro-glucopyransoyl bromide (65)

(A) Synthesis of methyl-3,4,6-tri-O-acetyl-2-deoxy-2-fluoro-α-D-glucopyranoside

To a solution of known methyl 2-deoxy-2-fluoro-3-O-benzyl-4,6-benzylidene-α-D-glucopyranoside (1.5 g) in methanol (10.0 mL) was added 5% palladium on carbon (1.5 g) and the reaction mixture was stirred under one atmosphere of hydrogen for 15 hours. The reaction solution was then filtered to remove the catalyst and the solvent evaporated, co-evaporated with toluene and acetylated directly with acetic anhydride (5 mL) and pyridine (5 mL). After the usual workup, methyl-3,4,6-tri-O-acetyl-2-deoxy-2-fluoro-α-D-glucopyranoside (600 mg) was obtained as a syrup.

(B) Synthesis of 1,3,4,6-tetra-O-acetyl-2-deoxy-2-fluoro-glucopyranoside

A solution of concentrated H$_2$SO$_4$ (20 μL) in acetic anhydride (2 mL) was added dropwise over a period of 5 minutes to a solution of methyl-3,4,6-tri-O-acetyl-2-deoxy-2-fluoro-α-D-glucopyranoside (500 mg) in acetic anhydride (2 mL) and the reaction mixture was stirred for 5 hours at 0° C. The mixture was diluted with dichloromethane (100 mL) and washed with saturated NaHCO$_3$ solutions (2×100 mL) and water (2×100 mL), dried over Na$_2$SO$_4$, filtered and evaporated to dryness. The syrup was purified by chromatography on silica gel using hexane-ethyl acetate (3:1) and (2:1) as eluent to provide for 1,3,4,6-tetra-O-acetyl-2-deoxy-2-fluoro-glucopyranoside (320 mg).

(C) Synthesis of Bromo-3,4,6-tri-O-acetyl-2-deoxy-2-fluoro-glucopyranose 1,3,4,6-tetra-O-acetyl-2-deoxy-2-fluoro-glucopyranoside (320 mg) obtained as above was dissolved in dichloromethane (5.0 mL) and 30% HBr solution in acetic acid was added at 0° C. The reaction mixture was stirred for 1 hour at 0° C. and then 5 to 10 hours at room temperature. The reaction mixture was then evaporated and co-evaporated with toluene and dissolved in dichloromethane (50 mL) and washed with NaHCO$_3$ (2×50 mL) and water (2×80 mL) to obtain the title compound quantitatively.

Example 31

Synthesis of 2-deoxy-2-azido-3,4,6-tri-O-acetyl-glucopyransoyl bromide (66)

The title compound was prepared via known methods, e.g., Lemieux, et al., Offenlengunschrift 2 816 340.

Example 32

Synthesis of 2-O-methyl-3,4,6-tri-O-benzyl-α-D-glucopyranosyl bromide (67)

To a solution of 2,3,4,6-tetra-O-acetyl-glucopyranosyl bromide (51.6 g) in dry $CH_2Cl_2$ (120 mL) was added dry allyl alcohol (120 mL), 2,6-lutidine (37 mL) and tetraethylammonium bromide (50.4 g). The resulting solution was stirred for 5 hours at room temperature, 3 hours at 50° C. and 15 hours at 30° C. The reaction mixture was poured into water and extracted the dichloromethane. The water layer was washed with chloroform (2×1 L), dried over $Na_2SO_4$, filtered and concentrated.

The concentrate (50.0 g) prepared as above was deacetylated with sodium methoxide (0.5N) in methanol (1 L). The reaction mixture was neutralized with IR-120 resin, filtered and evaporated. Benzylation of the deacetylated material was carried out directly with sodium hydride in DMF using benzyl bromide to provide for the benzylated product (70 g).

The benzylated product (1.7 g) prepared as above was dissolved in dichloromethane (20 mL) and trimethylsilyl triflate (279 µL) was added dropwise thereto. After 30 minutes, the reaction was complete. The reaction solution was filtered and washed with dichloromethane (100 mL) and then poured into 125 mL of ice water. The resulting solution was extracted with dichloromethane (3×50 mL) dried over sodium sulfate, filtered, evaporated to provide for 1.6 g of product.

The entire amount of this product was dissolved in dry methanol (20 mL) and a solution of 0.5N sodium methoxide (10 mL) in methanol was added and the resulting solution stirred for 0.5 hours. Afterwards, the solution was neutralized with IR-120($H^+$) resin, washed with methanol (3×30 mL), evaporated and the resulting material used directly for preparation of 2-O-methylation. Specifically, the product (1.32 g) was dissolved in dry DMF (10 mL) and sodium hydride (130 mg) was added followed by addition of methyl iodide (340 µL) at 0° C. The resulting solution was stirred for 1 hour at room temperature. At this time, the solution was diluted with dichloromethane (125 mL) and poured in an ice cold water solution and then extracted with $CH_2Cl_2$ (3×75 mL) dried ($Na_2SO_4$) and evaporated. Chromatography of the material using hexane-ethyl acetate (3:1) as eluent provided allyl-2-O-methyl-3,4,6-tri-O-benzyl-α-D-glucopyranoside (906 mg).

Allyl-2-O-methyl-3,4,6-tri-O-benzyl-α-D-glucopyranoside (850 mg) was deallylated by conventional methods using tris triphenylphosphine rhodium (I) chloride (120 mg), 1,4-diazabicyclo[2.2.2] octane (43 mg) and refluxing the mixture in ethanol-benzene-water (7:3:1) (20 mL). Hydrolysis was carried out by using mercuric chloride (600 mg) in acetone-water (9:1) (50 mL) mixture. Following evaporation of the solvent, compound was taken in $CH_2Cl_2$ (100 mL) and washed with 30% aqueous potassium bromide (2×100 mL) and water (2×100 mL), dried over $Na_2SO_4$ and evaporated to give an oily residue which was purified by chromatography on silica gel using hexane-ethyl acetate (3:1) as eluent to give 2-O-methyl-3,4,6-tri-O-benzyl-glucopyranoside (550 mg).

2-O-methyl-3,4,6-tri-O-benzyl-glucopyranoside (500 mg) was dissolved in dichloromethane (10.0 mL) and DMF (200 µL) was added. Oxalyl bromide (300 µL) was dropwise added over 15 minutes and the resulting mixture stirred for 2 hours at 0° to 5° C. The resulting solution was poured into 100 mL of water and 100 mL of $CH_2Cl_2$. The organic layer was washed with water (2×200 mL) dried over $Na_2SO_4$ and evaporated to provide the title compound. The yield was for this last step quantitative and synthesis was conducted just prior to use.

Example 33

Synthesis of 2-deoxy-1,3,4,6-tetra-O-acetyl(α,β)-glucopyranoside (68,69)

2-Deoxy-glucopyranoside (available from Aldrich (5.0 g)) was acetylated with acetic anhydride (3.0 mL) and pyridine (3.0 mL) by stirring the reaction mixture for 4 hours at room temperature. The reaction mixture was evaporated, co-evaporated with toluene and washed as described earlier to provide for the title compounds as a mixture of α and β isomers.

Example 34

Synthesis of Benzyl 2-deoxy-3,4,6-tri-O-acetyl-1-thio-(α,β)-D-glucopyranoside (70,71)

To a solution of 2-deoxy-glucose tetraacetate 68,69 (1.5 g, 4.5 mmol) in dry dichloromethane (10 mL) was added benzyl mercaptan (1.1 mL, 9.0 mmol). To this mixture was added boron trifluoride ethereate (1.67 mL, 13.5 mmol) in one portion. The reaction mixture was stirred for 5 h at room temperature then quenched with saturated sodium hydrogen carbonate. After $CO_2$ evolution had ceased, the organic layer was separated and the aqueous layer extracted with dichloromethane (2×100 mL). The combined organic extracts were dried ($Na_2SO_4$) and evaporated to dryness. Column chromatography of the residue using (hexane:ethyl acetate; 2:1) as eluant provided 70,71 (1.49 g, 77.5%) as an α,β mixture. $^1$H-n.m.r. ($CDCl_3$): δ 5.25(bd, $J_{1,2}$ 4.0 Hz, H-1α), 2.15–1.95 (6×Ac, α,β).

Example 35

Synthesis of Benzyl 2-deoxy-3,4,6-tri-O-benzyl-1-thio-(α,β)-D-glucopyranoside (74,75)

Compound 70,71 (900 mg, 2.2 mmol) was O-deacetylated as described for the preparation of 3 to provide 72,73 which was directly benzylated exactly as described for the preparation of 23 to provide 74,75 (1.19 g, 90.5%) as a syrup after chromatographic purification using (hexane:ethyl acetate; 5:1) as eluant. $^1$H-n.m.r. ($CDCl_3$): δ 5.28(bd, $J_{1,2}$ 4.5 Hz, H-1α), 4.88(d, $J_{1,2}$ 10.0 Hz, H-1β), 2.29–1.66(m, H-2α and H-2β).

Example 36

Synthesis of Benzyl 2-deoxy-3,4,6-tri-O-benzyl-1-thio-(α,β)-D-glucopyranoside (74) and (75)

To a solution of 2-deoxy-glucose tetraacetate obtained from acetylation of 2-deoxy-glucose (1.5 g, 4.5 mmol) in dry dichloromethane (10 mL) was added benzyl mercaptan (1.1 mL), 9.0 mmol). To this mixture was added boron trifluoride ethereate (1.67 mL, 13.5 mmol) in one portion. The reaction mixture was stirred for 5 hours at room temperature then quenched with saturated sodium hydrogen carbonate. After CO$_2$ evolution had ceased, the organic layer was separated and aqueous layer extracted with dichloromethane (2×100 mL). The combined organic extracts were dried (Na$_2$SO$_4$) and evaporated to dryness. Column chromatography of the residue using hexane-ethyl acetate (2:1) as eluent provided benzyl 2-deoxy-3,4,6-tri-O-acetyl-1-thio-(α,β)-D-glucopyranoside (1.49 g, 77.5%) as an α,β mixture. $^1$H NMR (CHCl$_3$): δ 5.25(bd, J$_{1,2}$4.0 Hz,H-1α),2.15–1.95 (6×Ac,α,β).

Benzyl 2-deoxy-3,4,6-tri-O-acetyl-1-thio-(α,β)-D-glucopyranoside (900 mg, 2.2 mmol) was O-deacetylated as described earlier to provide deacetylated product which was directly benzylated exactly as described earlier to provide compounds 74 and 75 (1.19 g, 90.5%) as a syrup after chromatographic purification using hexane-ethyl acetate (5:1) as eluent. $^1$H NMR (CHCl$_3$): δ 5.28(bd, J$_{1,2}$4.5 Hz,H-1α),4.88(d,J$_{1,2}$10.0 Hz,H-1β), 2.29–1.66(m,H-2α and H-2β).

Example 37

Synthesis of 3-deoxy-2,4,6-tri-O-benzyl-glucopyranosyl bromide (76)

Known 1,2,4,6-tetra-O-acetyl-3-O-benzylglucopyranose (10.0 g) was hydrogenated with palladium on carbon (5.0 g) in methanol (100 mL) by stirring the reaction mixture for 1 hour at room temperature and atmospheric pressure to provide for 1,2,4,6-tetra-O-acetyl-glucopyranoside (6 g).

1,2,4,6-tetra-O-acetyl-glucopyranoside (6 g) was dissolved in anhydrous acetonitrile (120 mL) and dimethylaminopyridine (3.6 g) and phenyl-chlorothionoformate (5.4 mL) was added thereto. The resulting solution was refluxed. After complete disappearance of the starting material, the reaction mixture was diluted with dichloromethane (250 mL) and washed with water (2×250 mL), dried over Na$_2$SO$_4$, evaporated and purified by chromatography on silica gel using hexane-ethyl acetate (3:2) as eluent to provide for 1,2,4,6-tetra-O-acetyl-3-O-phenylthiono-glucopyranose (5.2 g).

1,2,4,6-tetra-O-acetyl-3-O-phenylthiono-glucopyranose (5.2 g) was dissolved in toluene (50 mL) and added to tributyl tin hydride (6.7 mL) and azobisisobutyronitrile (2.8 g). The reaction mixture was heated for 1 to 3 hours at 80° C. to provide for 3-deoxy-2,4,6-tri-O-acetyl-glucopyranose (4.5 g).

3-deoxy-2,4,6-tri-O-acetyl-glucopyranose (4.5 g) was dissolved in freshly distilled mixture of dichloromethane-ethyl acetate (9:1) (15.0 mL). Titanium tetrabromide (7.5 g) was added slowly at 0° C. and the reaction mixture was allowed to stir at room temperature for 15 hours. The reaction solution was then diluted with methylene chloride (250 mL) and sodium acetate was added. The organic layer was washed with water (3×250 mL), dried over Na$_2$SO$_4$, filtered and evaporated to give the bromide quantitatively.

A mixture of 3-deoxy-2,4,6-tri-O-acetyl-α-D-glucopyranosyl bromide (4.5 g), molecular sieves (4.5 g), silver carbonate (4.5 g), dichloromethane (20.0 mL) and allyl alcohol (4.5 mL) was stirred in the dark at room temperature for 12 hours. The precipitate was washed with dichloromethane and combined filtrate and washings were concentrated to a syrup. Chromatography of the material on silica gel using hexane-ethyl acetate (3:1) and (2:1) as eluent provided allyl-3-deoxy-2,4,6-tri-O-acetyl-β-D-glucopyranoside (3.5 g).

Allyl-3-deoxy-2,4,6-tri-O-acetyl-β-D-glucopyranoside (3 g) was dissolved in methanol (20 mL) and a catalytic amount of sodium methoxide (0.5 m in methanol) was added. The reaction solution was stirred for 5 hours at room temperature. The reaction mixture was neutralized with IR-120(H$^+$) resin, filtered, evaporated and benzylated with benzyl bromide (2.5 mL), sodium hydride (3.0 g) in DMF (20.0 mL) to provide for allyl-3-deoxy-2,4,6-tri-O-benzyl-β-D-glucopyranoside (4.0 g) after purification of the compound by chromatography on silica gel using hexane-ethyl acetate (5:1) as eluent.

Allyl-3-deoxy-2,4,6-tri-O-benzyl-β-D-glucopyranoside (3.5 g) was dissolved in a mixture of ethanol-benzene-water (7:3:1, 70 mL) and tris triphenylphosphine rhodium (1) chloride (500 mg) and 1,4-diazabicyclo[2.2.2]octane (216 mg) was added thereto. The reaction mixture was refluxed for 5 hours and taken to dryness. The isomerized product was hydrolyzed by dissolving the compound in a mixture of acetone-water (9:1, 100 mL) and adding mercury (II) chloride (18.0 g) and mercury (II) oxide (170 g). Stirred the reaction mixture for 30–45 minutes at room temperature. Filtered, evaporated and redissolved the residue in dichloromethane (150 mL) and washed successively with 30% KBr solution (2×150 mL) and water (2×150 mL), dried over sodium sulfate, filtered and evaporated to dryness. The syrup was purified by chromatography on silica gel using hexane-ethyl acetate (5:1) as eluent to give 3-deoxy-2,4,6-tri-O-benzyl-glucopyranose (2.5 g).

3-Deoxy-2,4,6-tri-O-benzyl-glucopyranose (2.2 g) was dissolved in dichloromethane (20 mL) and dry DMF (880 μL) was added. The reaction solution was cooled at 0° C. and oxalyl bromide (500 μL) was added and the resulting solution stirred at 0° to 5° C. for 1 hour. The solution was then diluted with dichloromethane (100 mL) and washed with water (3×100 mL), dried over sodium sulfate, filtered and evaporated to dryness to obtain 3-deoxy-2,4,6-tri-O-benzyl-glucopyranosyl bromide (compound 13).

Example 38

Synthesis of 3-O-methyl-2,4,6-tri-O-benzyl-glucopyranosyl bromide (77)

Diacetone glucose (20 g), DMF (200 mL) and sodium hydride (2.78 g) were combined and then stirred for 20 minutes at 0° C. Methyl iodide (7.2 mL) was then dropwise added to the solution which was then stirred for 2 hours at room temperature. The reaction mixture was then diluted with CH$_2$Cl$_2$ (1 L) and washed with water (3×1 L), filtered, dried over sodium sulfate and evaporated which gave quantitative yield of 3-O-methyl-1,2:5,6-di-O-isopropylidne-glucopyranose (18.0 g) which was used without further purification.

3-O-methyl-1,2:5,6-di-O-isopropylidine-glucopyranose (10.2 g) was dissolved in 90% aqueous trifluoroacetic acid (30 mL) and stirred for 1 hour at room temperature. The reaction mixture was evaporated and then coevaporated with toluene followed by ethanol coevaporation to provide the product which was directly used for further allyl glycosylation. 7.9 g of 3-O-methyl-glucopyranose was dissolved in 50 mL of dry allyl alcohol and 120 μL of trifluoromethanesulfonic acid was added. The mixture was heated for 5½ h at 80° C. Triethylamine (1 mL) was added to destroy excess trifluoromethanesulfonic acid, evaporated and coevaporated with water to remove allyl alcohol. The material was purified by chromatography on silica gel using dichloromethane-methanol (20:1) as eluent to yield allyl-3-O-methyl-glucopyranose (4.85 g, 50.8%).

Allyl-3-O-methyl-glucopyranose (4.5 g) was dissolved in anhydrous DMF (120 mL) and sodium hydride (1.84 g, 50% dispersion in oil) was added thereto. The resulting solution was stirred for 0.5 hours at 0° C. Benzyl bromide (6.8 mL) was added dropwise at 0° to 5° C. and the reaction mixture was then stirred for 4 hours at room temperature. The reaction mixture was quenched by adding methanol, diluted with dichloromethane (250 mL) and washed with water (3×250 mL), dried over $Na_2SO_4$, filtered and evaporated. The material was purified by chromatography on silica gel using hexane-ethyl acetate (5:1) as eluent. The evaporated fractions from column were crystallized from a mixture of dichloromethane and hexane to provide for allyl-3-O-methyl-2,4,6-tri-O-benzyl-glucopyranose (8 g).

Allyl-3-O-methyl-2,4,6-tri-O-benzyl-glucopyranose (7.4 g) was refluxed for 5 hours in a mixture of ethanol/benzene/water (7:3:1) (500 mL) containing tris triphenylphosphine rhodium (I) chloride (1.05 g) and diazabicyclo[2.2.2]octane (445 mg). The isomerized product was hydrolyzed in acetone-water (9:1) (140 mL) using mercuric chloride (18.6 g) and mercuric oxide (383 mg) by stirring the reaction mixture at room temperature for 1 hour. The resulting solution was evaporated to dryness, diluted with methylene chloride (500 mL), filtered and washed with 30% KBr (3×500 mL) and water (3×500 mL), dried over $Na_2SO_4$, concentrated and purified by chromatography on silica gel using hexane-ethyl acetate (4:1) and (3:1) as eluents to provide 2,3,4-tri-O-benzyl-3-O-methyl-D-glucopyranose (5.0 g).

2,3,4-Tri-O-benzyl-3-O-methyl-D-glucopyranose (1.0 g) was dissolved in dry dichloromethane (10 mL) and DMF (500 μL) and oxalyl bromide were then dropwise (250 μL) added. The resulting reaction mixture was stirred for 1 hour at 0° to 5° C. and for 1 hour at room temperature. The reaction mixture was then diluted with dichloromethane (250 mL) and washed with water (3×250 mL) to provide for the title compound quantitatively for this last step.

Example 39

Synthesis of 4-deoxy-2,3,6-tri-O-benzyl-glucopyranosyl bromide (78)

Allyl-2,3,6-tri-O-benzyl-glucopyranose (960 mg) (per Example 40 below) was dissolved in dry pyridine and added 65 μL of sulfuryl chloride at 0° C. dropwise. The reaction mixture was stirred at this temperature for 15 hours. Dichloromethane (150 mL) was added and the resulting solution was washed with sodium bicarbonate (2×150 mL) and water (2×150 mL). Solvent removal left the residue which was purified by chromatography on silica gel using hexane-ethyl acetate (5:1) as eluent to provide compound allyl 4-chloro-4-deoxy-2,3,4-tri-O-benzyl-galactopyranose (550 mg).

A mixture of allyl 4-chloro-4-deoxy-2,3,4-tri-O-benzyl-galactopyranose (500 mg), of tributyltin hydride (2 eq) and AIBN (1.0 eq) in 20 mL toluene was heated at 90° C. for 3 hours. Solvent was evaporated and the residue was chromatographed on a silica gel column using hexane-ethyl acetate (5:1) as eluent to provide allyl-4-deoxy-2,3,4-tri-O-benzyl-glucopyranoside (300 mg).

Allyl-4-deoxy-2,3,4-tri-O-benzyl-glucopyranoside (2.46 g) was dissolved in a mixture of ethanol-benzene and water (7:3:1, 50 mL) and tris triphenylphosphine rhodium (1) chloride (350 mg) and 1,4-diazabicyclo[2.2.2]octane (148 mg) were added thereto. The resulting solution was refluxed for 5 hours. Afterwards, the solvent was evaporated to complete dryness and the isomerized product was hydrolyzed by dissolving it into a mixture of acetone-water (9:1, 50 mL) by adding mercuric chloride (5.6 g) followed by mercuric oxide (100 mg) and stirring the reaction mixture for 45 minutes at room temperature. Solvent was evaporated and dichloromethane (150 mL) was added. The dichloromethane layer was washed successively with 30% aqueous potassium bromide (2×150 mL) and water (2×150 mL), dried over $Na_2SO_4$, filtered and evaporated to dryness. The product was purified by chromatography on silica gel using hexane-ethyl acetate (5:1) as eluent to provide 4-deoxy-2,3,6-tri-O-benzyl-glucopyranoside (1.50 g).

4-Deoxy-2,3,6-tri-O-benzyl-glucopyranoside (1.5 g) was dissolved in dry dichloromethane (15.0 mL) and dry DMF (750 μL) was added. The reaction mixture was cooled to 0° C. and oxalyl bromide (350 μL) was dropwise added. The resulting solution was stirred it at 0° C. to 5° C. for 1 hour. The solution was then diluted with dichloromethane (100 mL), washed with water (2×100 mL), dried over sodium sulfate, filtered and evaporated to provide for the title compound. The yield was quantitative and ready to use.

Example 40

Synthesis of 4-O-methyl-2,3-6-tri-O-benzyl-glucopyranosyl bromide (79)

Compound 1 (obtained by reacting glucose in dry allyl alcohol in the presence of trifluoromethane sulfonic acid and refluxing for 6 hours at 80° C.) (27.9 g) was dissolved in anhydrous DMF (250 mL) and added p-toluene sulfonic acid (1.46 g). Benzaldehyde dimethylacetyl (28.5 mL) was added to the reaction mixture and the resulting solution stirred for 7.5 hours at room temperature. Another 20.5 mL of benzyldehyde dimethylacetal was then added and this solution stirred for 15 hours at room temperature. The reaction mixture was neutralized with triethylamine, evaporated to dryness, coevaporated with water. Diluted with 300 mL of $CH_2Cl_2$ and washed with water (2×300 mL) dried over $Na_2SO_4$, filtered and evaporated to obtain allyl-4,6-O-benzylidene glucopyranose (35.3 g).

Allyl-4,6-O-benzylidene glucopyranose (2.86 g) was dissolved in anhydrous DMF (100 mL). Sodium hydride (50% dispersion in oil) (669 mg) was added at 0° C. and dropwise addition of benzyl bromide (2.77 mL) was made at 0° C. The resulting solution was stirred for 4 hours at room temperature and then diluted with dichloromethane (250 mL), washed with water (2×250 mL), dried over $Na_2SO_4$, filtered and evaporated. The material was purified by chromatography on silica gel using hexane-ethyl acetate (3:1) and eluent to provide for allyl-2,3di-O-benzyl-4,6-O-benzylidene glucopyranose (3.5 g).

Allyl-2,3-di-O-benzyl-4,6-O-benzylidene glucopyranose (8.0 g) was dissolved in anhydrous THF (250 mL) and added to it molecular sieves (8.0 g), methyl orange crystals and sodium cyanoborohydride (13.8 g). Dropwise addition of saturated HCl ethereal solution was made at 0° C. until the reaction mixture attains pH 3 at 0° C. After 15 minutes, the reaction was complete. Diluted with dichloromethane (500 mL) and filtered the solid mass and washed. The filtrate and washings were combined together and washed with sodium hydrogen carbonate (2×750 mL) and water (2×750 mL) before evaporation to a syrup. The compound was purified by chromatography using hexane-ethyl acetate (4:1) as eluent to give allyl-2,3,6-tri-O-benzyl-glucopyranose (5.5 g, 67.6%)

Allyl-2,3,6-tri-O-benzyl-glucopyranose (5.5 g) was dissolved in anhydrous DMF (50 mL) and sodium hydride (528 mg) (50% dispersion in oil) was added at 0° C. The reaction mixture was then stirred for 0.5 hours at 0° C. Methyl iodide (1.37 mL) was added dropwise at this temperature and the mixture was stirred for 1 hour at 0° to 5° C. The reaction solution was diluted with dichloromethane (100 mL) and washed with water (2×100 mL), dried over $Na_2SO_4$, filtered and evaporated to yield (5.72 g) of the product allyl-4-O-methyl-2,3,6,-tri-O-benzyl-glucopyranose.

Allyl-4-O-methyl-2,3,6,-tri-O-benzyl-glucopyranose (5.7 g) was dissolved in a mixture of ethanol-benzene-water (7:3:1; 75 mL). Tris triphenylphosphine rhodium (I) chloride (805 mg) and 1,4-diazabicyclo[2.2.2]octane (342 mg) were added and the resulting solution refluxed for 5 hours. The solution was evaporated to dryness and the product was treated with mercury (II) chloride (14.4 g) and a trace of mercuric oxide (0.3 g) in a mixture of acetone and water (9:1, 50 mL). After 1 hour, reaction was complete. The reaction mixture was filtered, evaporated and dissolved in dichloromethane (250 mL). The organic solution was washed with 30% KBr solution (2×250 mL) and with water (2×250 mL), dried over sodium sulfate and purified by chromatography on silica gel using hexane-ethyl acetate (3:1) as eluent to provide 4-O-methyl-2,3-6-tri-benzyl-glucopyranose (2.32 g).

4-O-methyl-2,3-6-tri-O-benzyl-glucopyranose (1.5 g) was converted into its bromo derivative as described earlier with oxalyl bromide and DMF to provide the quantitative yield of the title compound.

Example 41

Synthesis of 8-Methoxycarbonyoctyl 3-O-acetyl-4, 6-O-benzyldene-2-O-(2-deoxy-2-fluoro-3,4,6-tri-O-acetyl-α-D-glucopyranosyl)-α-D-glucopyranoside (80).

Compound 6 (120 mg, 0.25 mmol) was glycosylated with bromide 65 exactly as described for the preparation of 8 to provide 80 (160 mg, 83.1%) as a syrup after chromatography on silica gel using (hexane:ethyl acetate; 2:1) as eluant; $[\alpha]_D$+125.3° (c 0.50, chloroform). $^1$H-n.m.r . (CDCl$_3$): δ 5.59(t, 1H, $J_{2,3}$=$J_{3,4}$ 10.0 Hz), 5.48(s, 1H, $C_6H_5C\underline{H}O_2$), 5.12(d, 1H, $J_{1,2}$ 3.8 Hz, H-1'), 5.05(t, 1H, $J_{2,3}$=$J_{3,4}$ 10.0 Hz, H-3'), 4.96(d, 1H,$J_{1,2}$ 3.8 Hz, H-1), 3.67(s, 3H, OCH$_3$), 2.31(t, 2H, J 7.5 Hz, C$\underline{H}_2$COO), 2.11, 2.10, 2.06 and 2.04 (s, 3 each, 4Ac).

Anal. Calc. for $C_{37}H_{51}O_{16}F$: C, 57.65; H, 6.67; F, 2.47. Found: C, 57.81; H, 6.75; F, 2.40.

Example 42

Synthesis of 8-Methoxycarbonyloctyl 4,6-O-benzylidene-3-O-acetyl-2-O-(2-azido-2-deoxy-3,4,6-tri-O-acetyl-α-D-glucopyranosyl)-α-D-glucopyranoside (82).

A solution of 66 (123.2 mg, 0.31 mmol) in dicthloromethane was added with stirring to a mixture of 6 (75 mg, 0.16 mmol), mercuric bromide (112.6 mg, 0.31 mmol), mercuric cyanide (79 mg, 0.31 mmol) and drierite (500 mg) in dichloromethane (2 mL) kept at room temperature. The reaction was monitored by t.l.c. and after completion (8 h), the mixture was filtered and the solution was washed consecutively with saturated sodium hydrogencarbonate and water, dried ($Na_2SO_4$) filtered and concentrated to dryness. Chromatography of the residue on silica gel using (hexane:ethyl acetate; 2:1) as eluant gave the pure disaccharide 82 (92 mg, 74.2%) $[\alpha]_D$+134.3° (c, 0.64, chloroform). $^1$H-n.m.r. (CDCl$_3$): δ 5.59(t, 1H, $J_{2,3}$=$J_{3,4}$ 10.0 Hz, H-3'), 5.48(s, 1H, $C_6H_5C\underline{H}O_2$), 5.41(t, 1H, $J_{2,3}$=$J_{3,4}$ 10.0 Hz, H-3), 3.64(s, 3H, OCH$_3$), 2.30(t, 2H, J 7.5 Hz C$\underline{H}_2$COO), 2.10, 2.08, 2.07, 2.03(s, 3H each, 4Ac).

Anal. Calc. for $C_{37}H_{51}O_{16}N_3$: C, 55.98; H, 6.48; N, 5.29. Found: C, 55.79; H, 6.39; N, 5.21.

Example 43

Synthesis of 8-Methoxycarbonyloctyl 4,6-O-benzylidene-3-O-acetyl-2-O-(2-O-methyl-2,3,4-tri-O-benzyl-α-D-glucopyranosyl)-α-D-glucopyranoside (84).

A mixture of 6 (180 mg, 0.38 mmol) and silver trifluoromethane sulfonate (192.5 mg, 0.75 mmol) was dried in vacuo over $P_2O_5$ for 1 h at 25° C. and dissolved in dichloromethane (2 mL) under nitrogen. To this stirred mixture was added sym-collidine (99 μL, 0.75 mmol) and pulverized molecular sieves 4A (500 mg) and the mixture was stirred at 0° C. for 10 min. To this stirring mixture was added bromide 67 (333.2 mg, 0.75 mmol) in dichloromethane (2 mL) and the mixture was stirred for 1 h at 0° C. and 5 h at room temperature. After 24 h, dichloromethane (50 mL) was added and the sieves were removed by filtration and washed with more dichloromethane (50 mL). After evaporation of the solvent the residual syrup was purified by chromatography on Iatrobeads using (hexane:ethyl acetate; 3:1) as eluant to give 84 (250 mg, 72%) as a syrup; $[\alpha]_D$+81° (c 0.47, chloroform). $^1$H-n.m.r. (CDCl$_3$): δ 5.58(t, 1H, $J_{2,3}$=$J_{3,4}$ 10.0 Hz, H-3), 5.46(s, $C_6H_5C\underline{H}O_2$), 5.04(d, 1H, $J_{1',2'}$ 3.8 Hz, H-1'), 3.63(s, 3H, OCH$_3$), 3.50(s, 3H, OCH$_3$), 2.27(t, 2H, J 7.5 Hz, C$\underline{H}_2$COO), 2.02(s, 3H, Ac).

Anal. Calc. for $C_{53}H_{66}O_{14}$: C, 68.66; H, 7.18. Found: C, 68.36; H, 7.19.

Example 44

Synthesis of 8-Methoxycarbonyloctyl 4,6-O-benzylidene-3-O-acetyl-2-O-(2-deoxy-3,4,6-tri-O-benzyl-α-D-glucopyranosyl)-α-D-glucopyranoside (86).

Dimethylformamide (128.7 μL, 1.66 mmol) and tetraethyl-ammonium bromide (52.5 mg, 0.25 mmol) were added to a suspension of cupric bromide (278.9 mg, 1.25 mmol) and molecular sieves 4A (400 mg). After stirring the dark green mixture for 0.5 h at room temperature, a solution of compound 6 (80 mg, 0.17 mmol) in dichloromethane (1 mL) and of the thioglycoside 74,75 (265 mg, 0.5 mmol) in dichloromethane (1 mL) was syringed in dropwise in about 0.5 h. After stirring for 36 h, collidine (100 μL) was added then diluted with dichloromethane (25 mL). The solids were filtered and washed with dichloromethane (50 mL). Filtrate and washings were evaporated to get a syrup which was purified by chromatography on silica gel using (hexane:ethyl acetate; 4: 1) as eluant. Pure 86 (98.5 mg, 66%) was obtained as a syrup; $[\alpha]_D$+27.3° (c 0.11, chloroform). $^1$H-n.m.r. (CDCl$_3$): δ 5.52(t, 1H, $J_{2,3}$=$J_{3,4}$ 10.0 Hz, H-3), 5.46(s, 1H, $C_6H_5C\underline{H}O_2$), 5.07(d, 1H,$J_{1',2'}$ 3.0 Hz, H-1'), 5.04(d, 1H, $J_{1,2}$ 3.8 Hz, H-1), 3.66(s, 3H, OCH$_3$), 2.29(t, 2H, J 7.5 Hz, C$\underline{H}_2$COO), 2.02(s, 3H, Ac).

Anal. Calc. for $C_{52}H_{64}O_{13}$: C, 69.62; H, 7.19. Found: C, 69.32; H, 7.11.

Example 45

Synthesis of 8-Methoxycarbonyloctyl 4,6-O-benzylidene-3-O-acetyl-2-O-(3-deoxy-2,4,6-tri-O-benzyl-α-D-glucopyranosyl)-α-D-glucopyranoside (88).

Compound 6 (120 mg, 0.25 mmol) was glycosylated with bromide 76 exactly as described for the preparation of 84 to give 88 (180 mg, 77.8%) as a syrup after purification by chromatography on silica gel using (hexane:ethyl acetate; 3:1) as eluant; $[\alpha]_D$ +23° (c, 0.11, chloroform). $^1$H-n.m.r. (CDCl$_3$): δ 5.53(t, 1H, J$_{2,3}$=J$_{3,4}$ 10.0 Hz, H-3), 5.38(s, 1H, C$_6$H$_5$C$\underline{H}$O$_2$), 4.96(d, 1H, J$_{1',2'}$ 3.8 Hz, H-1'), 4.91(d, 1H, J$_{1,2}$ 3.2 Hz, H-1), 3.61(s, 3H, OCH$_3$), 2.25(ddd, 1H, J$_{3a,3e}$ 120.0 J$_{3e,2}$ 5.0 J$_{3e,4}$ 4.5 Hz, H-3e), 2.20(t, 2H, J 7.5 Hz, C$\underline{H}_2$COO), 1.97(s, 3H, Ac), 1.78(ddd, 1H, J$_{3a,2}$ 11.5 J$_{3a,4}$ 11.0 Hz, H-3a).

Anal. Calc. for C$_{52}$H$_{64}$O$_{13}$: C, 69.62; H, 7.19. Found: C, 69.32; H, 7.18.

Example 46

Synthesis of 8-Methoxycarbonyloctyl 4,6-O-benzylidene-3-O-acetyl-2-O-(3-O-methyl-2,4,6-tri-O-benzyl-α-D-glucopyranosyl)-α-D-glucopyranoside (90).

Compound 6 (150 mg, 0.31 mmol) was glycosylated with bromide 77 exactly as described for the preparation of 84 to give 90 (210 mg, 72.6%) as a syrup, after chromatography on silica gel using (hexane:ethyl acetate; 3:1) as eluant. $[\alpha]_D$+66.9° (c 0.35, chloroform). $^1$H-n.m.r. (CDCl$_3$): δ 5.55 (t, 1H, J$_{2,3}$=J$_{3,4}$ 10.0 Hz, H-3) 5.45(s, 1H, C$_6$H$_5$C$\underline{H}$O$_2$), 4.97(d, 1H, J$_{1',2'}$ 3.8 Hz, H-1'), 4.88 (d, 1H, J$_{1,2}$ 3.8 Hz, H-1), 3.65(s, 3H, OCH$_3$), 2.27(t, 2H, J 7.5 Hz, C$\underline{H}_2$COO), 2.01(s, 3H, Ac).

Anal. Calc. for C$_{53}$H$_{66}$O$_{14}$: C, 68.66; H, 7.18. Found: C, 68.61; H, 7.23.

Example 47

Synthesis of 8-Methoxycarbonyloctyl 4,6-O-benzylidene-3-O-acetyl-2-O-(4-deoxy-2,3,6-tri-O-benzyl-α-D-glucopyranosyl)-α-D-glucopyranoside (92).

Compound 6 (140 mg, 0.29 mmol) was glycosylated with bromide 78 as described for the preparation of 84 to give 92 (190 mg, 72.7%) as a syrup after chromatography on silica gel using (hexane:ethyl acetate; 3:1) as eluant; $[\alpha]_D$ +22° (c 0.50, chloroform). $^1$H-n.m.r. (CDCl$_3$): δ 5.53(t, 1H, J$_{2,3}$=J$_{3,4}$ 10.0 Hz, H-3), 5.46(s, 1H, C$_6$H$_5$C$\underline{H}$O$_2$), 4.97(d, J$_{1',2'}$ 3.5 Hz, H-1'), 4.93(d, J$_{1,2}$ 3.5 Hz, H-1), 3.65(s, 3H, OCH$_3$), 2.02(s, 3H, Ac).

Anal. Calc. for C$_{52}$H$_{64}$O$_{13}$: C, 69.62; H, 7.19. Found: C, 69.29; H, 7.23.

Example 48

8-Methoxycarbonyloctyl 4,6-O-benzylidene-3-O-acetyl-2 -O-(4-O-methyl-2,3,6-tri-O-benzyl-α-D-glucopyranosyl)-α-D-glucopyranoside (94).

Compound 6 (135 mg, 0.28 mmol) was glycosylated with bromide 79 exactly as described for the preparation of 84 to give 94 (180 mg, 69.1%) as a syrup after chromatography on silica gel using hexane:ethyl acetate; 3:1) as eluant; $[\alpha]_D$ +80° (c 0.35, chloroform). $^1$H-n.m.r. (CDCl$_3$): δ 5.58(t, 1H, J$_{2,3}$=J$_{3,4}$ 10.0 Hz, H-3), 5.46(s, 1H, C$_6$H$_5$C$\underline{H}$O$_2$), 5.0(d, 1H, J$_{1',2'}$ 3.8 Hz, H-1'), 4.90(d, 1H, J$_{1,2}$ 3.8 Hz, H-1), 3.65(s, 3H, OCH$_3$), 3.44(s, 3H, OCH$_3$), 2.27(t, 2H, J 7.5 Hz, C$\underline{H}_2$COO), 2.03(s, 3H, Ac).

Anal. Calc. for C$_{53}$H$_{66}$O$_{14}$: C, 68.66; H, 7.18. Found: C, 68.86 H, 7.28.

Example 49

Synthesis of 8-Methoxycarbonyloctyl 3-O-acetyl4,6-O-benzylidene-2-O-(2,3,4-tri-O-benzyl-α-D-xylopyranosyl)-α-D-glucopyranoside (97).

Compound 6 (100 mg, 0.21 mmol) was glycosylated with bromide 96 as described for the preparation of 84 to give 97 (135 mg, 73.5%) as a syrup after chromatography on silica gel using (hexane:ethyl acetate; 3:1) as eluant; $[\alpha]_D$ +76° (c 0.32, chloroform). $^1$H-n.m.r. (CDCl$_3$): δ 5.58(t, 1H, J$_{2,3}$ 10.0 Hz, H-3), 5.47(s, 1H, C$_6$H$_5$C$\underline{H}$O$_2$), 4.96(d, 1H, J$_{1',2'}$ 3.8 Hz, H-1'), 4.80(d, 1H, J$_{1,2}$ 3.8 Hz, H-1), 3.64(s, 3H, OCH$_3$), 2.28(t, 2H, J 7.5 Hz, C$\underline{H}_2$COO), 2.07(s, 3H, Ac).

Anal. Calc. for CH$_{62}$O$_{13}$: C, 69.37; H, 7.08. Found: C, 69.07; H, 7.11.

Example 50

Synthesis of 8-Methoxycarbonyloctyl 2-O-(α-D-glucopyranosyl)-α-D-glucopyranoside (44).

Compound 8 (120 mg, 0.13 mmol) was O-deactylated as described for the preparation of 3 to provide a foamy solid (98.5 mg) which was dissolved in 98% ethanol (5 mL) and hydrogenated over 5% palladium on charcoal (60 mg) at atmospheric pressure for 15 h. The catalyst was removed by filtration and after solvent evaporation, the residue was passed through a column of Bio-Gel P2 (2.5 cm×47 cm) using 10% aqueous ethanol as eluant. The carbohydrate containing fractions were pooled, concentrated, and lyophilized to provide 44 as a white powder (52 mg, 80.8%); $[\alpha]_D$ +88.7° (c 0.25, methanol). Lit$^{22}$ $[\alpha]_D$ +90° (c 1.0, methanol). $^1$H-n.m.r. (D$_2$O): δ 5.11(d, 1H, J$_{1',2'}$ 3.8 Hz, H-1'), 5.06(d, 1H, J$_{1,2}$ 3.8 Hz, H-1), 3.65(s, 3H, OCH$_3$), 2.37(t, 2H, J 7.5 Hz, C$\underline{H}_2$COO).

Example 51

Synthesis of 8-Methoxycarbonyloctyl 2-O-(6-azido-6-deoxy-α-D-glucopyranosyl)-α-D-glucopyranoside (46).

Compound 10 (50 mg, 0.05 mmol) was hydrogenated as described for the preparation of 44 to give 45 which was converted into 6'-azido derivative as described for the preparation of 11 to provide 46 (22 mg, 81.1%) as a white solid after lyophilization; $[\alpha]_D$ +69.7° (c 0.15, water); $^1$H-n.m.r. (D$_2$O): δ 5.13(d, 1H, J$_{1',2'}$ 3.8 Hz, H-1'), 5.08(d, 1H, J$_{1,2}$ 3.8 Hz, H-1), 3.68(s, 3H, OCH$_3$) 2.38(t, 2H J 7.5 Hz, C$\underline{H}_2$COO).

Example 52

Synthesis of 8-Methoxycarbonyloctyl 2-O-(6-amino-6-deoxy-α-D-glucopyranosyl)-α-D-glucopyranoside (47).

Compound 11 (92 mg, 0.10 mmol) was hydrogenated as described for the preparation of 44 to provide 47 (44 mg, 83.8%) as a white foam after lyophilization; $[\alpha]_D$ +94.3° (c 0.11, water); $^1$H-n.m.r. (D$_2$O): δ 5.11(d, 1H, J$_{1',2'}$3.8 Hz, H-1), 5.08(d, 1H, J$_{1,2}$ 3.8 Hz, H-1), 2.35(t, 2H, J 7.5 Hz, C$\underline{H}_2$COO).

Example 53

Synthesis of 8-Methoxycarbonyloctyl 2-O-(6-chloro-α-D-glucopyranosyl)-α-D-glucopyranoside (48).

Compound 12 (102 mg, 0.11 mmol) was hydrogenated as described for the preparation of 44 to provide 48 (52 mg, 85.4%) as a white powder after lyophilization; $[\alpha]_D$ +107.1° (c 0.18, water); $^1$H-n.m.r. (D$_2$O): δ 5.14(d, 1H,J$_{1',2'}$3.8 Hz, H-1'), 5.08(d, 1H, J$_{1,2}$ 3.8 Hz, H-1), 3.70(s, 3H, OCH$_3$) 2.39(t, 2H J 7.5 Hz, C$\underline{H}_2$COO).

Example 54

Synthesis of 8-Methoxycarbonyloctyl 2-O-(6-fluoro-α-D-glucopyranosyl)-α-D-glucopyranoside (49).

Compound 13 (75 mg, 0.09 mmol) was hydrogenated as described for the preparation of 44 to provide 49 (40 mg, 90.5%) as a white amorphous solid following lyophilization. $[\alpha]_D$ +108.6° (c 0.12, water); $^1$H-n.m.r. (D$_2$O): δ 5.13(d, 1H, J$_{1',2'}$ 3.8 Hz, H-1'), 5.10(d, 1H, J$_{1,2}$ 3.8 Hz, H-1), 3.69(s, 3H, OCH$_3$), 2.39(t, 2H, J 7.5 Hz, C$\underline{H}_2$COO).

Example 55

Synthesis of 8-Methoxycarbonyloctyl 2-O-(6-deoxy-α-D-glucopyranosyl)-α-D-glucopyranoside (50).

Compound 15 (56 mg, 0.06 mmol) was hydrogenated as described for the preparation of 44 to provide 50 (25.5 mg, 77.5%) as a white powder after lyophilization; $[\alpha]_D$ +88.3° (c 0.12, water); $^1$H-n.m.r. (D$_2$O): δ 5.12(d, 1H, J$_{1',2'}$ 3.8 Hz, H-1'), 5.02(d, 1H, J$_{1,2}$ 3.8 Hz, H-1), 3.69(s, 3H, OCH$_3$), 2.39(t, 2H, J 7.5 Hz, C$\underline{H}_2$COO).

Example 56

Synthesis of 8-Methoxycarbonyloctyl 3-O-methyl-2-O-(α-D-glucopyranosyl)-α-D-glucopyranoside (51).

Compound 16 (38 mg, 0.043 mmol) was hydrogenated as described for the preparation of 44 to provide 51 (18 mg, 79.6%) as a white powder after lyophilization; $[\alpha]_D$ +113.6° (c 0.06, water); $^1$H-n.m.r. (D$_2$O): δ 5.15(d, 1H, J$_{1',2'}$ 3.8 Hz, H-1'), 5.08(d, 1H, J$_{1,2}$ 3.8 Hz, H-1), 3.70, 3.62(s, 3H each, 2×OCH$_3$), 2.39(t, 2H J 7.5 Hz, C$\underline{H}_2$COO).

Example 57

Synthesis of 8-Methoxycarbonyloctyl 2-O-(6-O-methyl-α-D-glucopyranosyl)-α-D-glucopyranoside (52).

Compound 17 (55 mg, 0.062 mmol) was hydrogenated as described for the preparation of 44 to provide 52 (27 mg, 82.5%) as a white powder after lyophilization; $[\alpha]_D$ +98.9° (c 0.14, water); $^1$H-n.m.r. (D$_2$O): δ 5.14(d, 1H, J$_{1',2'}$ 3.8 Hz, H-1'), 5.07(d, 1H, J$_{1,2}$ 3.8 Hz, H-1), 3.70(s, 3H, OCH$_3$), 3.40(s, 3H, OCH$_3$), 2.4(t, 2H J 7.5 Hz, C$\underline{H}_2$COO).

Example 58

Synthesis of 8-Methoxycarbonyloctyl 3-O-methyl-2-O-(6-O-methyl-α-D-glucopyranosyl)-α-D-glucopyranoside (53).

Compound 18 (35 mg. 0.039 mmol) was hydrogenated as described for the preparation of 44 to provide 53 (16.5 mg, 78.4%), as a white powder after lyophilization: $[\alpha]_D$ +50.0° (c 0.50, water); $^1$H-n.m.r. (D$_2$): δ 5.11(d, 1H, J$_{1',2'}$ 3.8 Hz, H-1'), 5.04(d, 1H, J$_{1,2}$ 3.8 Hz, H-1), 3.68, 3.61 and 3.39(s, 3H each, 3×OCH$_3$), 2.38(t, 2H J 7.5 Hz, C$\underline{H}_2$COO).

Example 59

Synthesis of 8-Methoxycarbonyloctyl 3-deoxy-2-O-(α-D-glucopyranosyl)-α-D-glucopyranoside (54).

Compound 21 (132 mg, 0.14 mmol) was dissolved in dichloromethane (2 mL) to which was added 80% aqueous acetic acid (100 mL) and stirred the reaction mixture for 20 h at room temperature. Evaporated and coevaporated with toluene followed by hydrogenation as described for the preparation of 44 to provide 54 (58.5 mg, 86.5%) as a white powder; $[\alpha]_D$ +142.3° (c 0.050, water); $^1$H-n.m.r. (D$_2$O): δ 5.08(d, 1H, J$_{1',2'}$ 3.8 Hz, H-1'), 5.01(d, 1H, J$_{1,2}$ 3.8 Hz, H-1), 3.69(s, 3H, OCH$_3$) 2.39(t, 2H J 7.5 Hz, C$\underline{H}_2$COO), 2.25 (ddd, 1H, J$_{3a,3e}$ 12.0 Hz, J$_{2,3e}$ 4.5 Hz, H-3e), 1.85(ddd, 1H, J 11.5 and 11.0 Hz, H-3a).

Example 60

Synthesis of 8-Methoxycarbonyloctyl 6-azido-2-O-(α-D-glucopyranosyl)-α-D-glucopyranoside (56).

Compound 25 (150 mg, 0.16 mmol) was hydrogenated as described for the preparation of 44 which was directly converted into its 6-azido derivative as described for the preparation of 11. Deacetylation followed by chromatography on Iatrobeads provided pure 56 (70 mg, 81.9%) as a powder after lyophization. $[\alpha]_D$ +63.9° (c 0.12, water); $^1$H-n.m.r. (D$_2$O): δ 5.16(d, 1H, J$_{1',2'}$ 3.8 Hz, H-1'), 5.08(d, 1H, J$_{1,2}$ 3.8 Hz, H-1), 3.70(s, 3H, OCH$_3$), 2.29(t, 2H, J 7.5 Hz, C$\underline{H}_2$COO).

Example 61

Synthesis of 8-Methoxycarbonyloctyl 6-amino-6-deoxy-2-O-(α-D-glucopyranosyl)-α-D-glucopyranoside (57).

Compound 26 (52 mg, 0.06 mmol) was O-deacetylated as described for the preparation of 3 to give 34 which was directly hydrogenated as described for the preparation of 44 to provide 57 (25 mg, 83.8%) as a white powder after lyophilization; $[\alpha]_D$ +89.5° (c 0.32, water); $^1$H-n.m.r. (D$_2$O): δ 5.14(d, 1H, J$_{1',2'}$ 3.8 Hz, H-1'), 5.05(d, 1H, J$_{1,2}$ 3.8 Hz, H-1), 3.67(s, 3H, OCH$_3$), 2.38(t, 2H, J 7.5 Hz, C$\underline{H}_2$COO).

Example 62

Synthesis of 8-Methoxycarbonyloctyl 6-chloro-2-O-(α-D-glucopyranosyl)-α-D-glucopyranoside (58).

Compound 27 (82 mg, 0.09 mmol) was O-deacetylated as described for the preparation of 3 to give 35 which was hydrogenated as described for the preparation of 44 to provide 58 (42 mg, 85.2%) as a white powder after lyophilization; $[\alpha]_D$ +95° (c 0.07, water); $^1$H-n.m.r. (D$_2$O): δ 5.16(d, 1H, J$_{1',2'}$ 3.8 Hz, H-1'), 5.09(d, 1H, J$_{1,2}$ 3.8 Hz, H-1), 3.65(s, 3H, OCH$_3$) 2.39(t, 2H J 7.5 Hz, C$\underline{H}_2$COO).

Example 63

Synthesis of 8-Methoxycarbonyloctyl 6-fluoro-(α-D-glucopyranosyl)-α-D-glucopyranoside (59).

Compound 40 (72 mg, 0.08 mmol) was hydrogenated as described for the preparation of 44 to provide 59 (32 mg, 83.4%) as a powder after lyophilization; $[\alpha]_D$ +90.9° (c 0.11, water). $^1$H-n.m.r. (D$_2$O): δ 5.18(d, $^1$H, J$_{1',2'}$ 3.8 Hz, H-1'), 5.08(d, 1H, J$_{1,2}$ 3.8 Hz, H-1), 3.70(s, 3H, OCH$_3$), 2.39(t, 2H, J 7.5 Hz, C$\underline{H}_2$COO).

Example 64

Synthesis of 8-Methoxycarbonyloctyl 6-deoxy-2-O-(α-D-glucopyranosyl)-α-D-glucopyranoside (60).

Compound 29 (50 mg, 0.06 mmol) was O-deacetylated as described for the preparation of 3 to give 36 which was hydrogenated as described for the preparation of 44 to provide 60 (22.5 mg, 77.1%) as a white powder after lyophilization; $[\alpha]_D$ +128.6° (c 0.11, water); $^1$H-n.m.r. (D$_2$O): δ 5.10(d, 1H, J$_{1',2'}$ 3.8 Hz, H-1'), 5.08(d, 1H, J$_{1,2}$ 3.8

Hz, H-1), 3.69(s, 3H, OCH$_3$), 2.40(t, 2H, J 7.5 Hz, CH$_2$COO), 1.29(d, 1H, J$_{5,6}$ 7.5 Hz, H-6).

Example 65

Synthesis of 8-Methoxycarbonyloctyl 4O-methyl-2-O-(α-D-glucopyranosyl)-α-D-glucopyranoside (61).

Compound 41 (52 mg, 0.053 mmol) was hydrogenated as described for the preparation of 44 to provide 61 (25 mg, 89.2%) as a white powder after lyophilization; [α]$_D$ +115 (c 0.28, water); $^1$H-n.m.r. (D$_2$O): δ 5.20(d, 1H, J$_{1',2'}$ 3.8 Hz, H-1'), 5.13(d, 1H, J$_{1,2}$ 3.8 Hz, H-1), 3.75, 3.46(s, 3H each, 2×OCH$_3$) 2.39(t, 2H J 7.5 Hz, CH$_2$COO).

Example 66

Synthesis of 8-Methoxycarbonyloctyl 6-O-methyl-2-O-(α-D-glucopyranosyl)-α-D-glucopyranoside (62).

Compound 42 (65 mg, 0.067 mmol) was hydrogenated as described for the preparation of 44 to provide 62 (30 mg, 85.7%) as a white powder after lyophilization; [α]$_D$ +128.2° (c 0.17, water); $^1$H-n.m.r. (D$_2$O): δ 5.13(d, 1H, J$_{1',2'}$ 3.8 Hz, H-1'), 5.07(d, 1H, J$_{1,2}$ 3.8 Hz, H-1), 3.69, 3.57(s, 3H each, 2×OCH$_3$) 2.39(t, 2H J 7.5 Hz, CH$_2$COO).

Example 67

Synthesis of 8-Methoxycarbonyloctyl 4,6-di-O-methyl-2-O-(α-D-glucopyranosyl)-α-D-glucopyranoside (63).

Compound 43 (32 mg, 0.032 mmol) was hydrogenated as described for the preparation of 40 to give 57 (15 mg, 86%) as a white powder after lyophilization; [α]$_D$ +45.8° (c 0.24, water); $^1$H-n.m.r. (D$_2$O): δ 5.11(d, 1H, J$_{1',2'}$ 3.8 Hz, H-1'), 5.05(d, 1H, J$_{1,2}$ 3.8 Hz, H-1), 3.69, 3.56, 3.42(s, 3H each, 3×OCH$_3$), 2.39(t, 2H J 7.5 Hz, CH$_2$COO).

Example 68

Synthesis of 8-Methoxycarbonyloctyl 4-deoxy-2-O-(-α-D-glucopyranosyl)-α-D-glucopyranoside (64).

Compound 33 (75 mg, 0.085 mmol) was dissolved in dichloromethane (2 mL) and added to it was 80% aqueous acetic acid. After stirring for 20 h at room temperature, the reaction mixture was evaporated and coevaporated with toluene to give 37 as a syrup which was hydrogenated as described for the preparation of 44 to provide 64 (33.5 mg, 79.2%) as a white powder after lyophilization; [α]$_D$ +113.6° (c 0.33, water); $^1$H-n.m.r. (D$_2$O): δ 5.13(d, 1H, J$_{1',2'}$ 3.8 Hz, H-1'), 5.04(d, 1H, J$_{1,2}$ 3.8 Hz, H-1), 3.64(s, 3H, OCH$_3$), 2.34(t, 2H, J 7.5 Hz, CH$_2$COO), 1.97(m, 1H, H-4e), 1.45 (ddd, 1H, J$_{3,4}$ J$_{4,5}$ 12.0 Hz, J$_{4a,4c}$ 12.5 Hz, H-4a).

Example 69

Synthesis of 8-Methoxycarbonyloctyl 2-O-(2-fluoro-α-D-glucopyranosyl)-α-D-glucopyranoside (99).

Compound 80 (55 mg, 0.07 mmol) was O-deacetylated as described for the preparation of 3 to give 81 which was directly hydrogenated as described for the preparation of 44 to provide 99 (33.5 mg, 91.2%) as a white powder after lyophilization; [α]$_D$+128.6° (c 0.10, water); $^1$H-n.m.r. (D$_2$O): δ 5.31(d, 1H, J$_{1',2'}$ 3.8 Hz, H-1'), 5.15(d, 1H, J$_{1,2}$ 3.8 Hz, H-1), 3.69(s, 3H, OCH$_3$), 2.38(t, 2H, J 7.5 Hz, CH$_2$COO).

Example 70

Synthesis of 8-Methoxycarbonyloctyl 2-O-(2-azido-α-D-glucopyranosyl)-α-D-glucopyranoside (100).

Compound 82 (58 mg, 0.07 mmol) was O-deacetylated as described for the preparation of 3 to give 83 which was treated with 80% aqueous acetic acid (150 mL) for 15 h at room temperature. After evaporation and co-evaporation with toluene it was purified by chromatography on Iatrobeads using (chloroform:methanol:water; 80:20:2) as eluant to provide 100 (35 mg, 89.2%); [α]$_D$+119.8° (c 0.20, water); $^1$H-n.m.r. (D$_2$O): δ 5.20(d, 1H, J$_{1',2'}$ 3.8 Hz, H-1'), 5.15(d, 1H, J$_{1,2}$ 3.8 Hz, H-1), 3.69(s, 3H, OCH$_3$), 2.38(t, 2H, J 7.5 Hz, CH$_2$COO).

Example 71

Synthesis of 8-Methoxycarbonyloctyl 2-O-(2-amino-2-deoxy-α-D-glucopyranosyl)-α-D-glucopyranoside (101).

Compound 82 (132 mg, 0.17 mmol) was O-deacetylated as described for the preparation of 3 to give 83 which was hydrogenated exactly as described for compound 44 to provide 101 (72 mg, 84.6%) as a white powder after lyophilization; [α]$_D$+146.7° (c 0.25, water); $^1$H-n.m.r. (D$_2$O): δ 5.09(d, 1H, J$_{1',2'}$ 3.8 Hz, H-1'), 5.01(d, 1H, J$_{1,2}$ 3.8 Hz, H-1), 3.69(s, 3H, OCH$_3$), 2.39(t, 2H, J 7.5 Hz, CH$_2$COO).

Example 72

Synthesis of 8-Methoxycarbonyloctyl 2-O-(2-O-methyl-α-D-glucopyranosyl)-α-D-glucopyranoside (102).

Compound 84 (55.6 mg, 0.06 mmol) was O-deacetylated as described for the preparation of 3 to give 85 which was hydrogenated exactly as described for the compound 44 to provide 102 (25 mg, 79.2%) as a white powder after lyophilization; [α]$_D$+92.1° (c 0.12, water); $^1$H-n.m.r. (D$_2$O): 5.36(d, 1H, J$_{1',2'}$ 3.8 Hz, H-1'), 5.19(d, 1H, J$_{1,2}$ 3.8 Hz, H-1), 3.69(s, 3H, OCH$_3$), 3.49(s, 3H, OCH$_3$), 2.39(t, 2H, J 7.5 Hz, CH$_2$COO).

Example 73

Synthesis of 8-Methoxycarbonyloctyl 2-O-(2-deoxy-α-D-glucopyranosyl)-α-D-glucopyranoside (103).

Compound 86 (78 mg, 0.09 mmol) was O-deacetylated as described for the preparation of 3 to give 87 which was hydrogenated exactly as processed for the compound 44 to provide 103 (36.5 mg, 84.5%) as a powder after lyophilization; [α]$_D$+74.2° (c 0.28, water); $^1$H-n.m.r. (D$_2$O): 5.22(bd, 1H, J$_{1',2'}$ 3.2 Hz, H-1'), 5.18(d, 1H, J$_{1,2}$ 3.8 Hz, H-1), 3.72(s, 3H, OCH$_3$), 2.42(t, 2H, J 7.5 Hz, CH$_2$COO), 2.17(dd, 1H, J 5.0 and 12.5 Hz H-2e), 1.77(ddd, 1H, J 2.5 and 12.0 Hz, H-2a).

Example 74

Synthesis of 8-Methoxycarbonyloctyl 2-O-(3-deoxy-α-D-glucopyranosyl)-α-D-glucopyranoside (104).

Compound 88 (92 mg, 0.10 mmol) was O-deacetylated as described for the preparation of 3 to give 99 which as hydrogenated as processed for 44 to provide 104 (38 mg, 74.6%); $[\alpha]_D$+105.9° (c 0.23, water); $^1$H-n.m.r. (D$_2$O): δ 5.14(t, 1H, J$_{1',2'}$3.8 Hz, H-1'), 4.96(s, 1H, J$_{1,2}$ 3.8 Hz, H-1), 3.69(s, 3H, OCH$_3$), 2.39(t, 2H, J 7.5 Hz, CH$_2$COO), 2.17 (ddd, 1H, J$_{3a,3e}$ 12.0, J$_{2,3e}$ 4.5, H-3e), 1.87(ddd, 1H, J 11.5 and 11.0 Hz, H-3a).

Example 75

Synthesis of 8-Methoxycarbonyloctyl 2-O-(3-O-methyl-α-D-glucopyranosyl)-α-D-glucopyranoside (105).

Compound 90 (48.8 mg, 0.05 mmol) was O-deacetylated as described for the preparation of 3 to give 91 which was hydrogenated exactly as described for the compound 44 to provide 105 (23.9 mg, 86.2%) an a white powder after lyophilization; $[\alpha]_D$+110° (c 0.09, water); $^1$H-n.m.r. (D$_2$O): 5.13(d, 1H, J$_{1',2'}$3.8 Hz, H-1'), 5.06(d, 1H, J$_{1,2}$ 3.8 Hz, H-1), 3.69(s, 3H, OCH$_3$), 3.56(s, 3H, OCH$_3$), 2.39(t, 2H, J 7.5 Hz, CH$_2$COO).

Example 76

Synthesis of 8-Methoxycarbonyloctyl 2-O-(4-deoxy-α-D-glucopyranosyl)-α-D-glucopyranoside (106).

Compound 92 (60 mg, 0.07 mmol) was O-deacetylated as described for the preparation of 3 to give 93 which as hydrogenated as processed for 44 to provide 106 (28 mg, 84.3%) as a white powder after lyophilization; $[\alpha]_D$+132°0 (c 0.12, water); $^1$H-n.m.r. (D$_2$O): δ 5.12(s, 1H, J$_{1',2'}$3.8 Hz, H-1'), 5.08(s, 1H, J$_{1,2}$ 3.8 Hz, H-1), 3.67(s, 3H, OCH$_3$), 2.36(t, 2H, J 7.5 Hz, CH$_2$COO), 1.98(m, 1H, H-3e) 1.45 (ddd, 1H, J$_{3,4}$=J$_{4,5}$ 12.0, J$_{4a,4e}$ 12.5, H-4a).

Example 77

Synthesis of 8-Methoxycarbonyloctyl 2-O-(4-O-methyl-α-D-glucopyranosyl)-α-D-glucopyranoside (107).

Compound 94 (72 mg, 0.08 mmol) was O-deacetylated as described for the preparation of 3 to provide 95 which was directly hydrogenated exactly as described for the compound 44 to give 107 (34.5 mg, 84.4%) as a white powder after lyophilization; $[\alpha]_D$+108° (c 0.08, water); $^1$H-n.m.r. (D$_2$O): 5.15(d, 1H, J$_{1',2'}$3.8 Hz, H-1'), 5.06(d, 1H, J$_{1,2}$ 3.8 Hz, H-1), 3.69(s, 3H, OCH$_3$), 3.63(s, 3H, OCH$_3$) 2.39(t, 2H, J 7.5 CH$_2$COO).

Example 78

Synthesis of 8-Methoxycarbonyloctyl 2-O-(α-D-xylopyranosyl)-α-D-glucopyranoside (108).

Compound 97 (55 mg, 0.06 mmol) was O-deacetylated as described for the preparation of 3 to give 98 which was hydrogenated as described for the preparation of 44 to provide 108 (22.5 mg, 80.0%); $[\alpha]_D$+91° (c 0.45, water); $^1$H-n.m.r. (D$_2$O): δ 5.08(d, 1H, J$_{1',2'}$3.8 Hz, H-1'), 5.01(d, 1H, J$_{1,2}$ 3.8 Hz, H-1), 3.70(s, 3H, OCH$_3$) 2.38(t, 2H J 7.5 Hz, CH$_2$COO).

Example 79

Synthesis of 2,3,4-tri-O-benzyl-xylopyranosyl bromide

Xylopyranose (15.0 g) was dissolved in allyl alcohol (150 mL) and trifluoromethane sulfonic acid (235 µL) was dropwise added 0° C. The reaction was stirred at 0° C. for 15 minutes and then heated at 80° C. for 4 hours. The reaction solution was then neutralized with triethylamine and evaporated to dryness. Chromatography of the material of silica gel using dichloromethne-methanol (19:1) as eluent provided allyl-xylopyranose (14.9 g).

Allyl-xylopyranose (1.62 g) was benzylated with benzyl bromide and sodium hydride and then dissolved in a mixture of ethanol-benzene-water (7:3:1) (34 mL) and tris triphenylphosphine rhodium (I) chloride (250 mg) and 1,4-diazabicyclo[2.2.2]octane (108 mg) were added. The resulting solution was then refluxed for 1 hour. The solvent was evaporated to dryness and the residue redissolved in a mixture of acetone-water (9:1, 40 mg) to which was added mercury (II) chloride (8.9 g) and mercury (II) oxide (86 mg). The solution was then stirred for 2 hours at room temperature. The solvent was evaporated and the residue dissolved in CH$_2$Cl$_2$ (250 mL) and washed successively with 30% aqueous KBr (2×250 mL) and water (2×250 mL) before evaporation to a syrup. Evaporated and crystallized from ether and hexane to provide crystals of 2,3,4-tri-O-benzyl-xylopyranose (2.0 g).

2,3,4-tri-O-benzyl-xylopyranose was dissolved in dry dichloromethane (50 mL) and dry DMF (3.0 mL) was added. The reaction mixture was cooled at 0° C. and added dropwise oxayl bromide (1.4 mL). The reaction mixture was stirred for 1 hour at 0° to 5° C. and then diluted with dichloromethane (250 mL), washed with water (2×250 mL), dried over Na$_2$SO$_4$, filtered and evaporated to provide the title compound. The yield was quantitative for this step.

2,3,4-tri-O-benzyl-xylopyranose bromide was then used to prepare compound 108 via methods similar to those described above using compound 6.

The syntheses outlined in Examples 80–82 are also reported in U.S. patent application Ser. No. 08/485,057, filed concurrently herewith as attorney docket No. 000475-051 and entitled "MODIFIED α-D-Glcp-(1-2)-α-D-Glcp-(1-3)-α-D-Glcp-ANALOGUES" which application is incorporated herein by reference in its entirety.

Example 80

Synthesis of 1,5-trans-(α-D)-C-glucopyranosyl-amino-(glucose)

Figure 5:
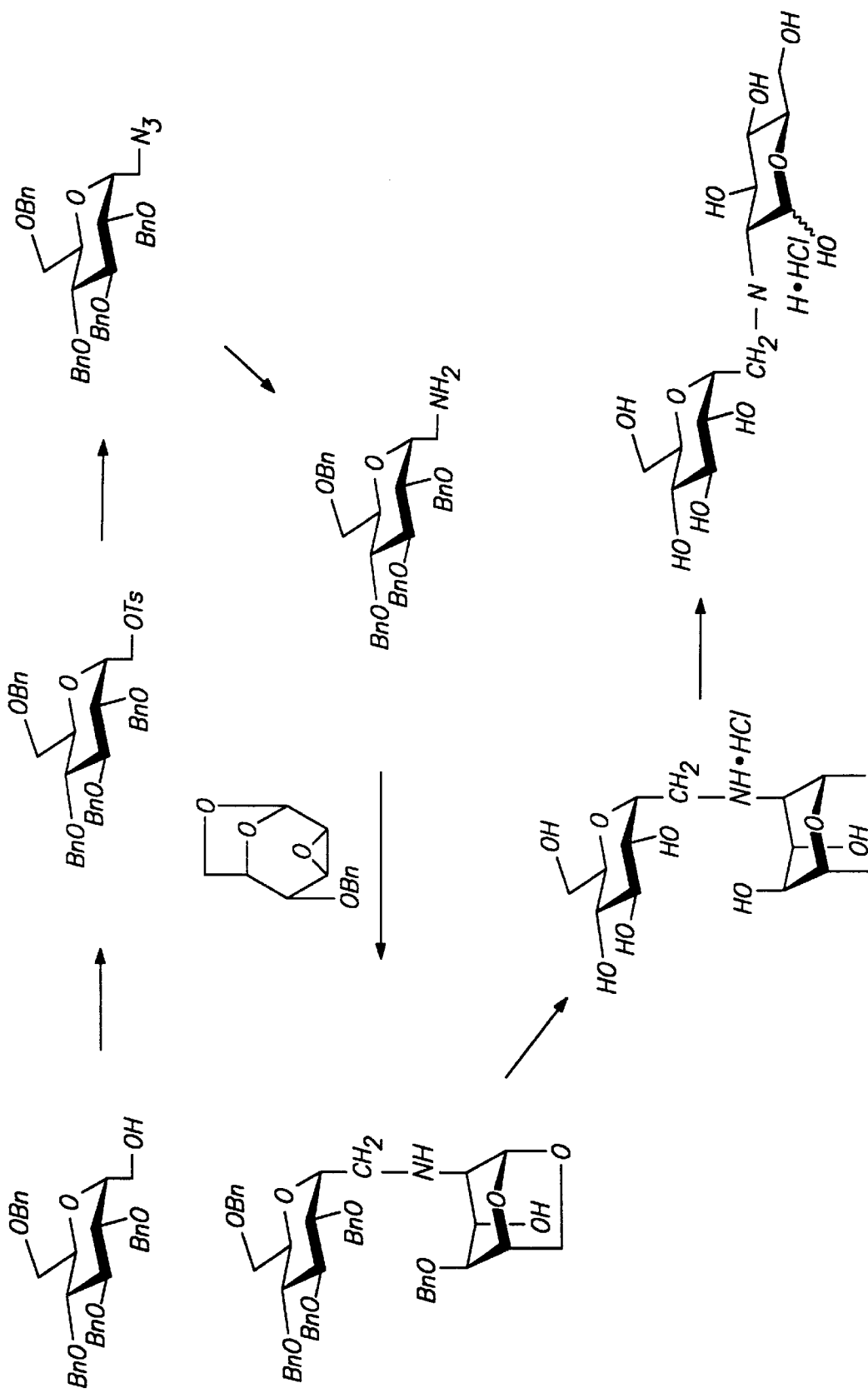
FIG. 5 illustrates the synthesis of 1,5-trans-(C)-glucopyranosyl-amino- 1,6-anhydroglucose and 1,5-trans (C)glucopyransoyl-amino-glucose.

The reactions used to prepare the title compound are set forth in FIG. 5

A. Synthesis of 1-C-tosyloxymethyl-2,3,4,6-tetra-O-benzyl-1,5-trans(α-D)-C-glucopyranoside To a solution of 1-C-hydroxymethyl-1,5-trans(α-D)-C-2,3,4,6-tetra-O-benzylglucopyranose (526 mg) in dry pyridine (5.0 mL) was added p-toluene-sulfonyl chloride (270 mg) and the reaction mixture was stirred for 15 hours at room temperature. The reaction mixture was evaporated and the residue purified by chromatography on silica gel column using hexane-ethyl acetate (3:1) as eluent to provide for 1-C-tosyloxymethyl-2,3,4,6-tetra-O-benzyl-1,5-trans(α-D)-C-glucopyranoside (613 mg).

B. Synthesis of 1-C-azidomethyl-2,3,4,6-tetra-O-benzyl-1,5-trans(α-D)-C-glucopayanoside To a solution of 1-C-tosyloxymethyl-2,3,4,6-tetra-O-benzyl-1,5-trans(α-D)-C-glucopyranoside (588 mg) in DMF (10.0 mL), sodium azide (380 mg) was added and the reaction mixture was then heated at 80° C. for 15 hours. Solvent was evaporated from the mixture under high vacuum and the product was purified by chromatography on silica gel using hexane:ethyl acetate (10:1) as eluent to provide 1-C-azidomethyl-2,3,4,6-tetra-O-benzyl-1,5-trans (α-D)-C-glucopyanoside (420 mg); [α]D+30° (C 0.735, CHCl₃).

C. Synthesis of 1-C-methyl amino-2,3,4,6-tetra-O-benzyl-1,5-trans(α-D)-C-glucopyranoside 1-C-azidomethyl-2,3,4,6-tetra-O-benzyl-1,5 trans(α-D)-C glucopyanoside (391 mg) was dissolved in a mixture of pyridine-water-triethylamine (26:4:0.8, 10 mL). A stream of hydrogen sulfide was bubbled at 0° C. for 1 hour and then allowed to warm at room temperature. After bubbling for 5 hours at room temperature, hydrogen sulfide was filled at 0° C. for 15 minutes and stirred at room temperature for 15 hours. The mixture was evaporated to dryness and coevaporated with toluene (3×50 mL) and purified by chromatography on silica gel using chloroform-methanol (9:1) as eluent to obtain 1-C-methyl amino-2,3,4,6-tetra-O-benzyl-1,5-trans(α-D)-C glucopyranoside (380 mg).

D. Synthesis of 2,3,4,6-tetra-O-benzyl-1,5-trans-(α-D)-C-amino-(1,6-anhydro-4-O-benzyl-glucopyranose A solution of 1-C-methyl amino-2,3,4,6-tetra-O-benzyl-1,5-trans(α-D)-C glucopyranoside (380 mg) and 1,6-anhydro4-O-benzyl-2,3-epoxy-glucose made according to the method set forth in Cerny et al, J. Czechosl Chem. Commun. 39 (1974) (937 mg) in n-propanol (6.0 mL) was heated at 90° C. for 3 days. Solvent was evaporated, then co-evaporated with toluene and the residue was chromatographed on a silica gel column using chloroform-ethyl acetate (2:1) as eluent to obtain (320 mg) 2,3,4,6-tetra-O-benzyl-1,5-trans-(α-D)-C-1-methyl-amino-(1,6anhydro4-O-benzyl-glucopyranose.

E. Synthesis of 1,5-trans-(α-D)-C-glucopyranosyl-1-methylamino-(1,6-anhydro)glucopyranose 2,3,4,6-tetra-O-benzyl- 1,5-trans-(α-D)-C-1-methyl-amino-(1,6-anhydro-4-O-benzyl-glucopyranose (361 mg, 0.46 mmol) was dissolved in a mixture of methanol-acetic acid (20:1, 10 mL) and 5% palladium on carbon (360 mg) was added. 0.46 mmol of hydrochloric acid was also added and stirred the reaction mixture for 3 hours at room temperature at one atmospheric pressure. Filtered the catalyst on the pad of celite and evaporated to dryness. Compound was purified by chromatography on silica gel using dichloromethane-methanol-water (65:35:5) as eluent which was further purified by Sephadex column filtration using ethanol-water (1:1) as eluent to provide 1,5-trans-α-D-C-glucopyranosyl-1-methylamino-(1,6-anhydro) glucopyranose (148 mg, 86.4%).

F. Synthesis of 1,5-trans-(α-D)-C-glucopyranosyl-1-methylamino-(glucose)

1,5-trans-(α-D)-C-glucopyranosyl-1-methylamino-(1,6-anhydroglucopyranose (115 mg, 0.31 mmol) was heated at 100° C. in 2N HCl solution for 4 days. Solvent was removed by co-evaporation with water and the residue was purified by chromatography on Iatrobeads using chloroform-methanol-water (65:35:5) as eluent to provide for the title compound (82mg, 68%).

Example 81

Synthesis of methyl-2-O-[1,5-trans-(α-D)-C-glucopyranosyl]-α-D-glucopyranoside

Figure 6:
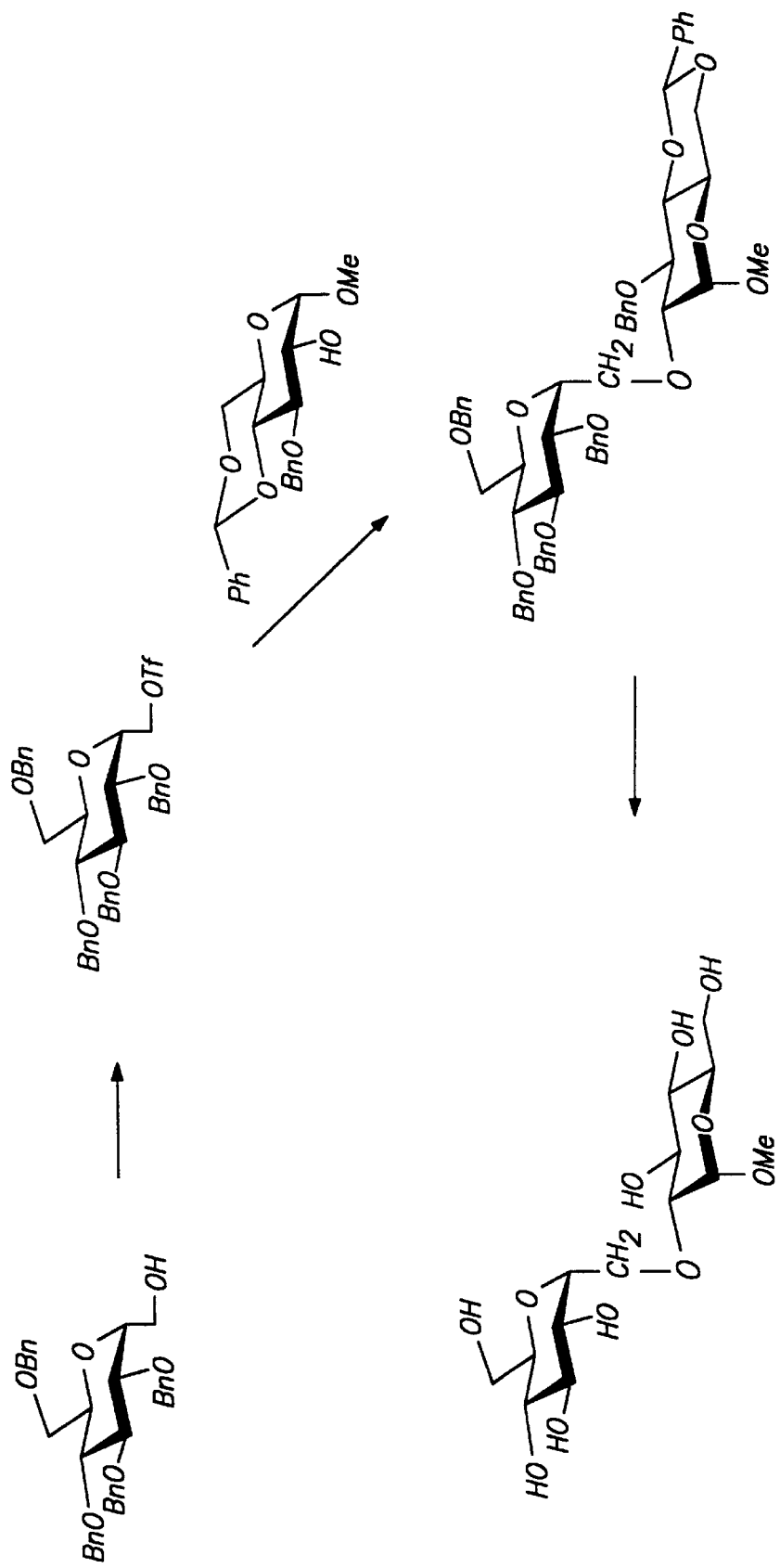
FIG. 6 illustrates the synthesis of methyl-2-O-(1,5-trans-(C)glucopyranosyl)-α-D-glucopyranoside.

The synthesis of the compounds in this example is illustrated in FIG. 6.

A. Synthesis of 1-C-hydroxytrifluoromethane sulfonyl-1,5-trans-(α-D)-C-2,3,4,6-tetra-O-benzylglucopyranose 1-C-hydroxymethyl-1,5-trans-(α-D)-C-2,3,4,6-tetra-O-benzylglucopyranose (670 mg, 1.21 mmol) was dissolved in dichloromethane (5.5 mL) and pyridine (294 μL) was added.

At −20° C. triflic anhydride (2.5 mL) was added and stirred the reaction mixture for 45 minutes at this temperature. Diluted the reaction mixture with dichloromethane (100 mL) and washed with saturated solution of sodium bicarbonate (2×100 mL) and water (2×100 mL), dried over sodium sulfate, filtered and evaporated to dryness which was used directly for the next reaction.

B. Synthesis of methyl-2-O-[1,5-trans-α-D)-C-2,3,4,6-tetra-O-benzylglucopyranosyl]-3-O-benzyl-4,6-O-benzylidene-α-D-glucopyranoside Methyl-3-O-benzyl-4,6-O-benzylidene-α-D-glucopyranoside (185 mg, 0.50 mmol) was dissolved in anhydrous THF and cooled to 0° C. 1 molar solution of [(CH₃)₃Si]₂NLi (1.49 mmol) was added in THF dropwise. It was stirred for 1 h at 0° C. and 2 days at room temperature. Compound was evaporated and purified by chromatography on silica gel using hexane-ethyl acetate (4:1) as eluent to give methyl-2-O-[1,5-trans-(α-D)-C-2,3,4,6-tetra-O-benzylglucopyranosyl]-3-O-benzyl-4,6-O-benzylidene-α-D-glucopyranoside (60 mg).

C. Synthesis of methyl-2-O-[1,5-trans-(α-D)-C-glucopyranosyl]-α-D-glucopyranoside Methyl-2-O-(1,5-trans-(α-D)-C-2,3,4-tetra-O-benzylglucopyranosyl]-3-O-benzyl-4,6-O-benzylidene-α-D-glucopyranoside (50.0 mg) was hydrogenated as described earlier using 5% palladium on carbon (50 mg) in methanol (5.0 mL). After the usual work up, methyl-2-O-[1-C-hydroxymethyl-1,5-trans-(α-D)-C-glucopyranosyl]-α-D-glucopyranoside (20 mg) was obtained after lyophilization.

Example 82

Synthesis of homonojirimycin-glucose (18)

Figure 7:
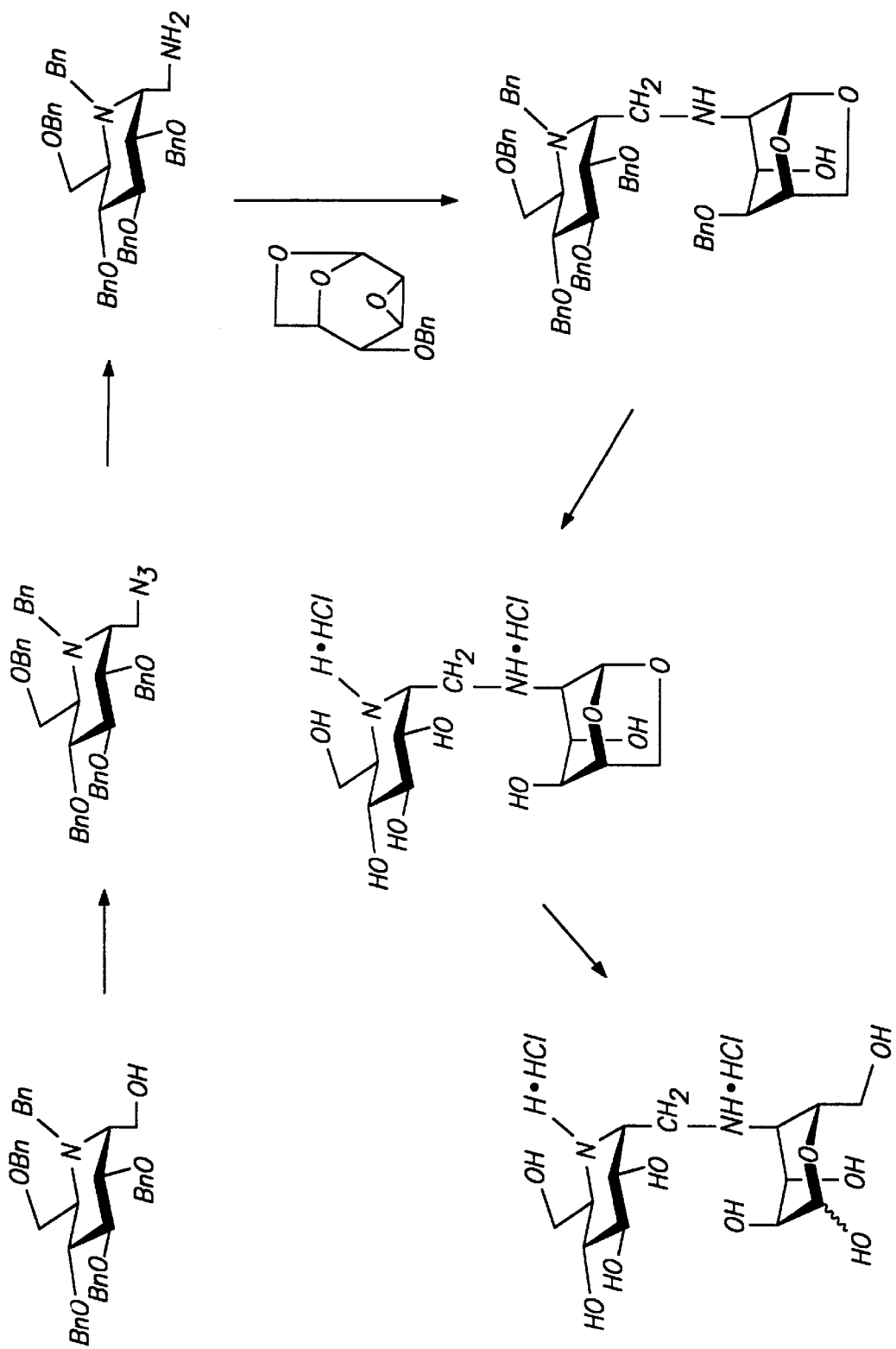
FIG. 7 illustrates the synthesis of homonojirimycin-amino-1,6-anhydroglucose and homonojirimycin-amino-glucose.

The synthesis of the compounds in this example is illustrated in FIG. 7.

A. Synthesis of protected homonojirimycin

Fully protected N-benzyl-tetra-O-benzyl-homonojirimycin (prepared according to the literature Liu et al., J. Org. Chem., Vol 51, No. 21, 1987) (128 mg) was dissolved in toluene (1.5 mL) and added to it trphenylphosphine (226 mg) followed by addition of hydrazoic acid (12.5 mL) solution in benzene (10%) and DEAD (14.2 μL). The reaction mixture was stirred at room temperature for 2.5 h. Diluted with CH₂Cl₂ (50 mL) washed with water (2×50 mL), dried over Na₂SO₄ and evaporated. The syrup was purified by chromatography on silica gel using hexane-ethyl acetate (10:1) as eluent to obtain the azido derivative of homonojirimycin (112 mg).

B. Synthesis of N-benzyl-tetra-O-benzyl-amino-derivative of homonojirimycin

The product of A) above (112 mg) was dissolved in a mixture of pyridine-water-triethyl amine (26:4:0.8, 10.0 mL) and cooled to 0° C. for 1 h and stirred overnight at room temperature. The reaction mixture was evaporated, co-evaporated with toluene and purified by chromatography on silica gel using chloroform-ethyl acetate (1:1) as eluent to give N-benzyl-tetra-O-benzyl-amino-derivative of homonojirimycin (48.0 mg).

C. Synthesis of protected homonojirimycin-amino- 1,6-anhydroglucose

A solution of N-benzyl-tetra-O-benzyl-amino-derivative of homonojirimycin (48 mg, 0.72 mmol) and 1,6-anhydro-4-O-benzyl-2,3-epoxyglucose (100 mg) in n-propanol was stirred at 90° C. for 2 days. Evaporated the reaction mixture and purified by chromatography on silica gel using hexane-ethyl acetate (3:1) as eluent. Pure product (43 mg) was obtained.

D. Synthesis of homonojirimycin-1,6-amino-anhydroglucose

The compound prepared in C above (43 mg) was dissolved in methanol (3.0 mL) and 1.1 equivalents of hydrochloric acid and 5% palladium on carbon (43 mg) was added. Stirred the reaction mixture for 15 h at one atmospheric pressure and room temperature. Purification, after usual workup, by chromatography on silica gel chloroform-methanol-water (60:40:5) as eluent provided homonojirimycin-1,6-anhydroglucose (19 mg).

E. Synthesis of homonojirimycin-amino-glucose

Homonojirimycin-amino-1,6-anhydroglucose (15 mg) was heated at 100° C. in 2N HCl solution for 4 days. Solvent was removed by evaporation with water and the residue was purified by chromatography on an Iatrobead column using chloroform-methanol-water (60:40:5) as eluent to provide the title compound (8.0 mg) after lyophilization.

Figure 4:
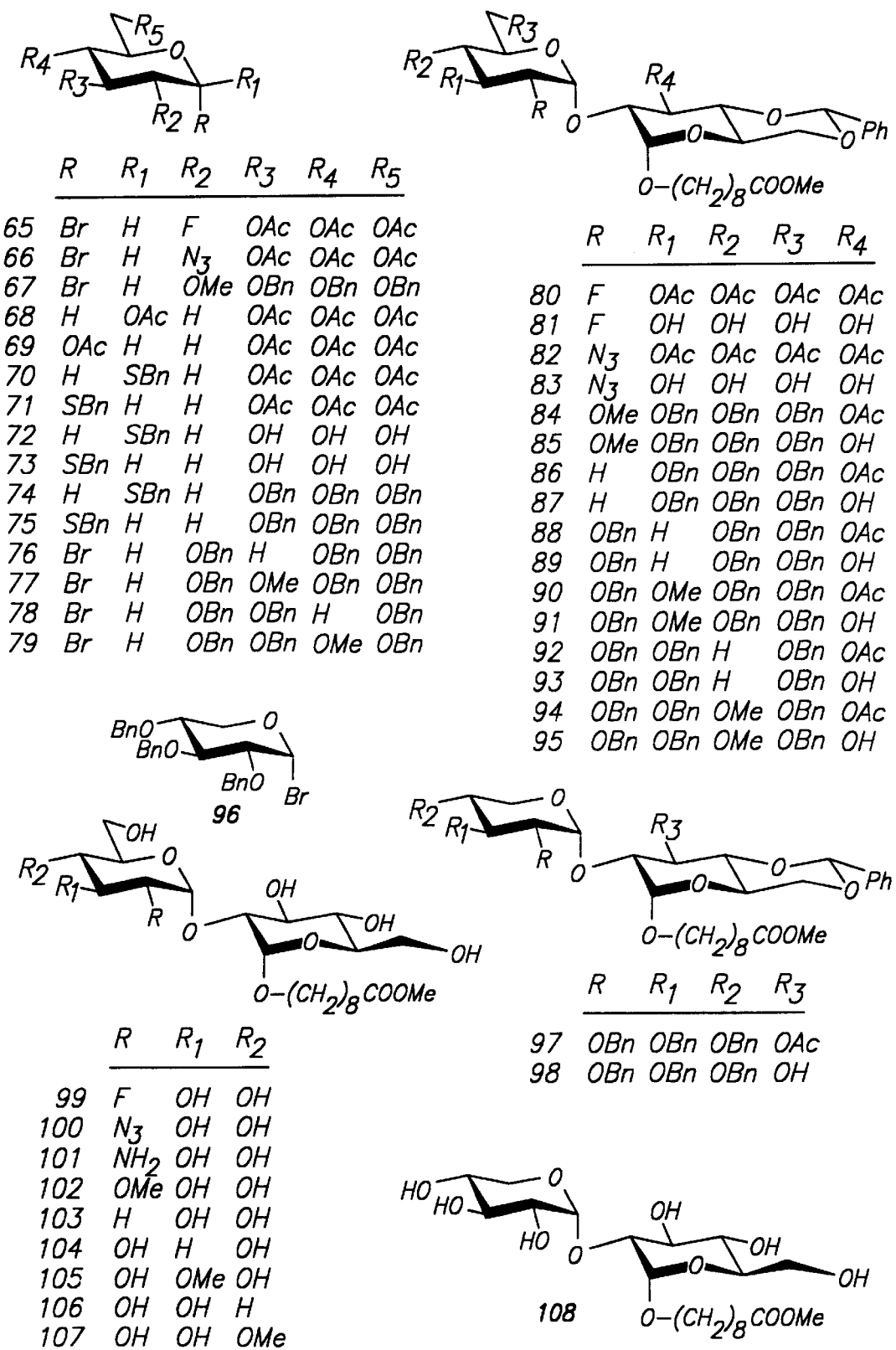

Other compounds which can readily be prepared as set forth above include in Formula III of FIG. 4, R is —OSi(CH$_3$)$_2$t-butyl, R$^1$=hydrogen; in Formula VI of FIG. 4, R is O-mesityl, and R$^1$ is —OH.

Biological Results

Some of the compounds described herein were evaluated as inhibitors of glucosidase I activity. Glucosidase I was purified by a literature procedure as follows. To prepare an affinity matrix, carboxypentyl-deoxynojirimycin was coupled with Affigel 102 according to Shailubhai et al[51]. Glucosidase I was solubilized from calf pancreas microsomes, and purified from glucosidase II activity by affinity chromatography according to the same authors.

Substrates for Assay of Glucosidase I

[14]C-labelled Glc$_3$Man$_9$GlcNAc$_2$-PP-Dol was prepared by the incubation of UDP-$^{14}$C]Glc with calf pancreas microsomes as described by Herscovien et al[52]. Glc$_3$Man$_9$GlcNAc$_2$ was released by mild acid hydrolysis and purified by BioGel P4 chromatography.

Assay for Glucosidase I Activity

Affinity purified glucosidase I was assayed as described by Saunier et al.[53] by adsorption of undigested substrate and oligosaccharide product to ConA-Sepharose and scintillation counting of $^{14}$C]Glc in the column eluent. Oligosaccharides as potential inhibitors were evaluated using castanospermine as a baseline inhibitor.

Results

Following the procedures set forth above, known compound 44 inhibited glucosidase I activity (20% at 1 mM concentration) whereas compound 57 evidenced a 70% increase in inhibition activity (i.e., 34% at 1 mM concentration).

While the invention has been described in terms of various preferred embodiments, the skilled artisan will appreciate the various modifications, substitutions, omissions and changes which may be made without departing from the spirit thereof. The descriptions of subject matter in this disclosure are illustrative of the invention and are not intended to be construed as limitations upon the scope of the invention.

What is claimed is:

1. A compound useful as an α-glucosidase I inhibitor or as an intermediate in the production of α-glucosidase I inhibitor selected from the group consisting of compounds represented by formulas I–IV, VII and VIII

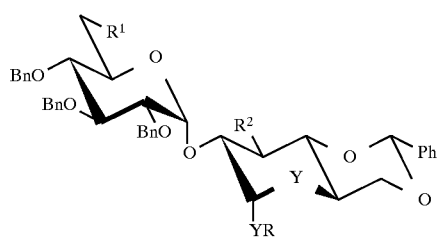

wherein each Y is independently —O— or —NH—, R is an aglycon of at least 1 carbon atom, R$^1$ is selected from the group consisting of —O-acetyl, —OH, —O-mesityl, —N$_3$, —Cl, —F, —I, —H, —O-methyl, —OSi(CH$_3$)$_2$-tert-butyl and —O-benzyl; and R$^2$ is selected from the group consisting of —O-acetyl, —OH, —O-methyl, —OC(S)O-phenyl, —H and —O-benzyl;

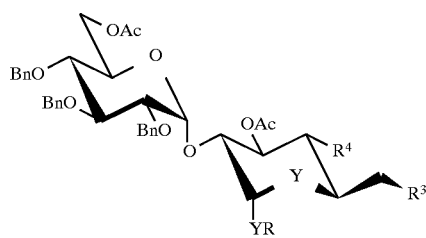

wherein each Y is independently —O— or —NH—, R is an aglycon of at least 1 carbon atom, R$^3$ is selected from the group consisting of —OH, —O-mesityl, —N$_3$, —Cl, —I, —H, —OSi(CH$_3$)$_2$-tert-butyl; and R$^4$ is selected from the group consisting of —OH, —H and —OC(S)O-phenyl;

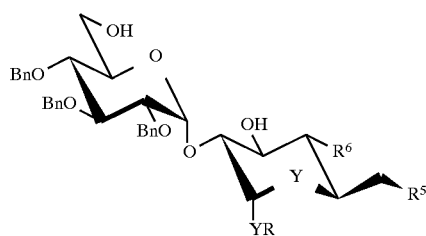

wherein each Y is independently —O— or —NH—, R is an aglycon of at least 1 carbon atom, R$^5$ is selected from the group consisting of —OSi(CH$_3$)$_2$ tert-butyl, —N$_3$, —Cl, —H and —OH and R$^6$ is selected from the group consisting of hydrogen and —OH;

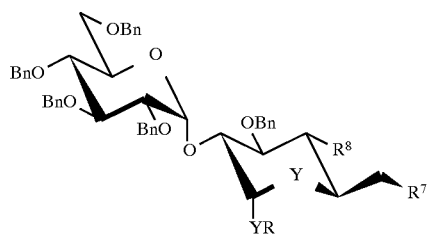

wherein each Y is independently —O— or —NH—, R is an aglycon of at least 1 carbon atom, R$^7$ is selected from the group consisting of —OH, —O-mesityl, —F, —OH and —O-methyl; and R$^8$ is selected from the group consisting of —OH and —O-methyl;

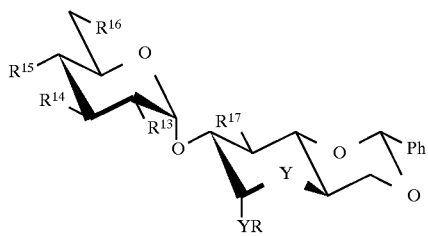

VII

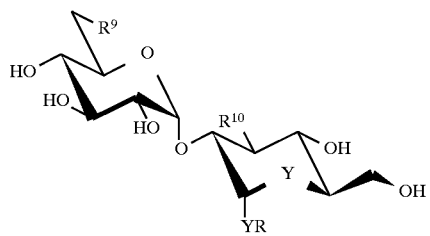

V wherein each Y is independently —O— or —NH—, R is an aglycon of at least 1 carbon atom, $R^{13}$ is selected from the group consisting of —F, —$N_3$, —O-methyl, —H, and —O-benzyl; $R^{14}$ is selected from the group consisting —O-acetyl, —OH, —O-benzyl, —H and —O-methyl; $R^{15}$ is selected from the group consisting —O-acetyl, —OH, —O-benzyl, —H and —O-methyl; $R^{16}$ is selected from the group consisting of —OH, O-acetyl and —O-benzyl; and $R^{17}$ is selected from the group consisting of —O-acetyl and —OH; and

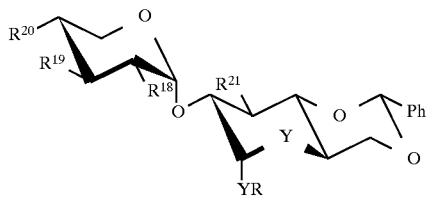

VIII wherein each Y is independently —O— or —NH—, R is an aglycon of at least 1–20 carbon atoms, $R^{18}$, $R^{19}$ and $R^{20}$ are —O-benzyl and $R^{21}$ is —O-acetyl or —OH.

2. A compound according to claim 1 wherein said compound is of formula I.

3. A compound according to claim 2 wherein said compound is selected from the group consisting of compounds 8 through 23 of FIG. 2.

4. A compound according to claim 1 wherein said compound is of formula II.

5. A compound according to claim 4 wherein said compound is selected from the group consisting of compounds 24 through 32 of FIG. 3.

6. A compound according to claim 1 wherein said compound is of formula III.

7. A compound according to claim 6 wherein said compound is selected from the group consisting of compounds 33 through 37 of FIG. 3.

8. A compound according to claim 1 wherein said compound is of formula IV.

9. A compound according to claim 8 wherein said compound is selected from the group consisting of compounds 38 through 43 of FIG. 3.

10. A compound according to claim 1 wherein said compound is of formula VII.

11. A compound according to claim 10 wherein said compound is selected from the group consisting of compounds 80 through 95 of FIG. 4.

12. A compound according to claim 1 wherein said compound is of formula VIII.

13. A compound according to claim 12 wherein said compound is selected from the group consisting of compounds 97 through 98 of FIG. 4.

14. A compound useful as a α-glucosidase I inhibitor or as an intermediate in the production of an α-glucosidase I inhibitor selected from the group consisting of compounds represented by formulas V, VI, IX, X, XI, XII and XIII:

wherein each Y is independently —O— or —NH—, R is an aglycon of at least 1 carbon atom, $R^9$ is selected from the group consisting of —O-mesityl, —$N_3$, —$NH_2$, —Cl, —F, —H, —OH, and —O-methyl and $R^{10}$ is selected from the group consisting of —OH, —H and —O-methyl, with the proviso that when each Y is —O— and $R^9$ is hydroxyl, then $R^{10}$ is not hydroxyl;

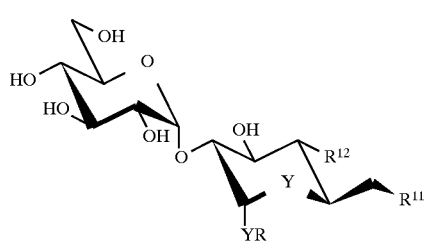

VI wherein each Y is independently —O— or —NH—, R is an aglycon of at least 1 carbon atom, $R^{11}$ is selected from the group consisting of —O-mesityl, —$N_3$, —$NH_2$, —Cl, —F, —H, —OH and —O-methyl and $R^{12}$ is selected from the group consisting of —OH, —H and —O-methyl with the proviso that when each Y is —O— and $R^{11}$ is hydroxyl, then $R^{12}$ is not hydroxyl;

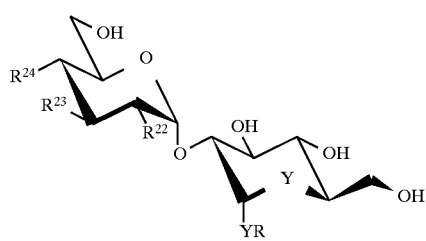

IX wherein each Y is independently selected from —O— or —NH—, R is an aglycon of at least 1 carbon atom, $R^{22}$ is selected from the group consisting of —F, —$N_3$, —$NH_2$, —O-methyl, —H and —OH; and $R^{23}$ and $R^{24}$ are selected from the group consisting of —OH, —H and —O-methyl with the proviso that when each Y is —O—, $R^{22}$ is hydroxyl and $R^{23}$ is hydroxyl, then $R^{24}$ is not hydroxyl;

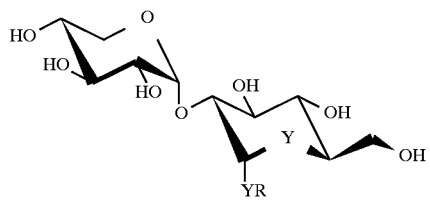

X wherein each Y is independently —O— or —NH— and R is an aglycon of at least 1 carbon atom;

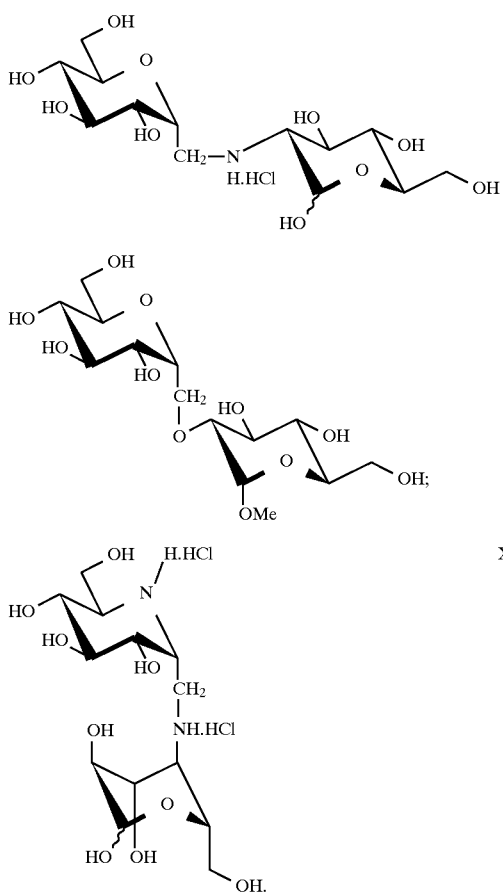

15. A compound according to claim 14 wherein said compound is of formula V.

16. A compound according to claim 15 wherein said compound is selected from the group consisting of compounds 44 through 54 of FIG. 3.

17. A compound according to claim 14 wherein said compound is of formula VI.

18. A compound according to claim 17 wherein said compound is selected from the group consisting of compounds 55 through 64 of FIG. 3.

19. A compound according to claim 14 wherein said compound is of formula IX.

20. A compound according to claim 19 wherein said compound is selected from the group consisting of compounds 99 through 107 of FIG. 4.

21. A compound according to claim 14 wherein said compound is of formula X.

22. A compound according to claim 21 wherein said compound is compound 108 of FIG. 4.

23. A compound according to claim 14 wherein said compound is of formula XI.

24. A compound according to claim 14 wherein said compound is of formula XII.

25. A compound according to claim 14 wherein said compound is of formula XIII.

26. A pharmaceutical composition comprising a pharmaceutically inert carrier and from 0.1 to 95 weight percent of a compound of claim 14.

* * * * *